(12) United States Patent
Lee et al.

(10) Patent No.: US 9,455,409 B2
(45) Date of Patent: Sep. 27, 2016

(54) AMINE-BASED COMPOUND AND ORGANIC LIGHT EMITTING DEVICE INCLUDING THE SAME

(71) Applicant: Samsung Display Co., Ltd., Yongin, Gyeonggi-do (KR)

(72) Inventors: Ji-Youn Lee, Yongin (KR); Yoon-Hyun Kwak, Yongin (KR); Bum-Woo Park, Yongin (KR); Sun-Young Lee, Yongin (KR); Jong-Won Choi, Yongin (KR); Wha-Il Choi, Yongin (KR); So-Yeon Kim, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 437 days.

(21) Appl. No.: 13/959,273

(22) Filed: Aug. 5, 2013

(65) Prior Publication Data
US 2014/0117329 A1 May 1, 2014

(30) Foreign Application Priority Data
Oct. 29, 2012 (KR) .................. 10-2012-0120612

(51) Int. Cl.
| | |
|---|---|
| H01L 51/50 | (2006.01) |
| H01L 51/00 | (2006.01) |
| C07D 401/12 | (2006.01) |
| C07D 409/14 | (2006.01) |
| C07D 209/88 | (2006.01) |

(52) U.S. Cl.
CPC ........... *H01L 51/006* (2013.01); *C07D 209/88* (2013.01); *C07D 401/12* (2013.01); *C07D 409/14* (2013.01); *H01L 51/0061* (2013.01); *H01L 51/0067* (2013.01); *H01L 51/0072* (2013.01); *H01L 51/0081* (2013.01); *H01L 51/0085* (2013.01); *H01L 51/0087* (2013.01); *H01L 51/5056* (2013.01)

(58) Field of Classification Search
None
See application file for complete search history.

(56) References Cited

U.S. PATENT DOCUMENTS

| | | | |
|---|---|---|---|
| 5,635,308 A | 6/1997 | Inoue et al. | |
| 5,645,948 A | 7/1997 | Shi et al. | |
| 5,972,247 A | 10/1999 | Shi et al. | |
| 6,465,115 B2 | 10/2002 | Shi et al. | |
| 6,596,415 B2 | 7/2003 | Shi et al. | |
| 7,431,997 B2 | 10/2008 | Hwang et al. | |
| 7,737,627 B2 | 6/2010 | Hwang et al. | |
| 2005/0221124 A1 | 10/2005 | Hwang et al. | |
| 2011/0193074 A1* | 8/2011 | Lee ................ | H01L 51/0072 257/40 |
| 2011/0240979 A1* | 10/2011 | Kim ................ | C07D 487/04 257/40 |

FOREIGN PATENT DOCUMENTS

| | | |
|---|---|---|
| JP | 08-12600 | 1/1996 |
| JP | 2000-003782 | 1/2000 |

(Continued)

OTHER PUBLICATIONS

Tang et al., "Organic electroluminescent diodes." *Appl. Phys. Lett.*, Sep. 21, 1987, pp. 913-915, vol. 51, No. 12. American Institute of Physics.
Adachi, et al., "Confinement of charge carriers and molecular excitons within 5-nm-thick emitter layer in organic electroluminescent devices with a double heterostructure." *Appl. Phys. Lett.*, Aug. 6, 1990, pp. 531-533, vol. 57, No. 6. American Institute of Physics.
Sakamoto et al., "Synthesis, Characterization, and Electron-Transport Property of Perfluorinated Phenylene Dendrimers." *J. Am. Chem. Soc.* 2000, pp. 1832-1833, vol. 122, No. 8. American Chemical Society.

(Continued)

*Primary Examiner* — Gregory Clark
(74) *Attorney, Agent, or Firm* — Knobbe Martens Olson & Bear LLP

(57) ABSTRACT

An amine-based compound and an organic light-emitting device including the amine-based compound are provided.

20 Claims, 1 Drawing Sheet

(56) References Cited

FOREIGN PATENT DOCUMENTS

| JP | 2011-001349 | | 1/2011 | |
|---|---|---|---|---|
| KR | 10-2005-0097670 | | 10/2005 | |
| KR | 10-0573137 | * | 4/2006 | ............. C09K 11/06 |
| KR | 10-2010-0039815 | | 4/2010 | |

OTHER PUBLICATIONS

Yamaguchi et al., "Diphenylamino-Substituted 2,5-Diarylsiloles for Single-Layer Organic Electroluminescent Devices." *Chemistry Lettters*, 2001, pp. 98-99. The Chemical Society of Japan.

* cited by examiner

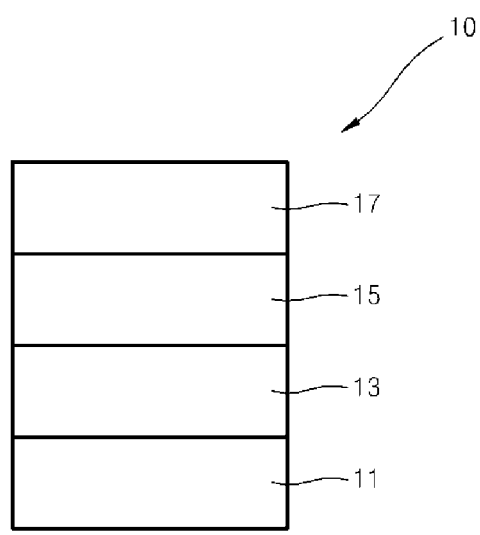

AMINE-BASED COMPOUND AND ORGANIC LIGHT EMITTING DEVICE INCLUDING THE SAME

CROSS-REFERENCE TO RELATED APPLICATIONS

This application claims the benefit of Korean Patent Application No. 10-2012-0120612, filed on Oct. 29, 2012, in the Korean Intellectual Property Office, the disclosure of which is incorporated herein in its entirety by reference.

BACKGROUND

1. Field

The present embodiments relate to an amine-based compound and an organic light-emitting device including the same.

2. Description of the Related Technology

Organic light-emitting devices (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films comprising organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

The present embodiments provide a novel amine-based compound and an organic light-emitting device including the same.

According to an aspect of the present embodiments, there is provided an amine-based compound represented by Formula 1 below:

<Formula 1>

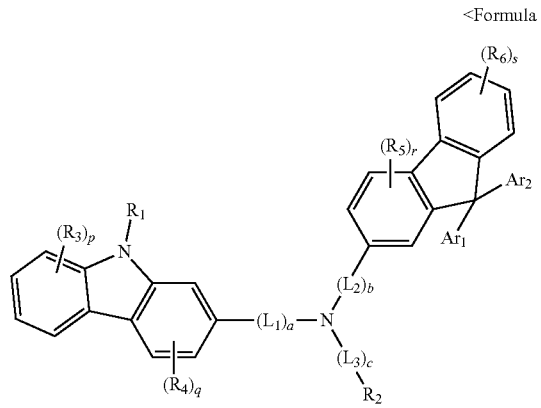

wherein, in Formula 1, $Ar_1$ and $Ar_2$ are each independently a substituted or unsubstituted $C_6$-$C_{30}$ aryl group, and $Ar_1$ and $Ar_2$ are optionally linked to each other via a single bond;

$L_1$ to $L_3$ are each independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{30}$ arylene group, or a substituted or unsubstituted $C_2$-$C_{60}$ hetero arylene group;

a, b, and c are each independently an integer from 0 to 5;

$R_1$ to $R_6$ are each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_3$-$C_{60}$ heterocycloalkyl group, a substituted or unsubstituted $C_3$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, $-N(Q_1)(Q_2)$, or $-Si(Q_3)(Q_4)(Q_5)$, wherein $Q_1$ to $Q_5$ are each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_3$-$C_{60}$ heterocycloalkyl group, a substituted or unsubstituted $C_3$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

p and s are each independently an integer from 1 to 4; and
q and r are each independently an integer from 1 to 3.

According to another aspect of the present embodiments, there is provided an organic light-emitting device including: a first electrode; a second electrode disposed opposite to the first electrode; and an organic layer disposed between the first electrode and the second electrode, wherein the organic layer includes at least one of the amine-based compounds of Formula 1 above.

BRIEF DESCRIPTION OF THE DRAWING

The above and other features and advantages of the present embodiments will become more apparent by describing in detail example embodiments thereof with reference to the attached drawing in which:

FIG. 1 schematically illustrates the structure of an organic light-emitting device according to an embodiment.

DETAILED DESCRIPTION

As used herein, the term "and/or" includes any and all combinations of one or more of the associated listed items.

Expressions such as "at least one of," when preceding a list of elements, modify the entire list of elements and do not modify the individual elements of the list.

According to an aspect of the present embodiments, there is provided an amine-based compound represented by Formula 1 below:

<Formula 1>

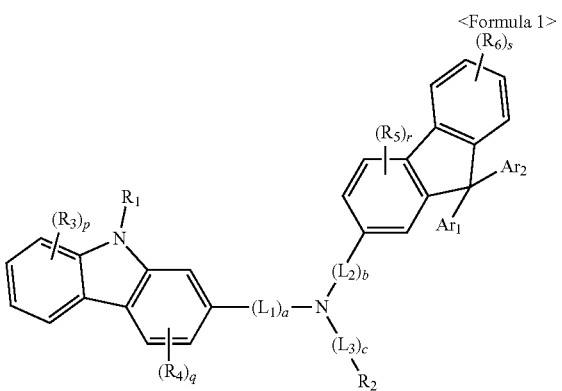

In Formula 1 above, $Ar_1$ and $Ar_2$ may be each independently a substituted or unsubstituted $C_6$-$C_{30}$ aryl group. $Ar_1$ and $Ar_2$ may be optionally linked to each other via a single bond.

$Ar_1$ and $Ar_2$ may be each independently one of a $C_6$-$C_{14}$ aryl group; and a $C_6$-$C_{14}$ aryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group.

For example, $Ar_1$ and $Ar_2$ may be each independently a substituted or unsubstituted phenyl group, a substituted or unsubstituted naphthyl group, or a substituted or unsubstituted anthryl group.

In some embodiments, $Ar_1$ and $Ar_2$ may be each independently one of a phenyl group, a naphthyl group, and an anthryl group; and a phenyl group, a naphthyl group, and an anthryl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group, but are not limited thereto.

$Ar_1$ and $Ar_2$ may be identical to or differ from each other.

In Formula 1, $L_1$ to $L_3$ may be each independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{30}$ arylene group, or a substituted or unsubstituted $C_2$-$C_{60}$ hetero arylene group.

For example, $L_1$ to $L_3$ may be each independently one of a $C_6$-$C_{14}$ arylene group, and a $C_2$-$C_{14}$ hetero arylene group; and a $C_6$-$C_{14}$ arylene group, and a $C_2$-$C_{14}$ hetero arylene that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group, but are not limited thereto.

In some embodiments, $L_1$ to $L_3$ may be each independently one of a phenylene group, a naphthylene group, an anthrylene group, a pyridinylene group, a pyrimidinylene group, a triazinylene group, and a thiophenylene group; and a phenylene group, a naphthylene group, an anthrylene group, a pyridinylene group, a pyrimidinylene group, a triazinylene group, and a thiophenylene group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group, but are not limited thereto.

In Formula 1, a indicates the number of $L_1$s, b indicates the number of $L_2$s, and c indicates the number of $L_3$s. When a is 0, the carbazole and N in Formula 1 may be directly linked to each other. When b is 0, the fluorene and N in Formula 1 may be directly linked to each other. When c is 0, $R_2$ and N may be directly linked to each other. When a is 2 or greater, at least two of $L_1$s may be identical to or differ from each other. When a is 2 or greater, at least two of $L_2$s may be identical to or differ from each other. When c is 2 or greater, at least two of $L_3$s may be identical to or differ from each other.

In Formula 1, a and b may be each independently an integer from 0 to 5.

For example, in Formula 1, a may be an integer from 1 to 5.

In some embodiments, all of a and b may be 0. In some other embodiments, a, b, and c may be each independently 0, 1, or 2, but are not limited thereto.

In Formula 1, $R_1$ to $R_6$ may be each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_3$-$C_{60}$ heterocycloalkyl group, a substituted or unsubstituted $C_3$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, $-N(Q_1)(Q_2)$, or $-Si(Q_3)(Q_4)(Q_5)$, wherein $Q_1$ to $Q_5$ may be each independently, a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_3$-$C_{60}$ heterocycloalkyl group, a substituted or unsubstituted $C_3$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

For example, $R_1$ and $R_2$ may be each independently one of a phenyl group, a naphthyl group, an anthryl group, a pyridinyl group, a pyrimidinyl group, a triazinyl group, and a thiophenyl group; and a phenyl group, a naphthyl group, an anthryl group, a pyridinyl group, a pyrimidinyl group, a triazinyl group, and a thiophenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group, but are not limited thereto.

In some embodiments, $R_3$ to $R_6$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{60}$ alkoxy group; a phenyl group, a naphthyl group, an anthryl group, a pyridinyl group, a pyrimidinyl group, triazinyl group, and a thiophenyl group; and a phenyl group, a naphthyl group, an anthryl group, a pyridinyl group, a pyrimidinyl group, a triazinyl group, and a thiophenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group.

In Formula 1, p indicates the number of $R_3$s, q indicates the number of $R_4$s, r indicates the number of $R_5$s; and s indicates the number of $R_6$s. When p is 2 or greater, at least two of $R_3$ s may be identical to or differ from each other. When q is 2 or greater, at least two of $R_4$s may be identical to or differ from each other. When r is 2 or greater, at least two of $R_5$s may be identical to or differ from each other. When s is 2 or greater, at least two of $R_6$s may be identical to or differ from each other.

The amine-based compound may be a compound represented by Formula 1A or 1B below:

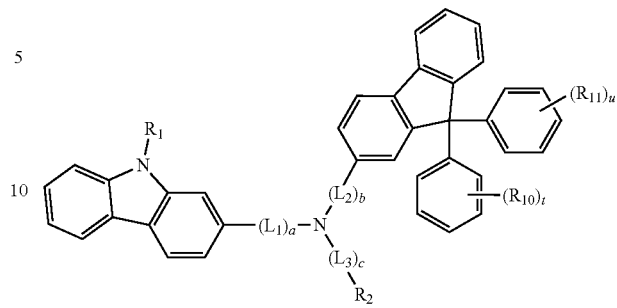

<Formula 1A>

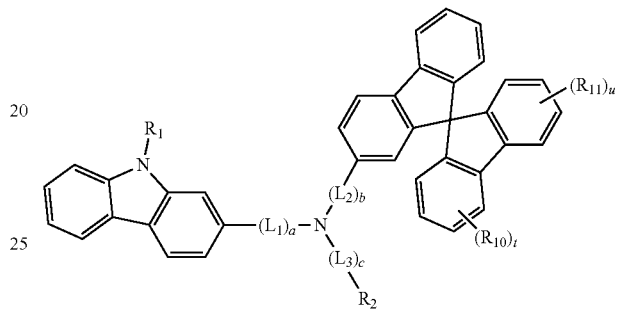

<Formula 1B>

In Formulae 1A and 1B, $L_1$ to $L_3$, a, b, c, $R_1$, and $R_2$ are as defined above, $R_{10}$ and $R_{11}$ are as defined above in conjunction with $R_1$, t and u are each independently an integer from 1 to 4.

For example, in Formulae 1A and 1B, i) $L_1$ to $L_3$ may be each independently one of a phenylene group, a naphthylene group, an anthrylene group, a pyridinylene group, a pyrimidinylene group, a triazinylene group, and a thiophenylene group; and a phenylene group, a naphthylene group, an anthrylene group, a pyridinylene group, a pyrimidinylene group, a triazinylene group, and a thiophenylene group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group; ii) a may be an integer from 1 to 5, and a, b, and c may be each independently 0, 1, or 2; iii) $R_1$ and $R_2$ may be each independently one of a phenyl group, a naphthyl group, an anthryl group, a pyridinyl group, a pyrimidinyl group, a triazinyl group, and a thiophenyl group; and a phenyl group, a naphthyl group, an anthryl group, a pyridinyl group, a pyrimidinyl group, a triazinyl group, and a thiophenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group; iv) $R_{10}$ and $R_{11}$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{60}$ alkoxy group; a phenyl group, a naphthyl group, an anthryl group, a pyridinyl group, a pyrimidinyl group, a triazinyl group, and a thiophenyl group; and a phenyl group, a naphthyl group, an anthryl group, a pyridinyl group, a pyrimidinyl group, a triazinyl group, and a thiophenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl; and v) t and u may be each independently an integer from 1 to 4, but are not limited thereto.

In some other embodiments, the amine-based compound may be a compound represented by one of Formulae 1A(1), 1A(2), 1B(1), and 1B(2), but is not limited thereto:

<Formula 1A(1)>

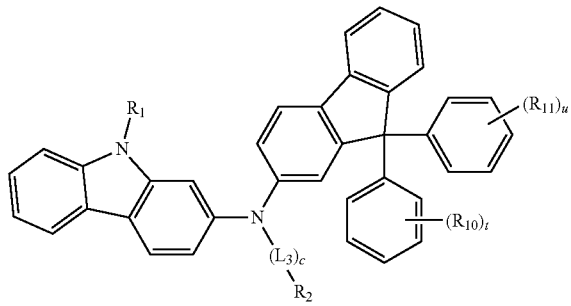

<Formula 1A(2)>

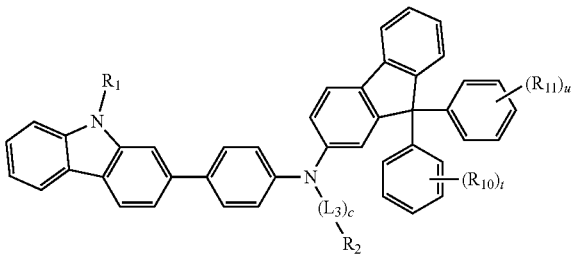

<Formula 1B(1)>

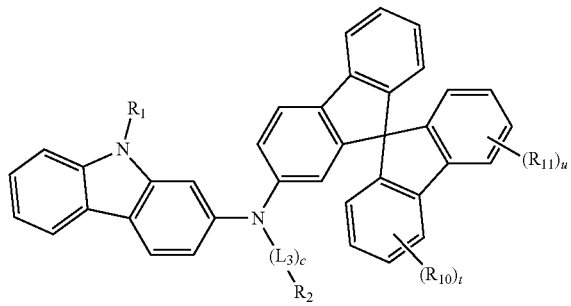

<Formula 1B(2)>

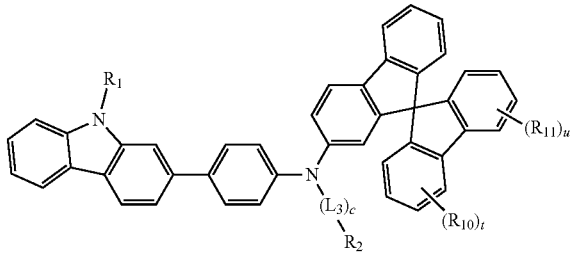

In Formulae 1A(1), 1A(2), 1B(1), and 1B(2), $L_3$, c, $R_1$, and $R_2$ are as defined above, $R_{10}$ and $R_{11}$ are as defined above in conjunction with $R_1$, and t and u are each independently an integer from 1 to 4.

For example, in Formulae 1A(1), 1A(2), 1B(1), and 1B(2), i) $L_3$ may be one of a phenylene group, a naphthylene group, an anthrylene group, a pyridinylene group, a pyrimidinylene group, a triazinylene group, and a thiophenylene group; and a phenylene group, a naphthylene group, an anthrylene group, a pyridinylene group, a pyrimidinylene group, a triazinylene group, and a thiophenylene group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group; ii) c may be 0, 1, or 2; iii) $R_1$ and $R_2$ may be each independently one of a phenyl group, a naphthyl group, an anthryl group, a pyridinyl group, a pyrimidinyl group, a triazinyl group, and a thiophenyl group; and a phenyl group, a naphthyl group, an anthryl group, a pyridinyl group, a pyrimidinyl group, a triazinyl group, and a thiophenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group; iv) $R_{10}$ and $R_{11}$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{60}$ alkoxy group; a phenyl group, a naphthyl group, an anthryl group, a pyridinyl group, a pyrimidinyl group, a triazinyl group, and a thiophenyl group; and a phenyl group, a naphthyl group, an anthryl group, a pyridinyl group, a pyrimidinyl group, a triazinyl group, and a thiophenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group; and v) t and u may be each independently an integer from 1 to 4, but are not limited thereto.
In some embodiments, the amine-based compound may be one of Compounds 1 to 48 below, but is not limited thereto:
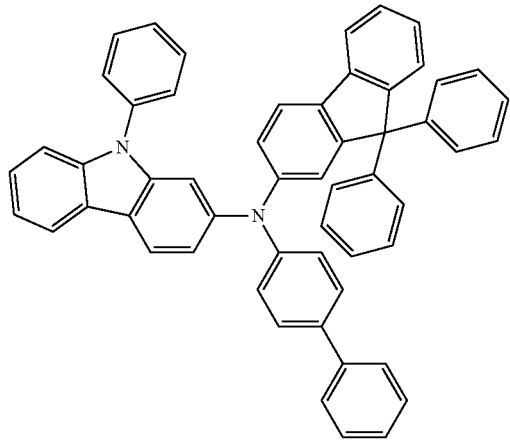
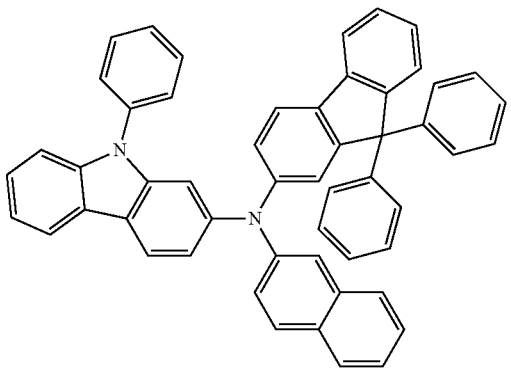
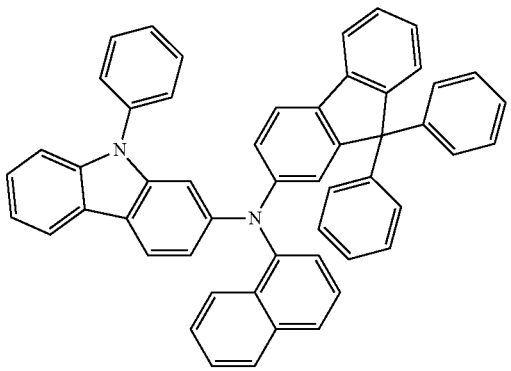
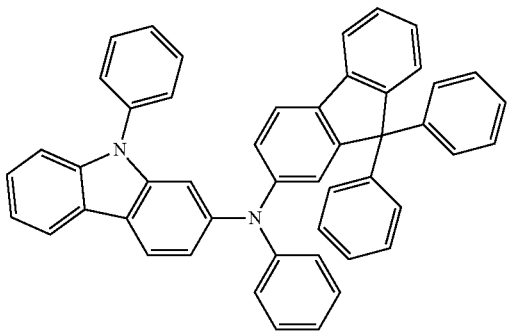
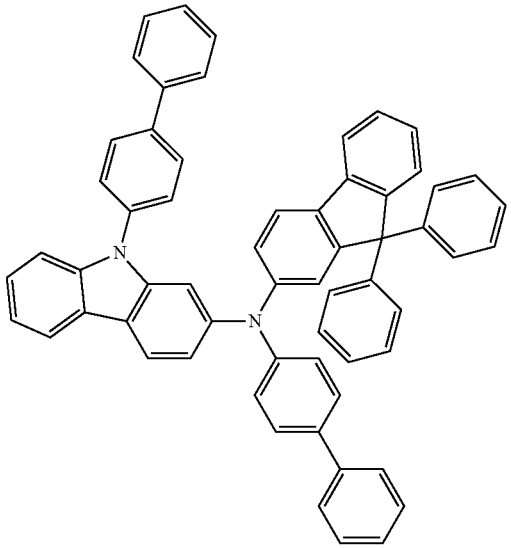

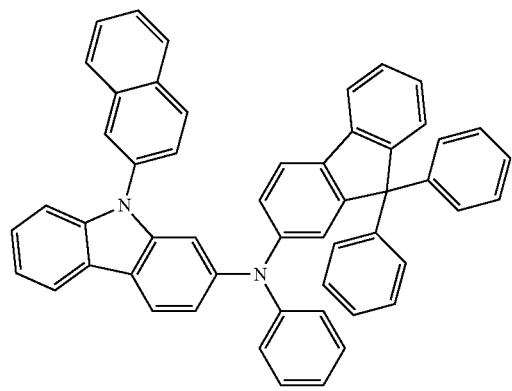
8
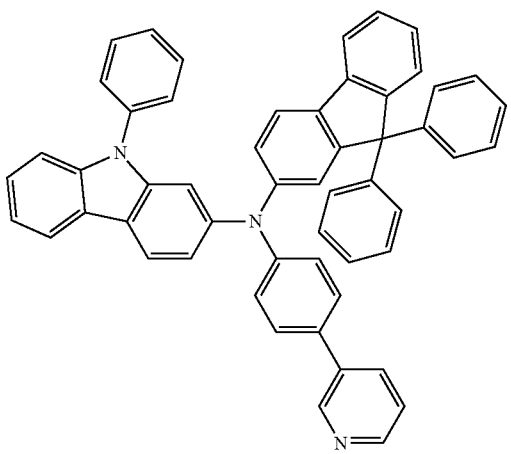
12
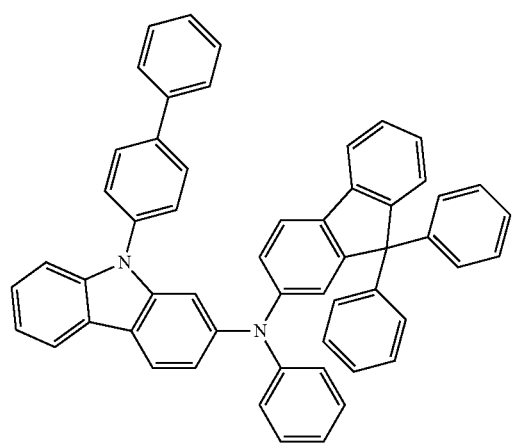
9
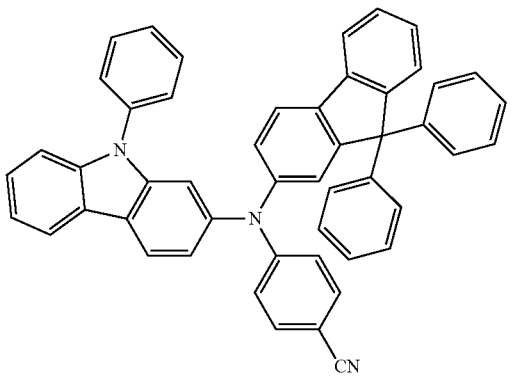
10
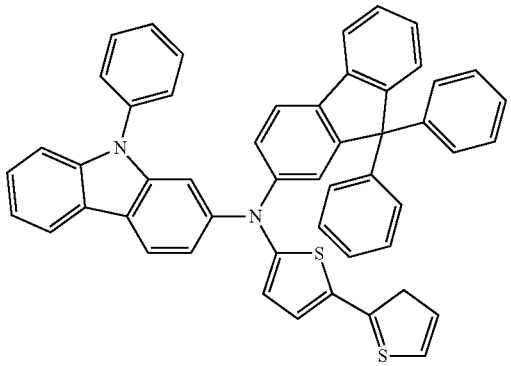
13
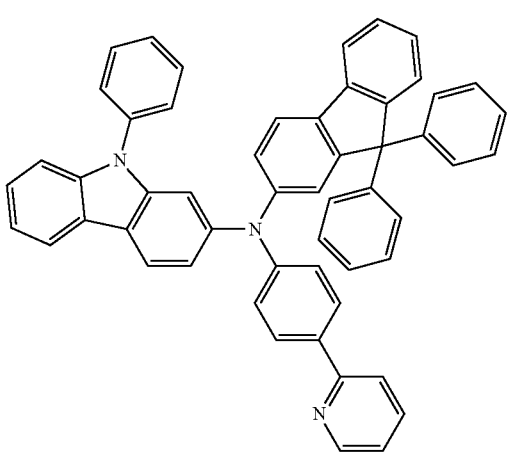
11
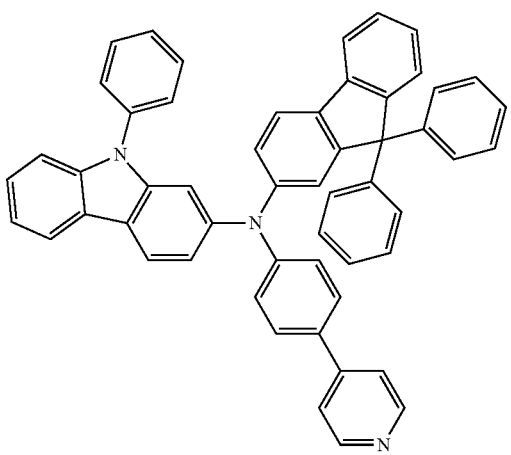
14

15
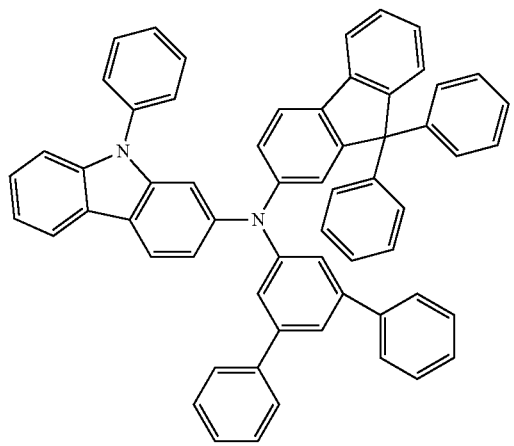
16
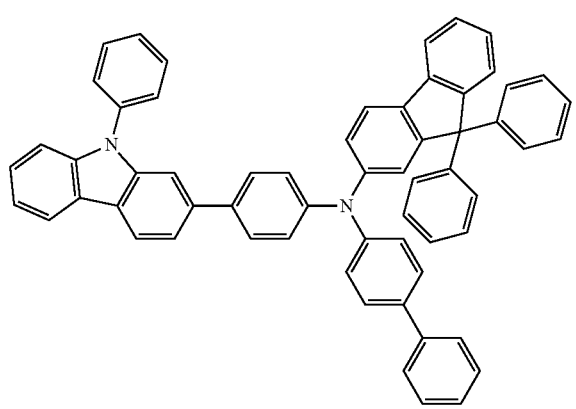
17
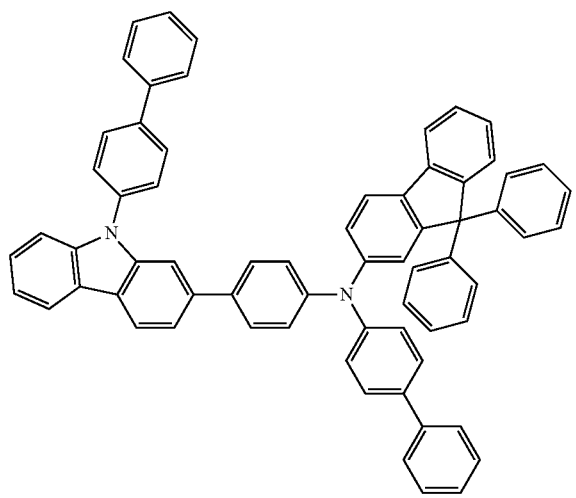
18
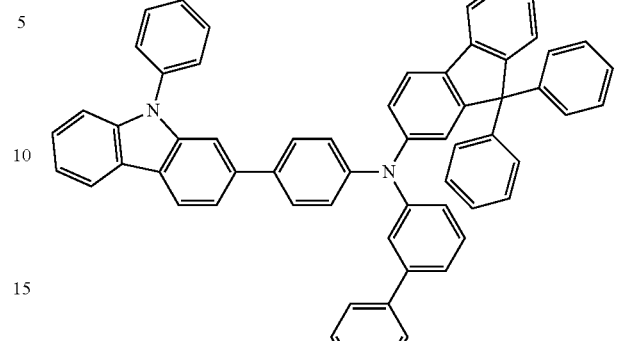
19
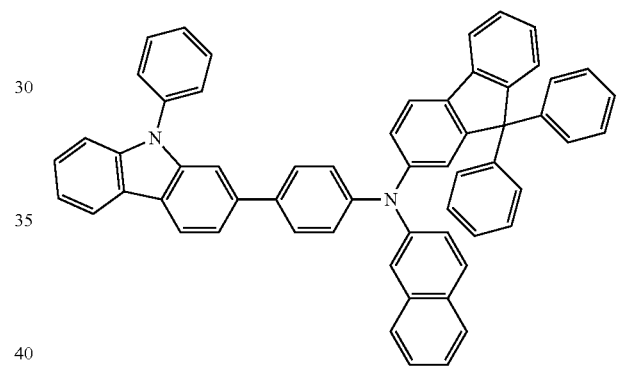
20
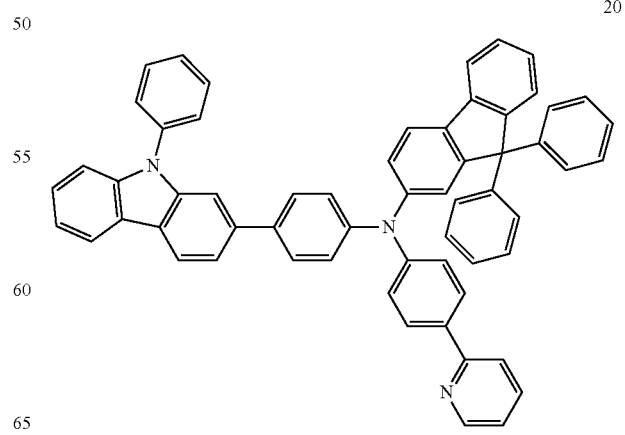

21
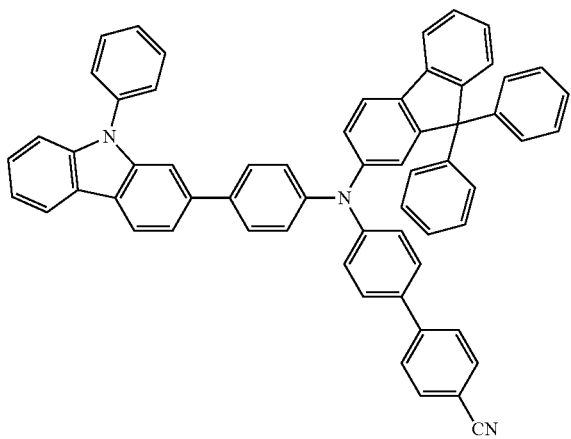
22
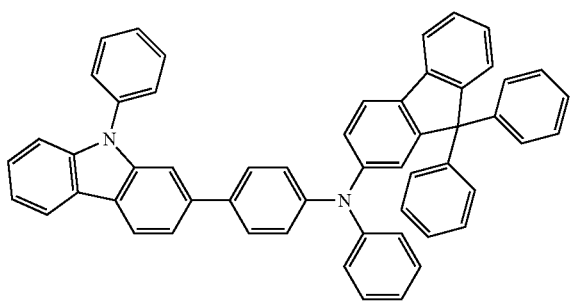
24
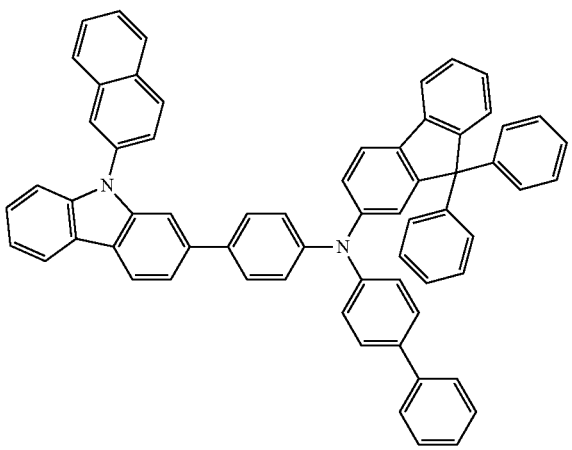
25
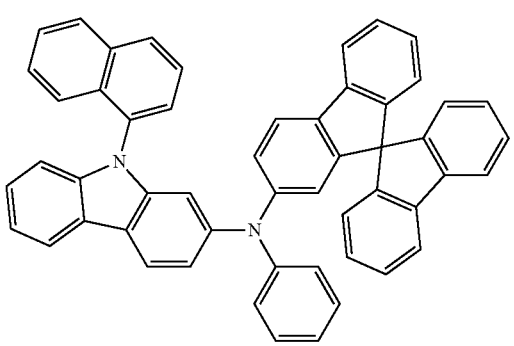

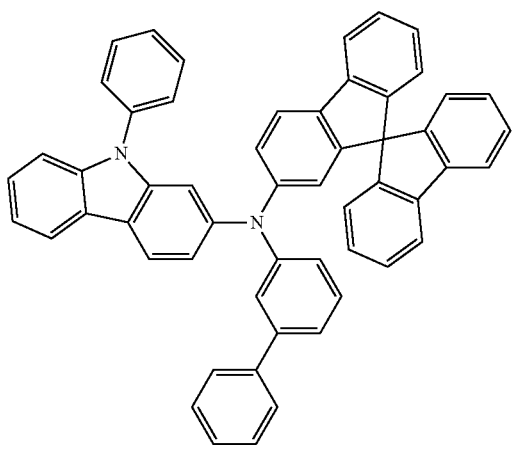
27
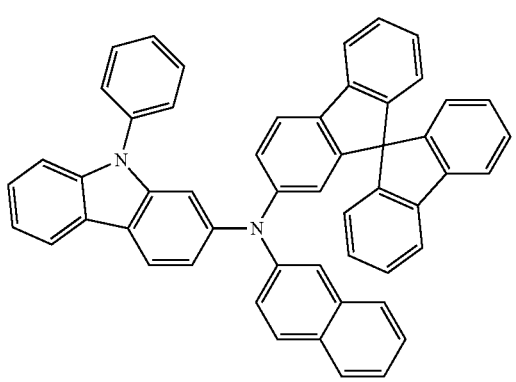
28
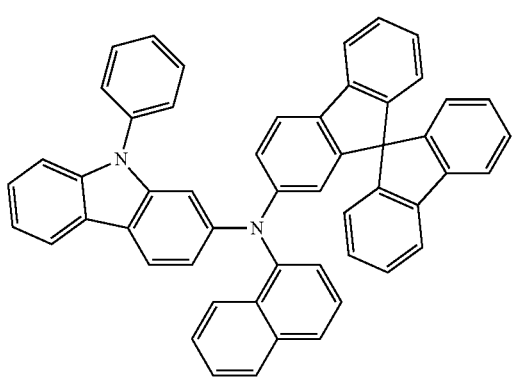
29
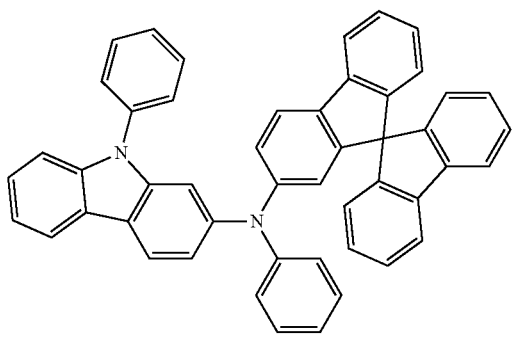
30
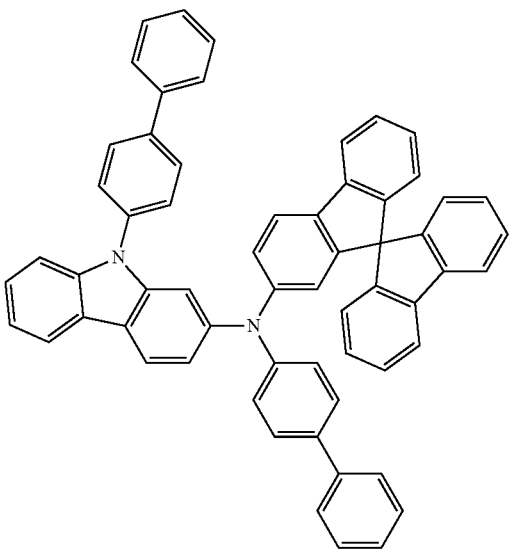
31
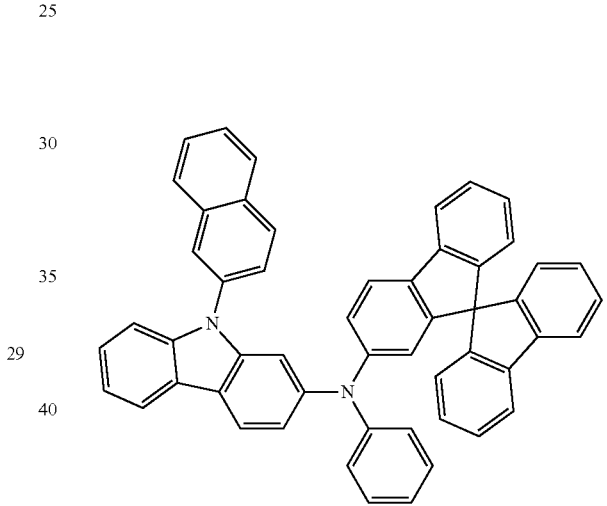
32
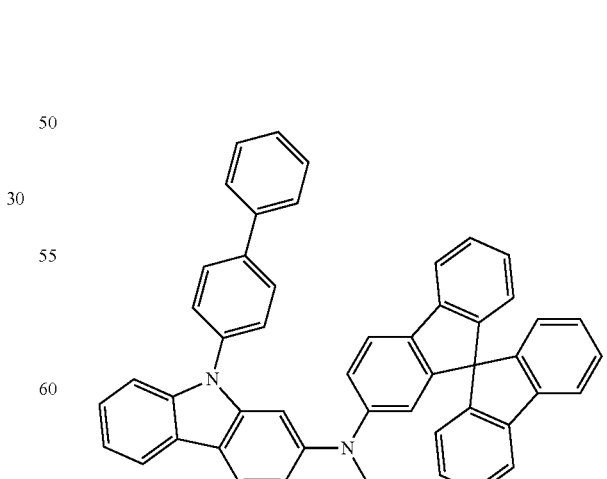
33

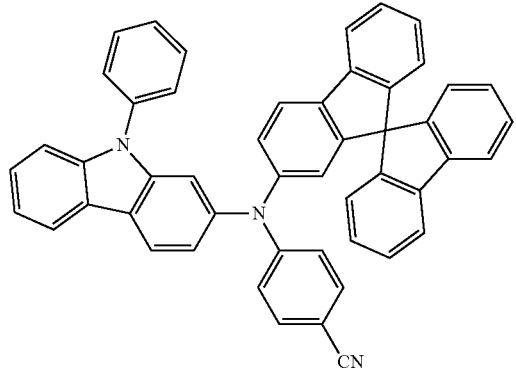
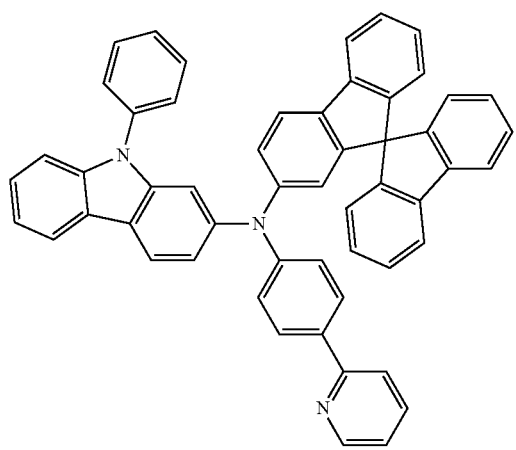
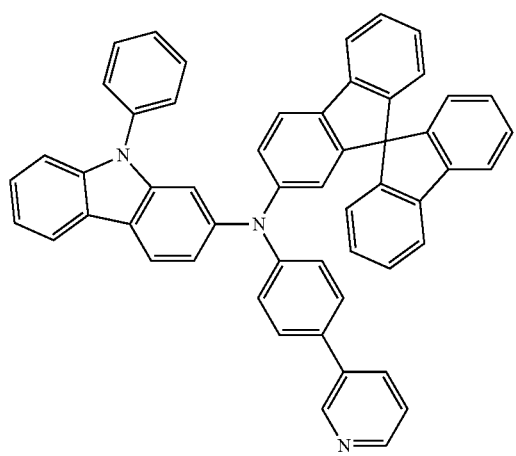
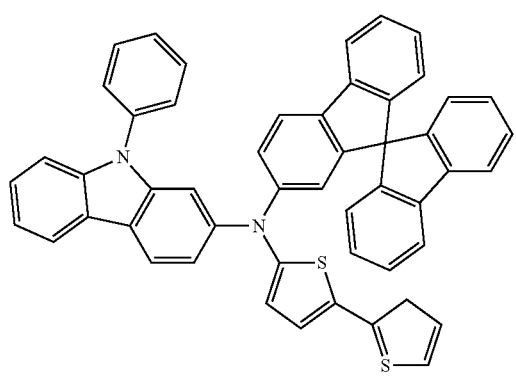
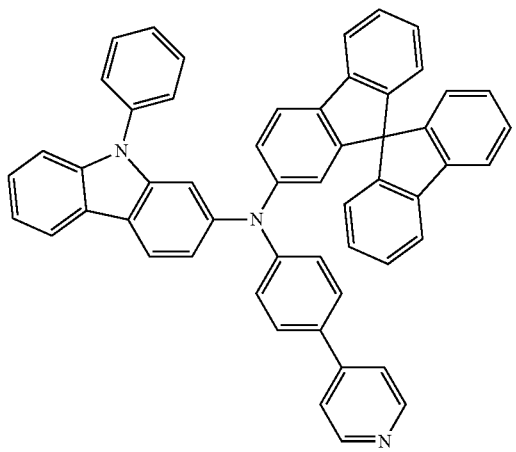
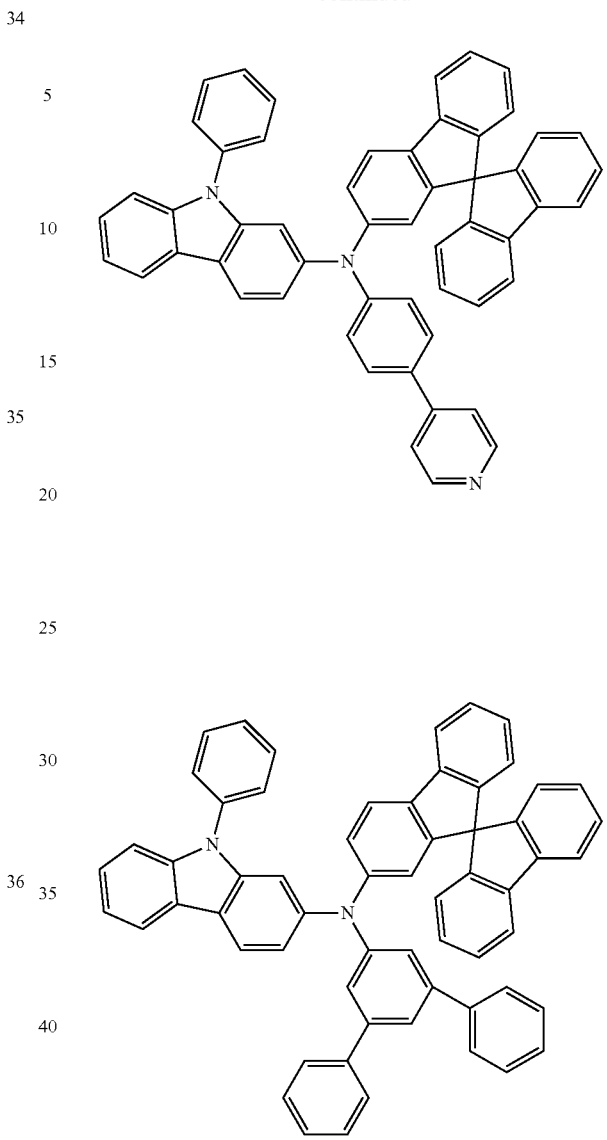
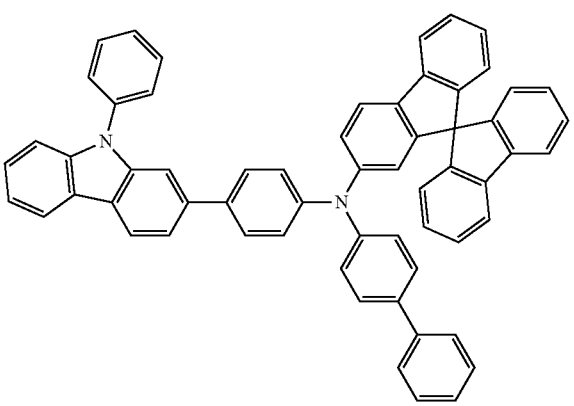

41
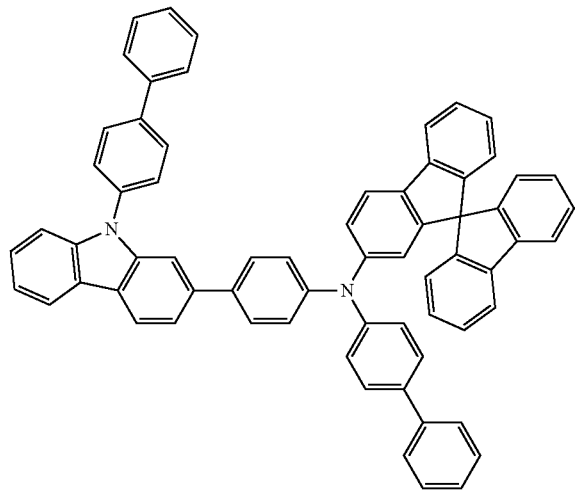
42
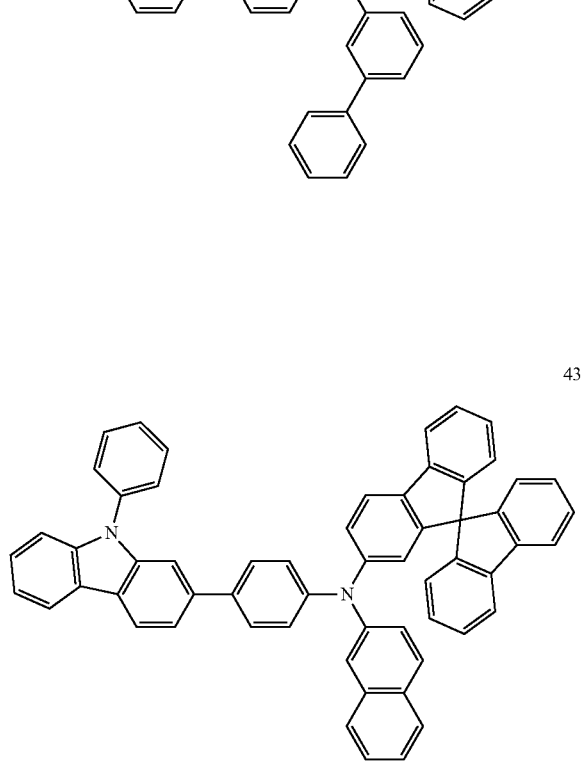
43
44
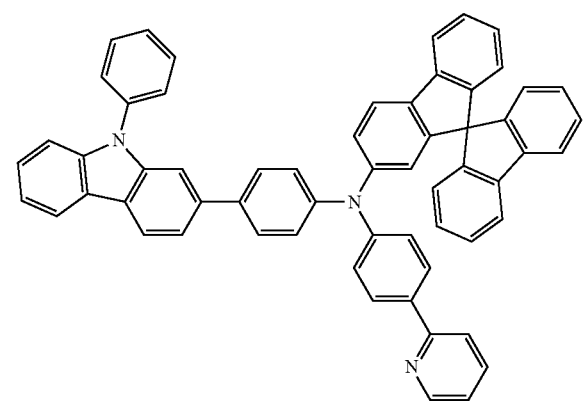
45
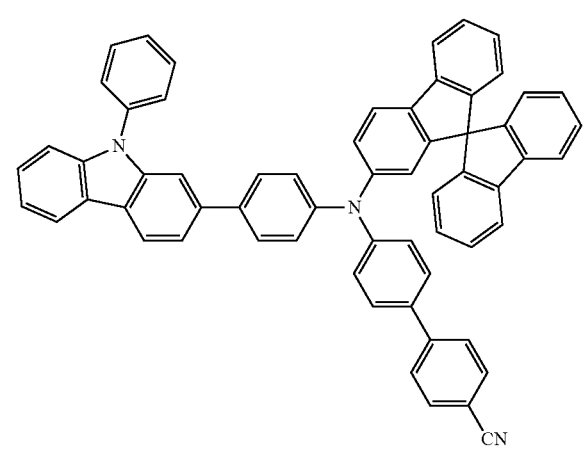
46
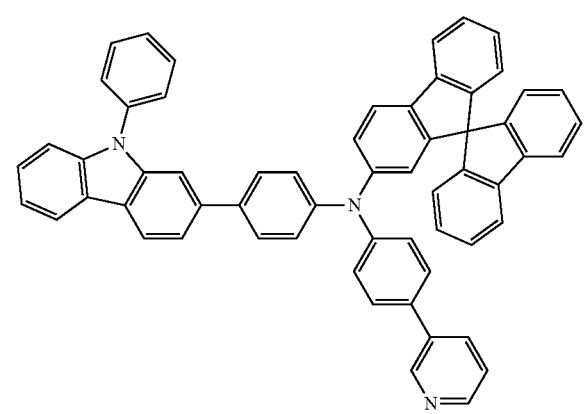
47
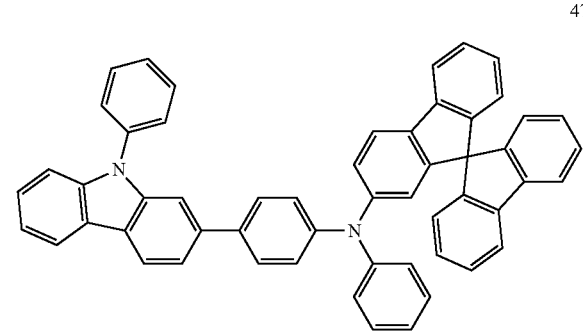

48

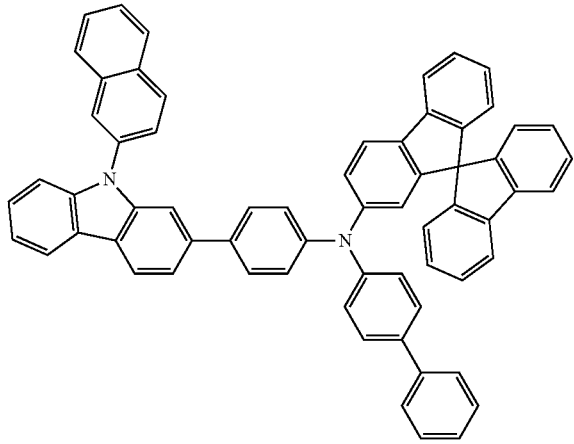

In the amine-based compound of Formula 1, the second carbon of the carbazole is linked to "N" in Formula 1 optionally, via $L_1$, so that the amine-based compound may have reduced polarity and relatively low dipole moment characteristics, as compared with a imaginary compound of which the third carbon of the carbazole is linked to "N" in Formula 1 (optionally, via $L_1$.) Since the substituents $Ar_1$ and $Ar_2$ of fluorene in the amine-based compound is an aryl group, the amine-based compound may have improved thermal stability. Accordingly, an organic light-emitting device including the amine-based compound may have a low driving voltage. Even when a layer including the amine-based compound is formed through a high-temperature process, for example, deposition, the layer may be effectively formed without denaturation of the amine-based compound.

Therefore, the organic light-emitting device including the amine-based compound of Formula 1 above may have a low driving voltage, a high efficiency, a high luminance, and long lifetime.

The amine-based compound of Formula 1 may be synthesized by a known organic synthesis method. A synthesis method of the amine-based compound of Formula 1 may be understood by those of ordinary skill in the art from the examples that will be described below.

The amine-based compound of Formula 1 may be used between a pair of electrodes of the organic light-emitting device. For example, the amine-based compound of Formula 1 may be used in at least one of a hole injection layer, a hole transport layer, and a functional layer having both hole injection and hole transporting capabilities.

According to another aspect of the present embodiments, an organic light-emitting device includes a first electrode, a second electrode disposed opposite to the first electrode, and an organic layer disposed between the first electrode and the second electrode, wherein the first layer includes at least one of the amine-based compounds of Formula 1 described above.

As used herein, "(for example, the organic layer) including at least one amine-based compound" means "(the organic layer) including one of the amine-based compounds of Formula 1 above, or at least two different amine-based compounds of Formula 1 above".

In some embodiments, the organic layer may include only Compound 1 above as the amine-based compound. In this regard, the Compound 1 may be present in the hole transport layer of the organic light-emitting device. In some embodiments, the organic layer may include Compounds 1 and 2 as the amine-based compound. In this regard, the Compounds 1 and 2 may be present in the same layer (for example, in the electron transport layer) or may be present in different layers (for example, in the hole transport layer and the emission layer, respectively).

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

The term "organic layer" as used herein refers to a single layer and/or a plurality of layers disposed between the first and second electrodes of the organic light-emitting device.

The organic layer may include at least one of a hole injection layer, a hole transport layer, and a functional layer having both hole injection and hole transport capabilities, and the amine-based compound may be in the at least one of the hole injection layer, the hole transport layer, and the functional layer having both hole injection and hole transport capabilities.

FIG. 1 is a schematic sectional view of an organic light-emitting device 10 according to an embodiment. Hereinafter, a structure of an organic light-emitting device according to an embodiment and a method of manufacturing the same will now be described with reference to FIG. 1.

The substrate 11 may be any substrate that is used in existing organic light-emitting devices. In some embodiments the substrate 11 may be a glass substrate or a transparent plastic substrate with strong mechanical strength, thermal stability, transparency, surface smoothness, ease of handling, and water resistance.

The first electrode 13 may be formed by depositing or sputtering a first electrode-forming material on the substrate. When the first electrode 13 is an anode, a material having a high work function may be used as the first electrode-forming material to facilitate hole injection. The first electrode 13 may be a reflective electrode or a transmission electrode. A first electrode material maybe a transparent material with high conductivity, for example, indium tin oxide (ITO), indium zinc oxide (IZO), tin oxide ($SnO_2$), or zinc oxide (ZnO). In some other embodiments, the first electrode 13 may be formed as a reflective electrode using magnesium (Mg), aluminum (Al), aluminum-lithium (Al—Li), calcium (Ca), magnesium-indium (Mg—In), or magnesium-silver (Mg—Ag).

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a hole injection layer (HIL), a hole transport layer (HTL), a buffer layer, an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may comprise any material that is commonly used to form a HIL. Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate (PANI/PSS).

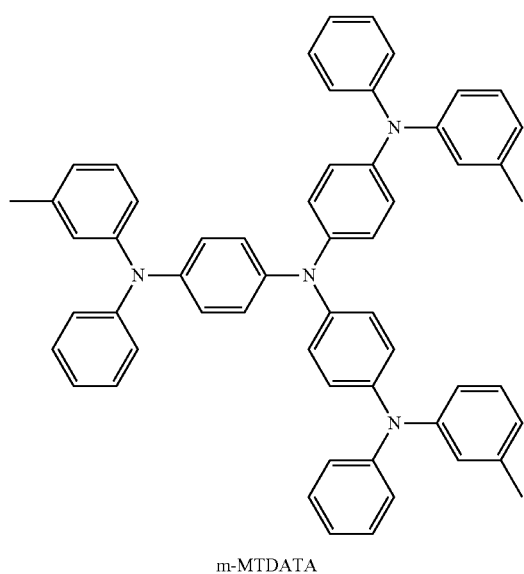

m-MTDATA

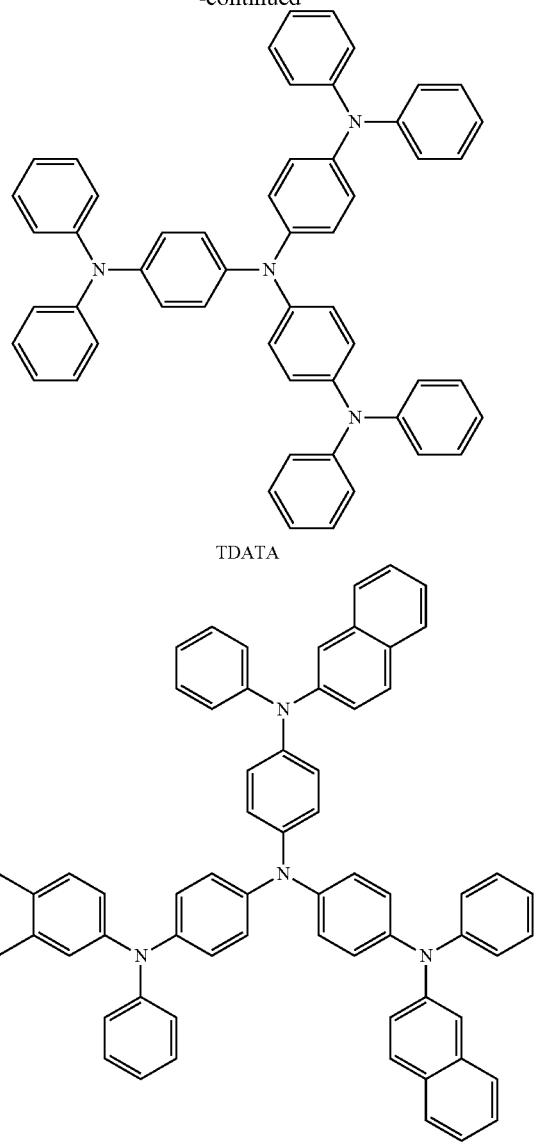

TDATA

2-TNATA

For example, the HIL may include the amine-based compound of Formula 1 above, but is not limited thereto.

The thickness of the HIL may be from about 100 Å to about 10000 Å, and in some embodiments, from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

Non-limiting examples of suitable known HTL forming materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N- carbazolyl)triphenylamine (TCTA), and N,N'-di(1-naphthyl)-N,N'-diphenylbenzidine) (NPB).

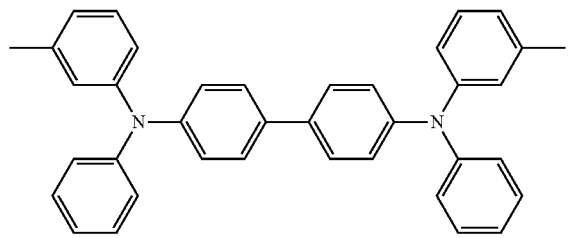

TPD

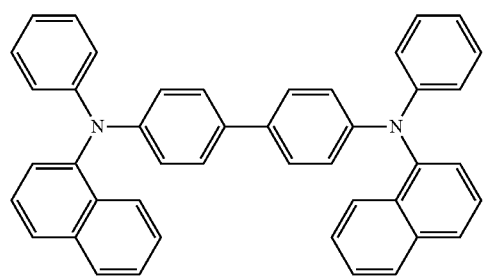

NPB

For example, the HTL may include the amine-based compound of Formula 1 above, but is not limited thereto.

The thickness of the HTL may be about 50 Å to about 1000 Å, and for example, about 100 Å to about 800 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer has good hole injection and transport capabilities without a substantial increase in driving voltage.

For example, the H-functional layer may include the amine-based compound of Formula 1 above, but is not limited thereto.

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

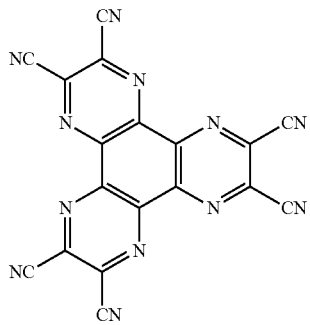

<Compound 200>

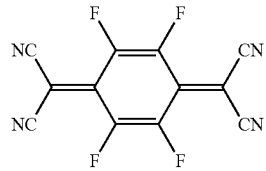

<F4-TCNQ>

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any hole injecting material or hole transporting material that are widely known. In some other embodiments, the buffer layer may include the same material as one of the materials included in the HIL, HTL, and H-functional layer that underly the buffer layer.

An EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The emission layer may include a host and a dopant. For example, the dopant may include a fluorescent dopant and/or a phosphorescent dopant. In some embodiments, the phosphorescent dopant may be an organic metal compound including at least one element of iridium (Ir), platinum (Pt), osmium (Os), titanium (Ti), zirconium (Zr), hafnium (Hf), europium (Eu), terbium (Tb) and thulium (Tm).

When the organic light-emitting device is a full color organic light-emitting device, the emission layer may be patterned into a red emission layer, a green emission layer, and a blue emission layer. In some embodiments, the emission layer may include at least two of the red emission layer, the green emission layer and/or the blue emission layer that are stacked upon one another, and thus may emit white light, but is not limited thereto.

At least one of the red EML, the green EML, and the blue EML may include a dopant below (ppy=phenylpyridine).

Non-limiting examples of the blue dopant are compounds represented by the following formulae.

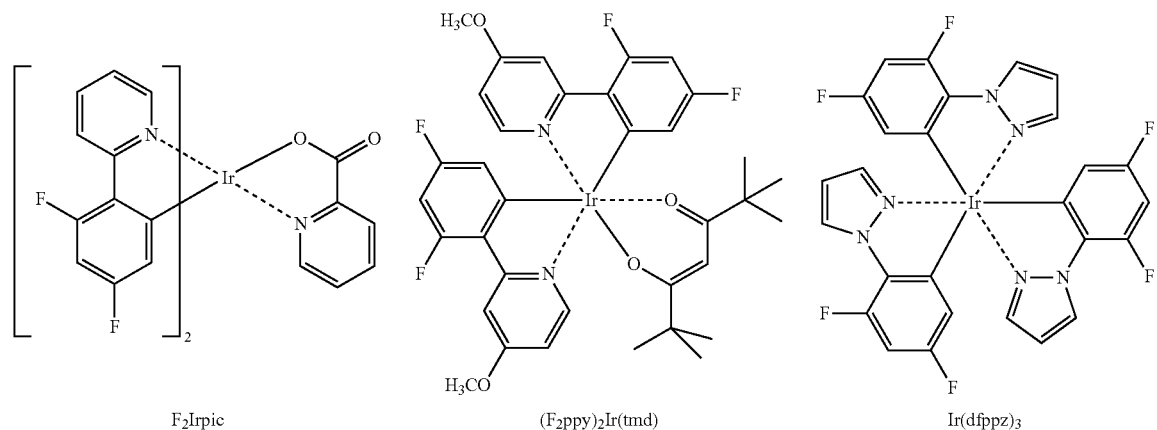
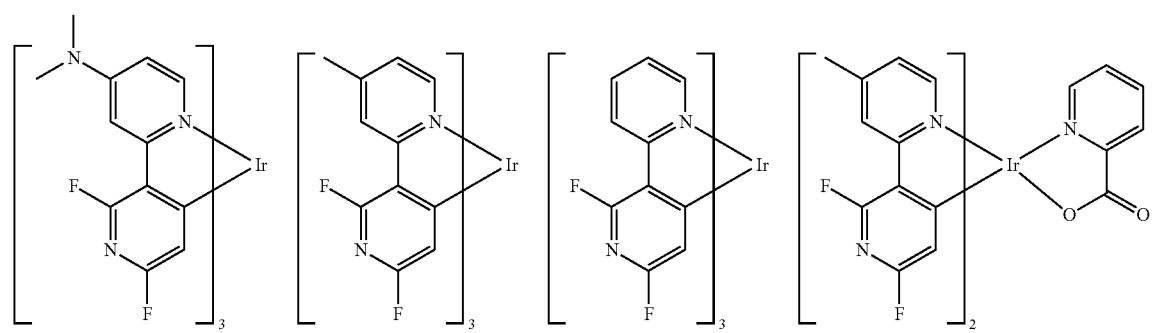
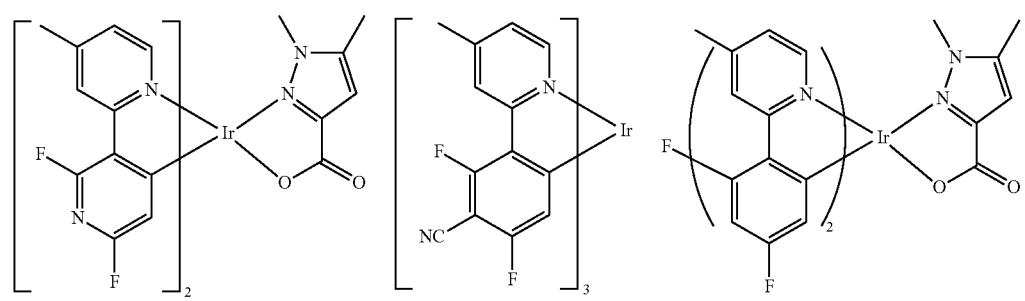
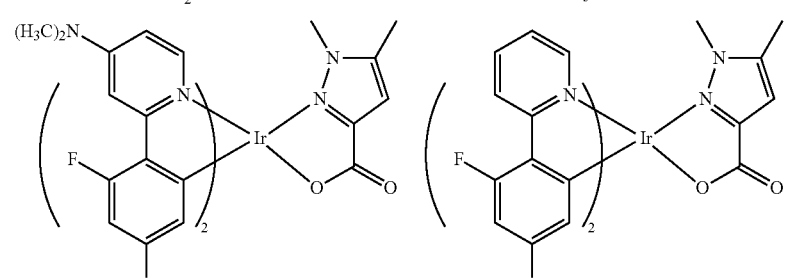
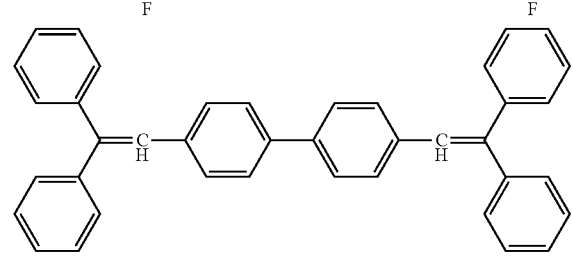

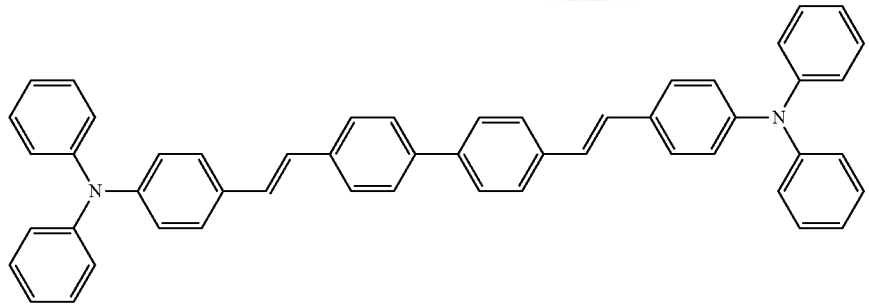
DPAVBi
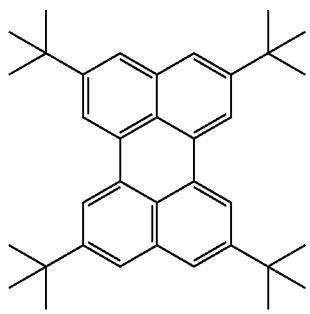
TBPe
Non-limiting examples of the red dopant are compounds represented by the following formulae. In some embodiments, the red dopant may be DCM or DCJTB, which will be described later.
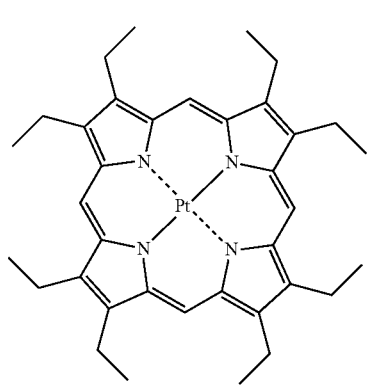
PtOEP
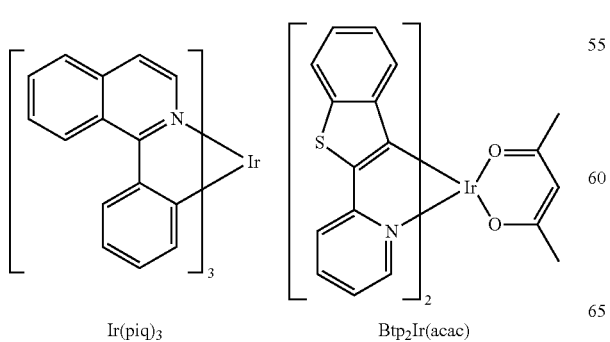
Ir(piq)₃    Btp₂Ir(acac)
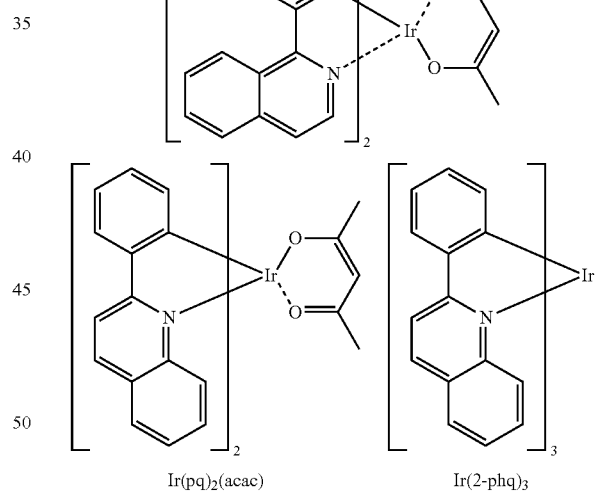
Ir(pq)₂(acac)    Ir(2-phq)₃
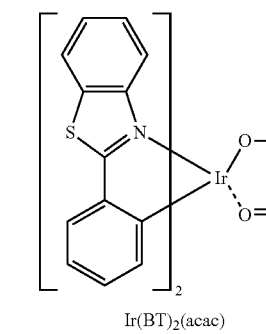
Ir(BT)₂(acac)

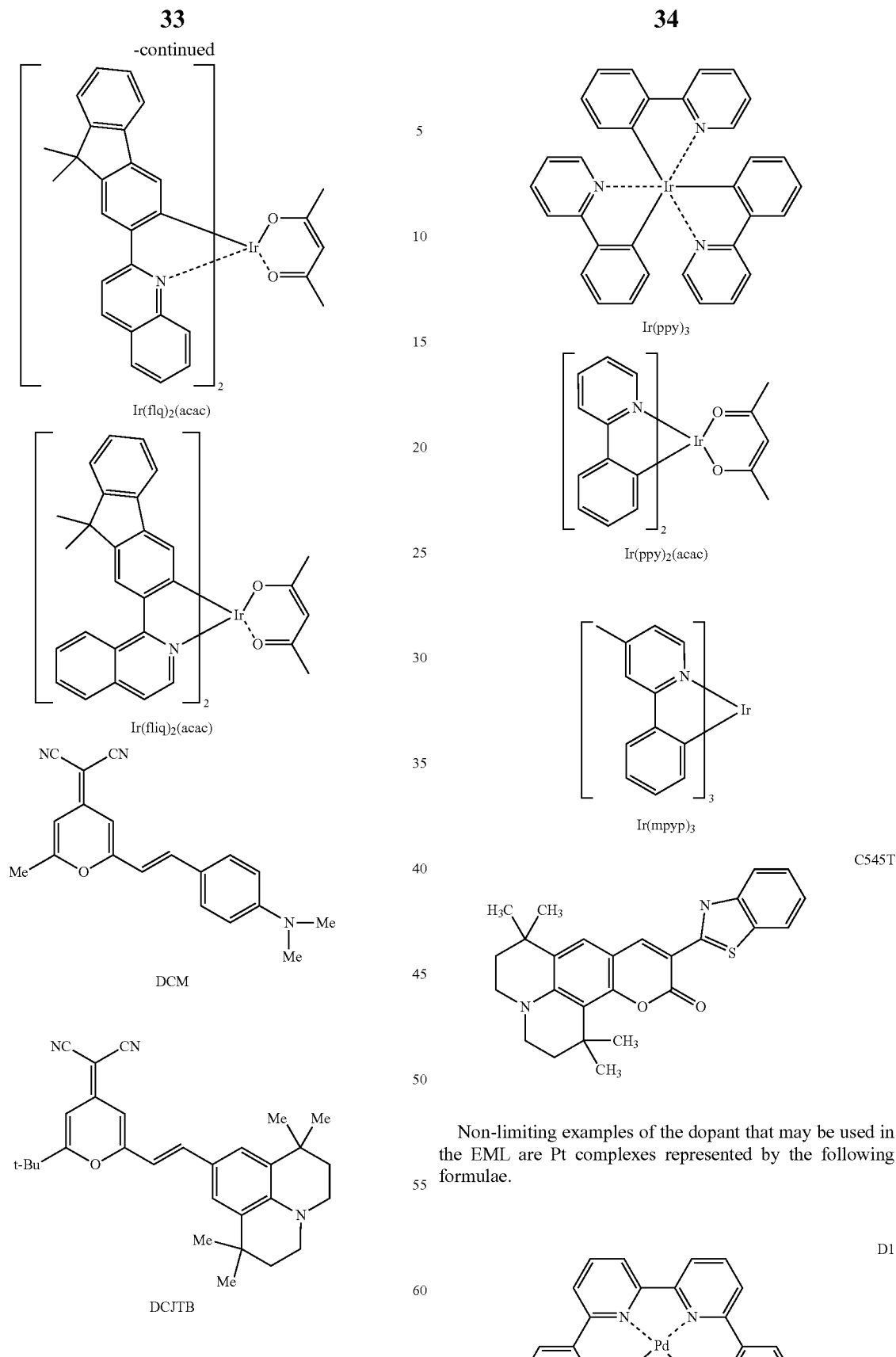
Non-limiting examples of the green dopant are compounds represented by the following formulae. In an embodiment, the green dopant may be C545T represented below.
Non-limiting examples of the dopant that may be used in the EML are Pt complexes represented by the following formulae.
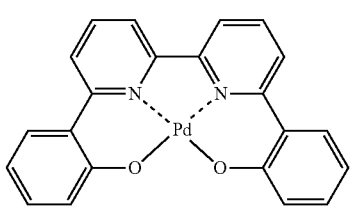

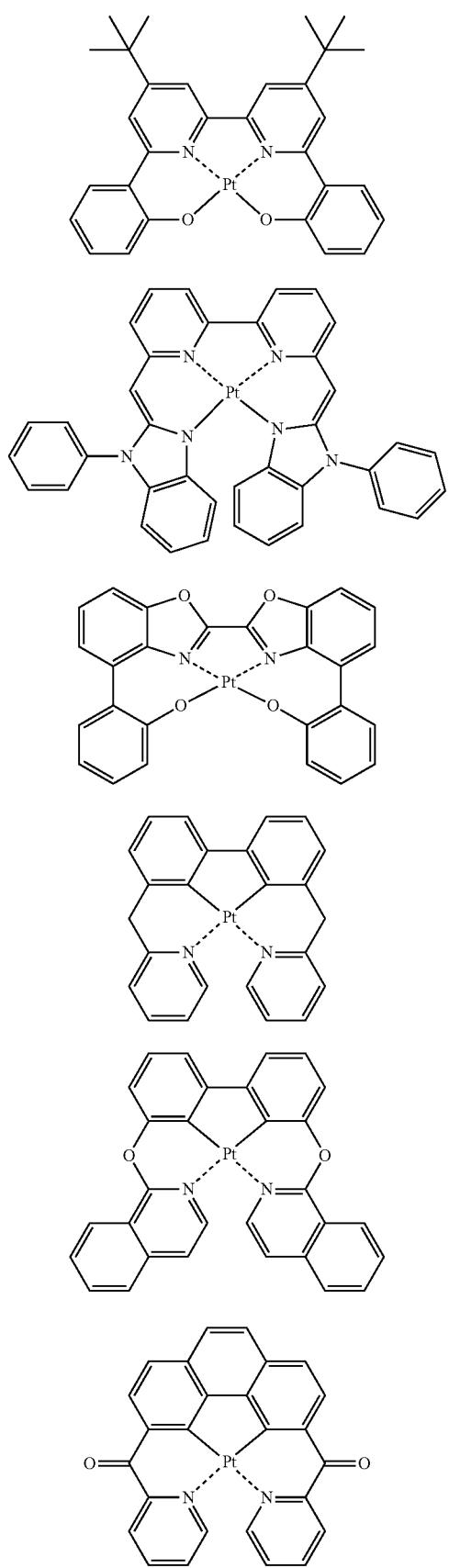
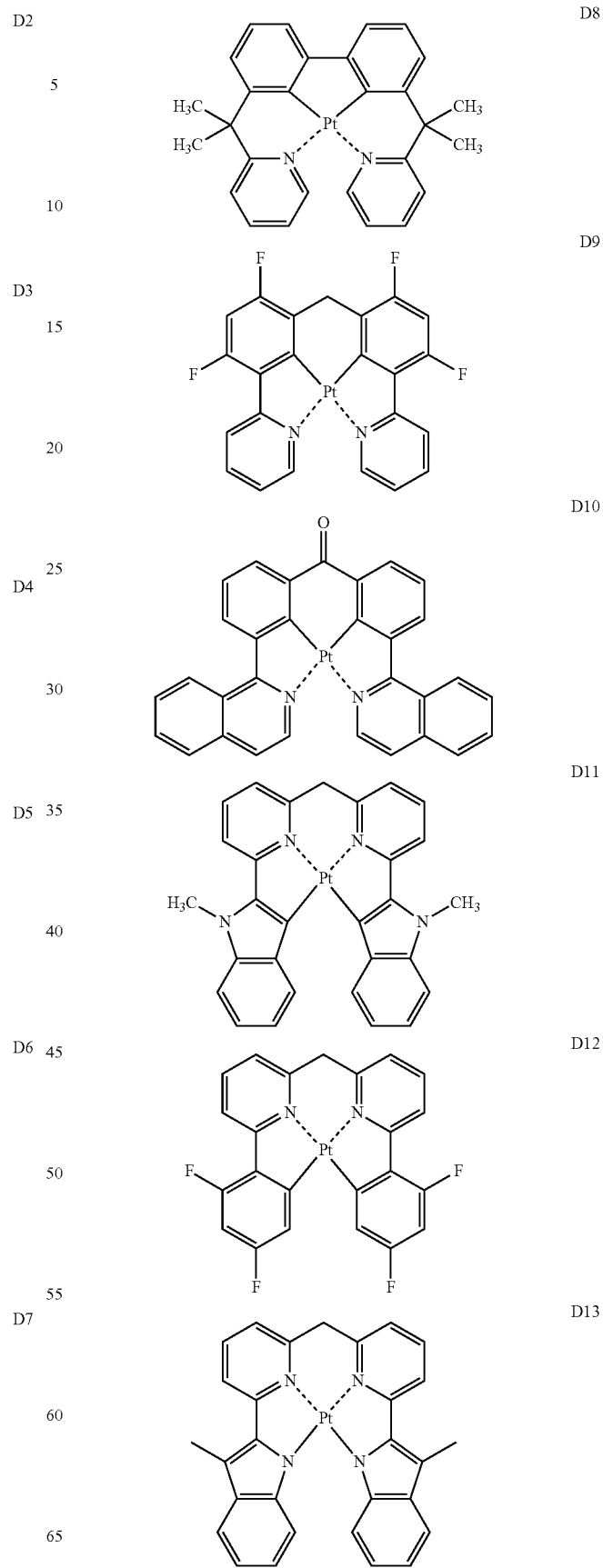

-continued
D14
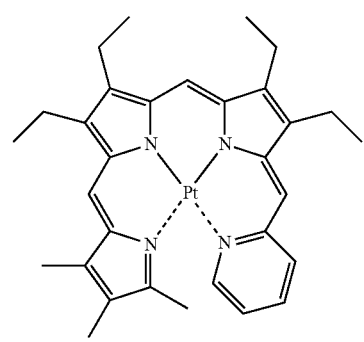
D15
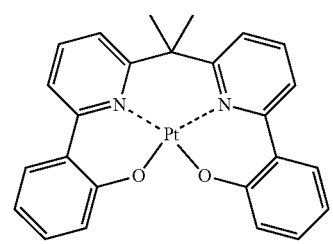
D16
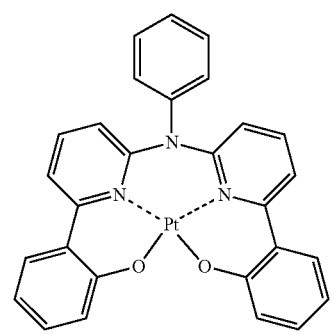
D17
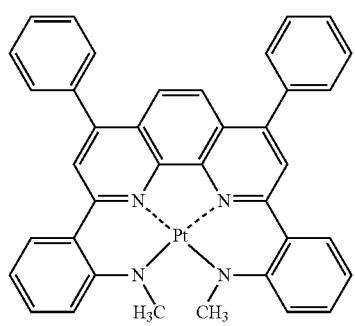
D18
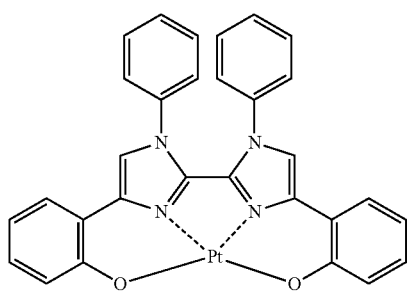
-continued
D19
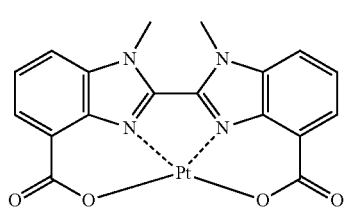
D20
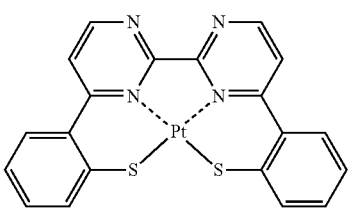
D21
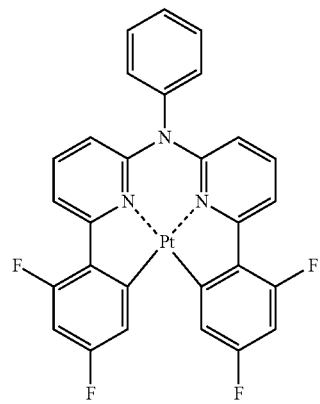
D22
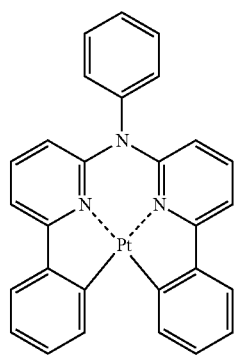
D23
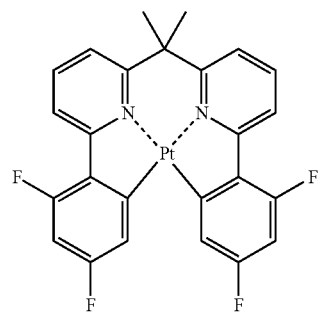

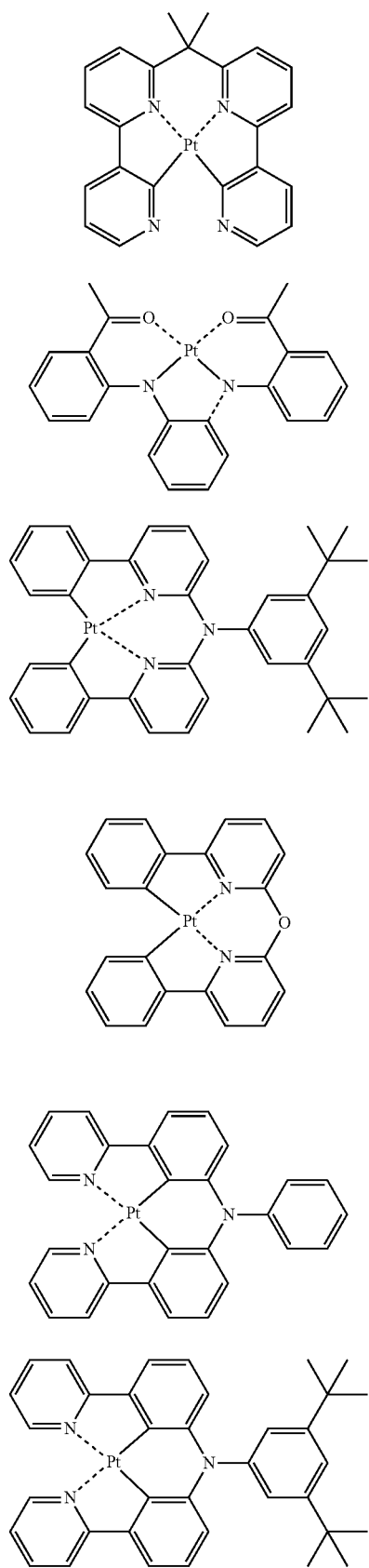
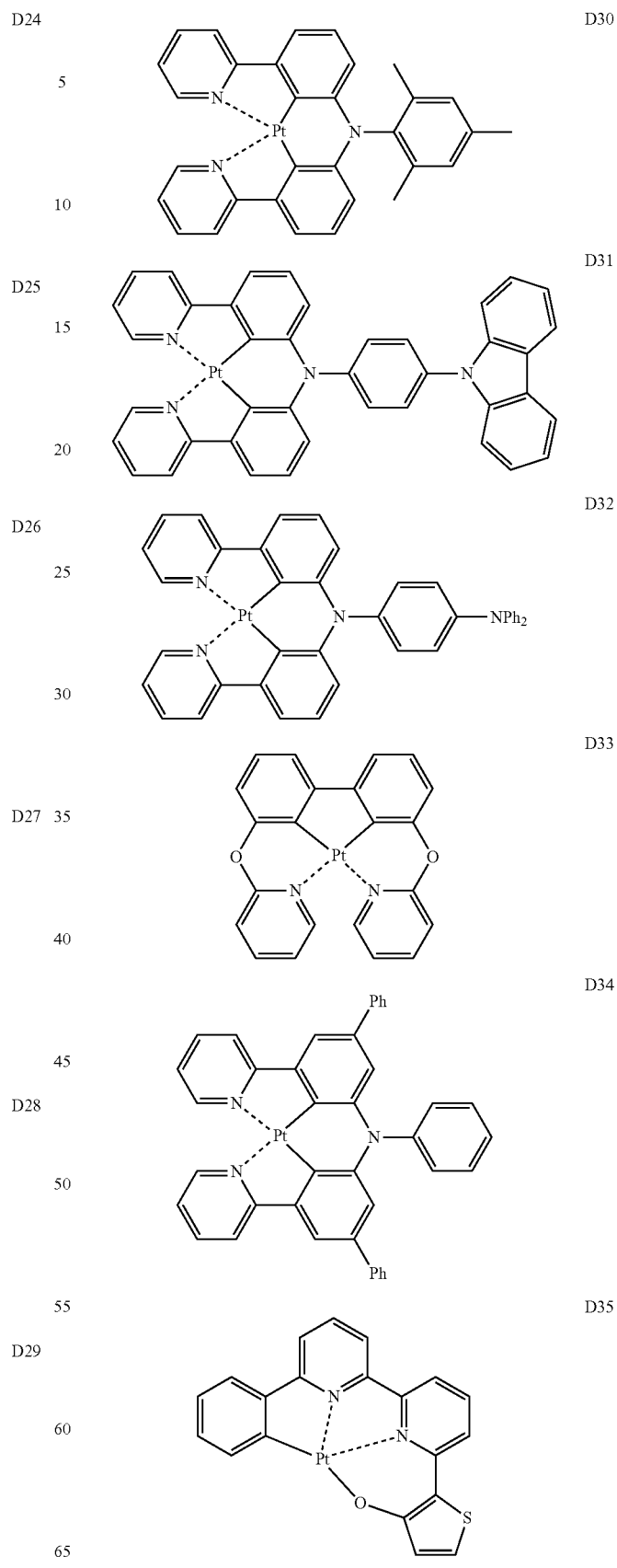

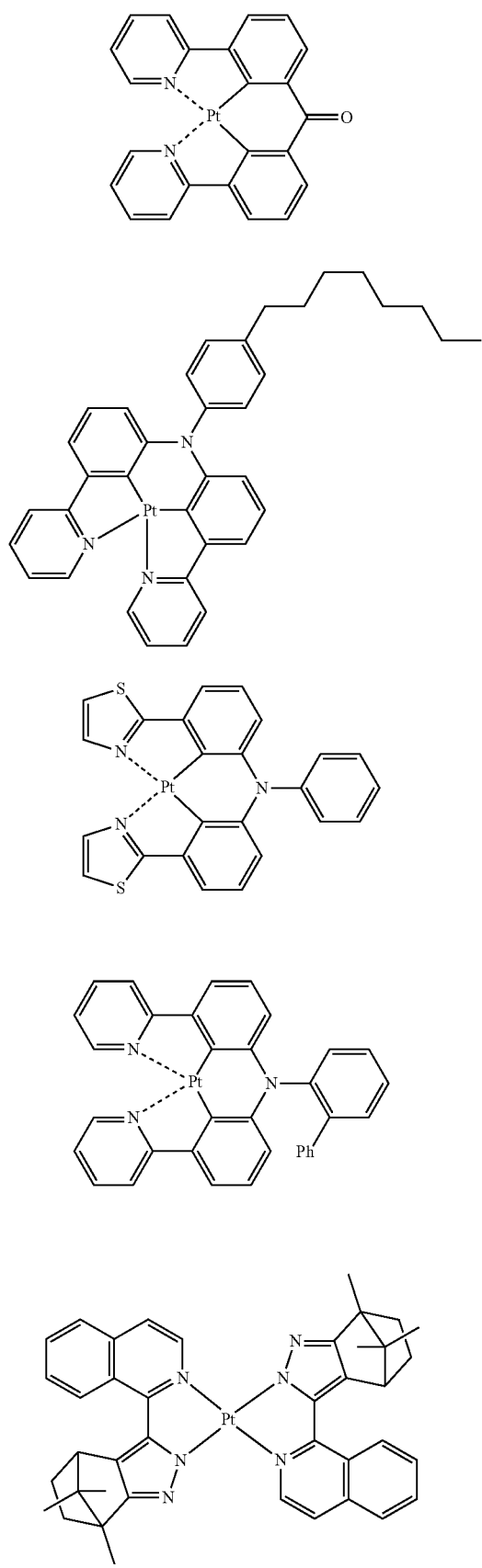
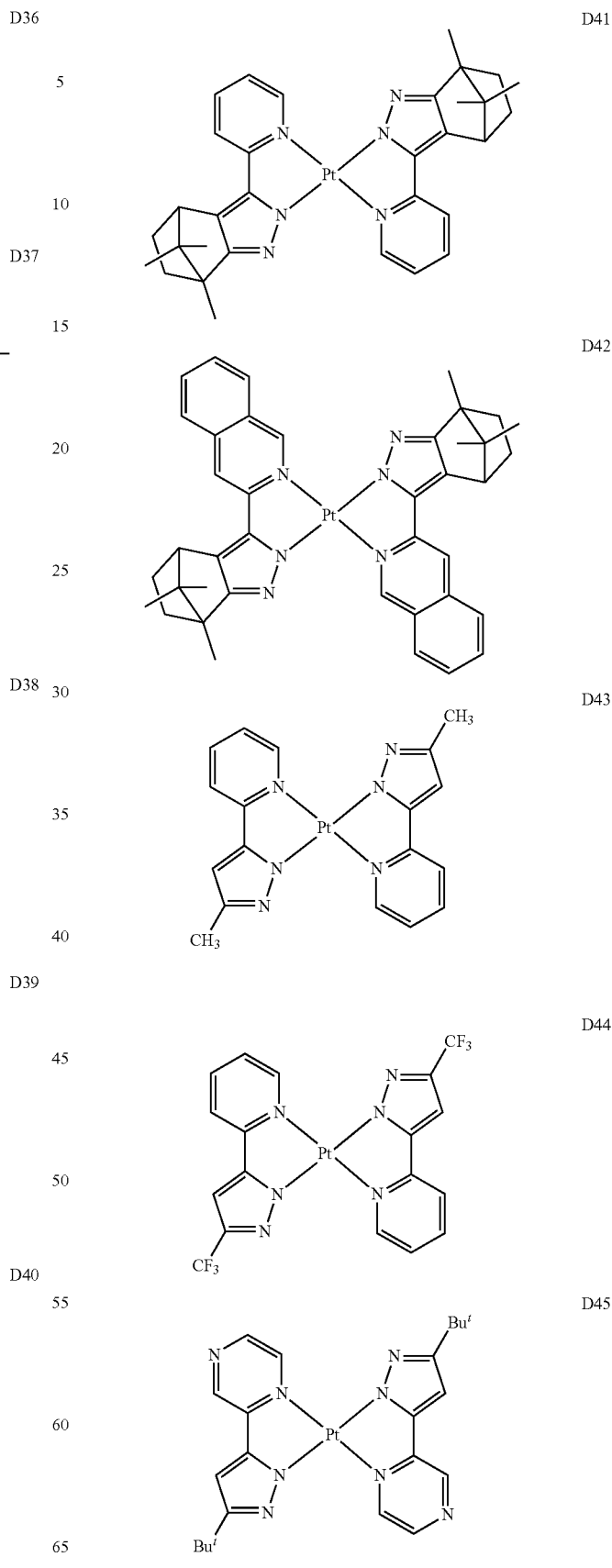

-continued

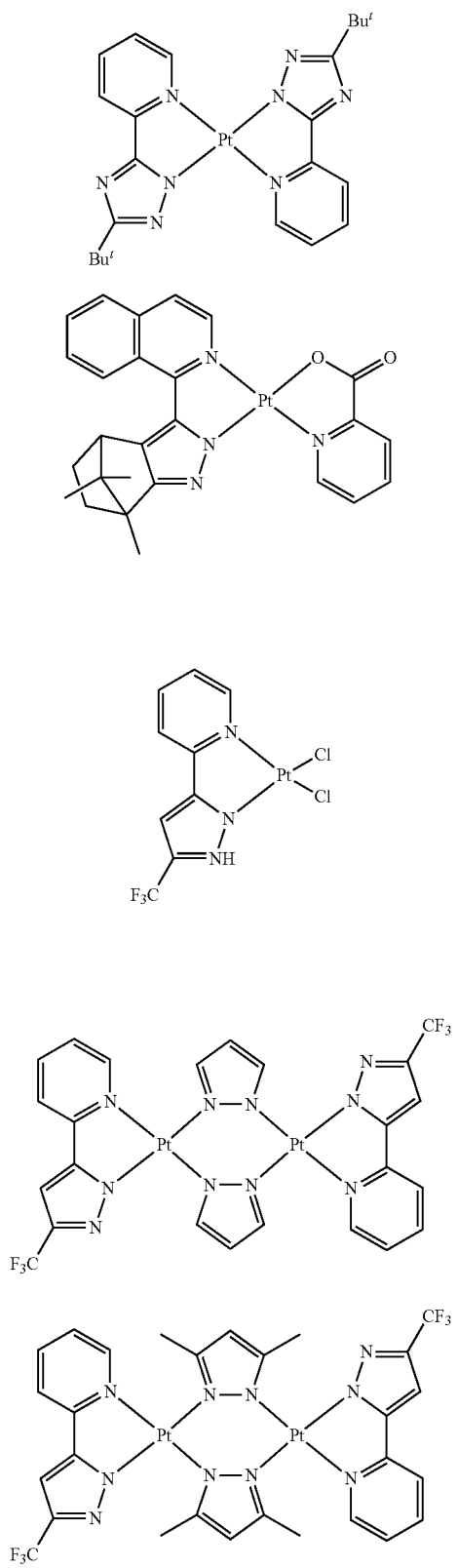

D46

D47

D48

D49

D50

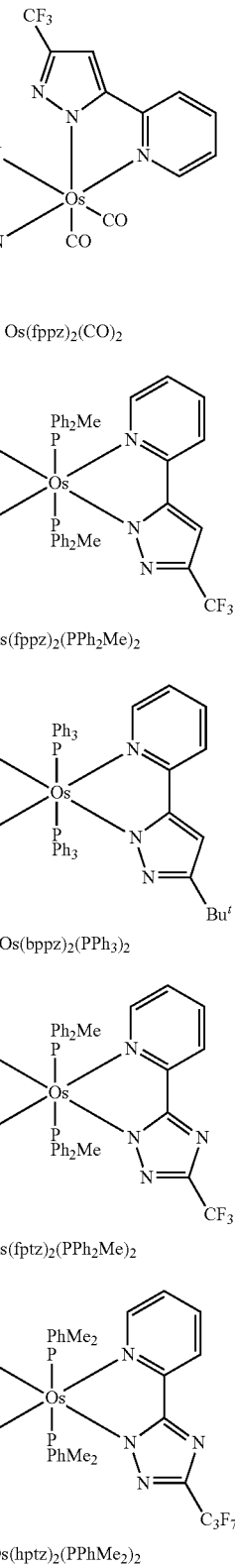

Os(fppz)₂(CO)₂

Os(fppz)₂(PPh₂Me)₂

Os(bppz)₂(PPh₃)₂

Os(fptz)₂(PPh₂Me)₂

Os(hptz)₂(PPhMe₂)₂

Non-limiting examples of the dopant that may be used in the EML are Os complexes represented by the following formulae.

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may be any material that can stably transport electrons injected from an electron injecting electrode (cathode). Non-limiting examples of materials for forming the ETL are a quinoline derivative, such as tris(8-quinolinorate)aluminum (Alq3), TAZ, BAlq, beryllium bis(benzoquinolin-10-olate) (Bebq$_2$), 9,10-di(naphthalene-2-yl)anthracene (ADN), Compound 201, and Compound 202, but are not limited thereto.

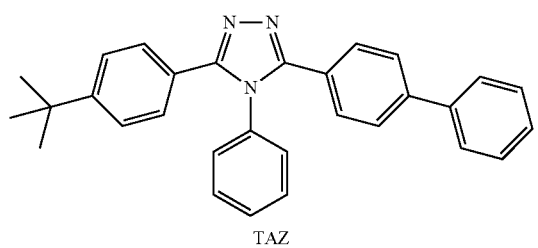

TAZ

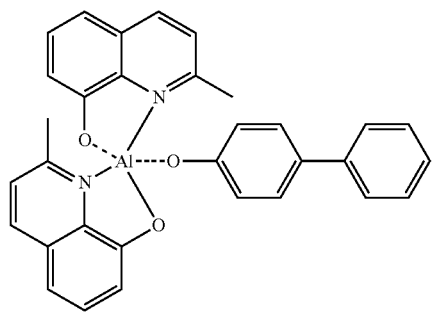

BAlq

<Compound 201>

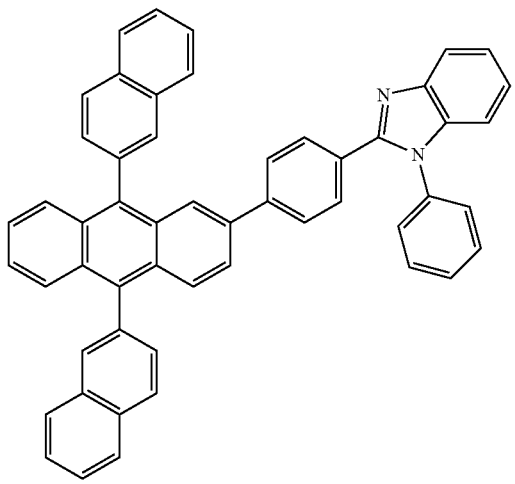

<Compound 202>

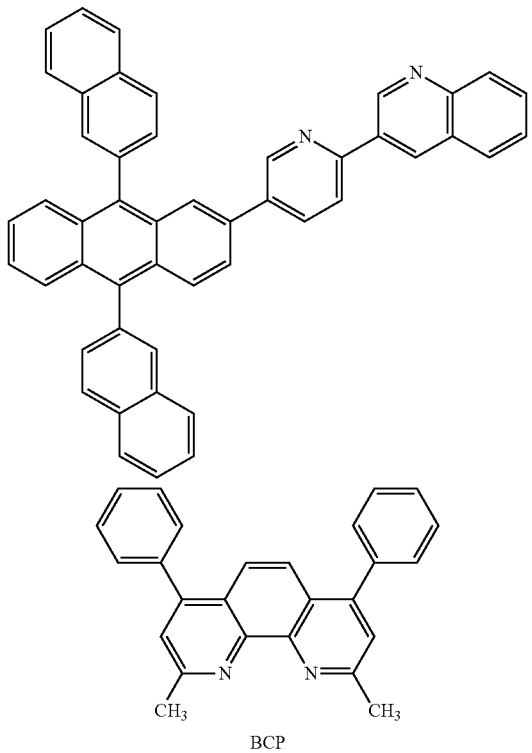

BCP

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to any known electron-transporting organic compound.

The metal-containing material may include a lithium (Li) complex. Non-limiting examples of the Li complex are lithium quinolate (LiQ) and Compound 203 below:

<Compound 203>

<LiQ>

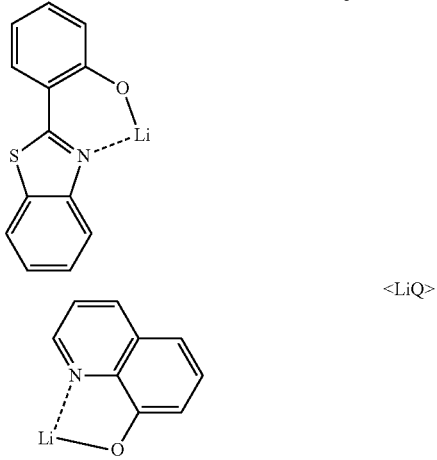

Then, an EIL, which facilitates injection of electrons from the cathode, may be formed on the ETL. Any suitable electron-injecting material may be used to form the EIL.

Then, an EIL, which facilitates injection of electrons from the cathode, may be formed on the ETL. Any suitable electron-injecting material may be used to form the EIL.

Non-limiting examples of materials for forming the EIL are LiF, NaCl, CsF, $Li_2O$, and BaO, which are known in the art. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

The second electrode 17 is disposed on the organic layer 15. The second electrode 17 may be a cathode that is an electron injection electrode. A material for forming the second electrode 17 may be a metal, an alloy, an electro-conductive compound, which have a low work function, or a mixture thereof. In some embodiments, the second electrode 190 as a transmission electrode may be formed using a thin film of Li, Mg, Al, Al—Li, Ca, Mg—In, Mg—Ag, or the like. In some embodiments, to manufacture a top-emission light-emitting device, the transmission electrode may comprise indium tin oxide (ITO) or indium zinc oxide (IZO).

Although the organic light-emitting device of FIG. 1 is described above, the present embodiments are not limited thereto.

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, bathocuproine (BCP) represented by the following formula may be used as a material for forming the HBL.

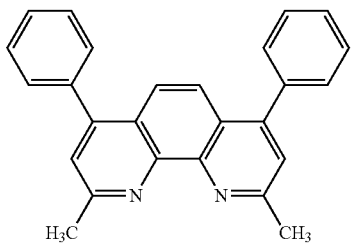

BCP

The thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

Hereinafter, the present embodiments will be described in detail with reference to the following synthesis examples and other examples. However, these examples are for illustrative purposes only and are not intended to limit the scope of the present embodiments.

As used herein, examples of the unsubstituted $C_1$-$C_{60}$ alkyl group (or $C_1$-$C_{60}$ alkyl group) are linear of branched $C_1$-$C_{60}$ alkyl groups, such as methyl, ethyl, propyl, isobutyl, sec-butyl, pentyl, iso-amyl, or hexyl. Examples of the substituted $C_1$-$C_{60}$ alkyl group are the unsubstituted $C_1$-$C_{60}$ alkyl group of which at least one hydrogen atom is substituted with one of a deuterium atom, a halogen atom, a hydroxy group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —$N(Q_{11})(Q_{12})$, and —$Si(Q_{13})(Q_{14})(Q_{15})$ (where $Q_{11}$ to $Q_{15}$ are each independently selected from the group consisting of a hydrogen atom, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group).

As used herein, the unsubstituted $C_1$-$C_{60}$ alkoxy group (or $C_1$-$C_{60}$ alkoxy group) may be represented by the formula of —OA (wherein A is an unsubstituted $C_1$-$C_{60}$ alkyl group as described above). Examples of the unsubstituted $C_1$-$C_{60}$ alkoxy group are methoxy, ethoxy, and isopropyloxy groups. At least one hydrogen atom of the unsubstituted $C_1$-$C_{60}$ alkoxy group may be substituted with those substituents described above in conjunction with the substituted $C_1$-$C_{60}$ alkyl group.

As used herein, the unsubstituted $C_2$-$C_{60}$ alkenyl group (or a $C_2$-$C_{60}$ alkenyl group) is a hydrocarbon chain having a carbon-carbon double bond in the center or at a terminal of the unsubstituted $C_2$-$C_{60}$ alkyl group. Examples of the unsubstituted $C_2$-$C_{60}$ alkenyl group are ethenyl, prophenyl, and butenyl groups. At least one hydrogen atom of the unsubstituted $C_2$-$C_{60}$ alkenyl group may be substituted with those substituents described above in conjunction with the substituted $C_1$-$C_{60}$ alkyl group.

As used herein, the unsubstituted $C_2$-$C_{60}$ alkynyl group (or a $C_2$-$C_{60}$ alkynyl group) is a hydrocarbon chain having a carbon-carbon triple bond in the center or at a terminal of the above-defined $C_2$-$C_{60}$ alkyl group. Examples of the unsubstituted $C_2$-$C_{60}$ alkynyl group are ethynyl and propynyl groups. At least one hydrogen atom of the unsubstituted $C_2$-$C_{60}$ alkynyl group may be substituted with those substituents described above in conjunction with the substituted $C_1$-$C_{60}$ alkyl group.

As used herein, the unsubstituted $C_5$-$C_{60}$ aryl group is a monovalent group having a carbocyclic aromatic system having 5 to 60 carbon atoms including at least one aromatic ring. The unsubstituted $C_5$-$C_{60}$ arylene group is a divalent group having a carbocyclic aromatic system having 5 to 60 carbon atoms including at least one aromatic ring. When the aryl group and the arylene group, respectively, have at least two rings, they may be fused to each other. At least one hydrogen atom of the aryl group and the arylene group may be substituted with those substituents described above in conjunction with the substituted $C_1$-$C_{60}$ alkyl group.

Examples of the substituted or unsubstituted $C_5$-$C_{60}$ aryl group are a phenyl group, a $C_1$-$C_{10}$ alkylphenyl group (for example, ethylphenyl group), a $C_1$-$C_{10}$ alkylbiphenyl group (for example, ethylbiphenyl group), a halophenyl group (for example, o-, m- and p-fluorophenyl groups, a dichlorophenyl group), a dicyanophenyl group, a trifluoromethoxyphenyl group, o-, m-, and p-tolyl groups, o-, m- and p-cumenyl groups, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), an anthracenyl group, an azrenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenylgroup, a coroneryl group, a trinaphthylenyl group, a heptaphenyl group, a heptacenyl group, a piranthrenyl group, and an obarenyl group. Examples of the substituted $C_5$-$C_{60}$ aryl group may be understood based on the above-described examples of the unsubstituted $C_5$-$C_{60}$ aryl group and substituents of the substituted $C_1$-$C_{60}$ alkyl group. Examples of the substituted or unsubstituted $C_5$-$C_{60}$ arylene group may be understood based on the above-described examples of the substituted or unsubstituted $C_5$-$C_{60}$ aryl group.

As used herein, the unsubstituted $C_2$-$C_{60}$ heteroaryl group is a monovalent group having at least one aromatic ring having at least one of the heteroatoms selected from the group consisting of N, O, P, and S, and at least one carbon atom. The unsubstituted $C_2$-$C_{60}$ hetero arylene group is a divalent group having at least one aromatic ring having at least one of the heteroatoms selected from the group consisting of N, O, P, and S and at least one carbon atom. In this regard, when the heteroaryl group and the heteroarylene group, respectively, have at least two rings, they may be fused to each other. At least one hydrogen atom of the heteroaryl group and the hetero arylene group may be substituted with those substituents described above in conjunction with the substituted $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ hetero arylene group may be understood based on the above-described examples of the substituted or unsubstituted $C_2$-$C_{60}$ arylene group.

The substituted or unsubstituted $C_5$-$C_{60}$ aryloxy group is represented by —$OA_2$ (where $A_2$ is a substituted or unsubstituted $C_5$-$C_{60}$ aryl group as described above). The substituted or unsubstituted $C_5$-$C_{60}$ arylthio group is represented by —$SA_3$ (where $A_3$ is a substituted or unsubstituted $C_5$-$C_{60}$ aryl group as described above).

EXAMPLES

Synthesis Example 1

Synthesis of Compound 1

Compound 1 was synthesized according to Reaction Scheme 1 below:

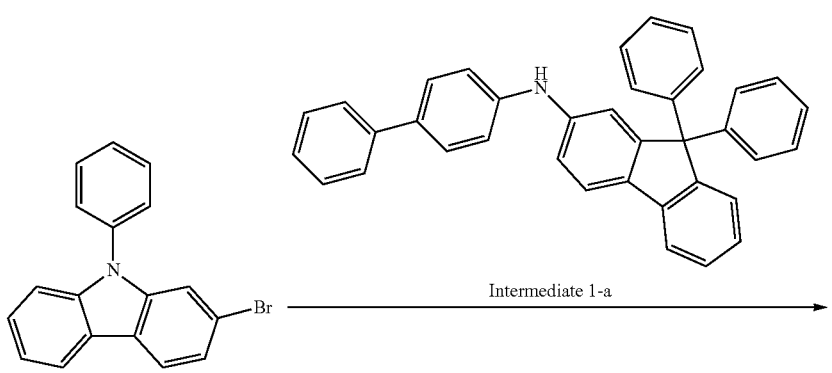

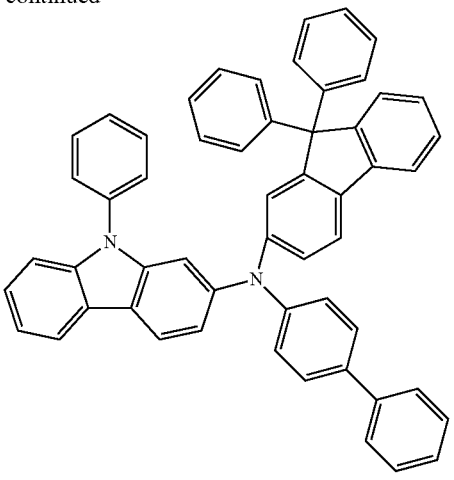

Compound 1

Synthesis of Intermediate 1-a 10 g of Biphenyl-4-ylamine, 24.65 g (1.05 eq) of 2-bromo-9,9-diphenyl-9H-fluorene, 2.71 g (0.05 eq) of tris (dibenzylideneacetone)dipalladium(0)) ($Pd_2(dba)_3$), 0.84 g (0.07 eq) of tri-tert-butylphosphine (P(t-Bu)$_3$), and 11.36 g (2.0 eq) of sodium tert-butoxide were put in a reaction vessel, which was then supplied with $N_2$ in a vacuum, followed by an addition of 90 ml of toluene to obtain a mixture, which was then stirred at 120° C. for about 2 hours. The solvent was removed from the mixture using a rotary evaporator. The reaction product was extracted twice with 200 ml of dichloromethane ($CH_2Cl_2$) and then 150 ml of water 200 ml. The organic layer was collected and was dried using magnesium sulfate to evaporate the solvent. The residue was separated and purified by silica gel column chromatography to obtain 28 g of Intermediate 1-a (Yield: 98%). This compound was identified using liquid chromatography-mass spectroscopy (LC-MS).

$C_{37}H_{27}N$: M+ 485.21

Synthesis of Compound 1

4.5 g of 2-bromo-9-phenyl-9H-carbazole, 7.12 g (1.05 eq) of Intermediate 1-a, 0.64 g (0.05 eq) of tris(dibenzylideneacetone)dipalladium(0) ($Pd_2(dba)_3$), 0.20 g (0.07 eq) of tri-tert-butylphosphine (P(t-Bu)$_3$), and 2.68 g (2.0 eq) of sodium tert-butoxide were put in a reaction vessel, which was then supplied with $N_2$ in a vacuum, followed by an addition of 50 ml of toluene to obtain a mixture, which was then stirred at 120° C. for about 2 hours. The solvent was removed from the mixture using a rotary evaporator. The reaction product was extracted twice with 200 ml of dichloromethane ($CH_2Cl_2$) and then 150 ml of water 200 ml. The organic layer was collected and was dried using magnesium sulfate to evaporate the solvent. The residue was separated and purified by silica gel column chromatography to obtain 7.2 g of Compound 1 (Yield: 71%). This compound was identified using LC-MS and nuclear magnetic resonance (NMR).

$C_{55}H_{38}N_2$: M+ 726.30

1H NMR (CDCl$_3$, 400 MHz) δ (ppm) 7.84 (d, 1H), 7.59 (d, 1H), 7.55 (d, 2H), 7.48 (d, 2H), 7.4 (d, 1H), 7.38 (m, 1H), 7.32 (m, 2H), 7.3-7.2 (m, 10H) 7.14 (m, 4H), 7.1-7.0 (m, 8H) 6.75 (s, 1H), 6.6 (s, 1H), 6.58 (d, 1H), 6.52 (d, 2H), 6.2 (d, 1H)

Synthesis Example 2

Synthesis of Compound 2

Compound 2 was synthesized according to Reaction Scheme 2 below:

<Reaction Scheme 2>

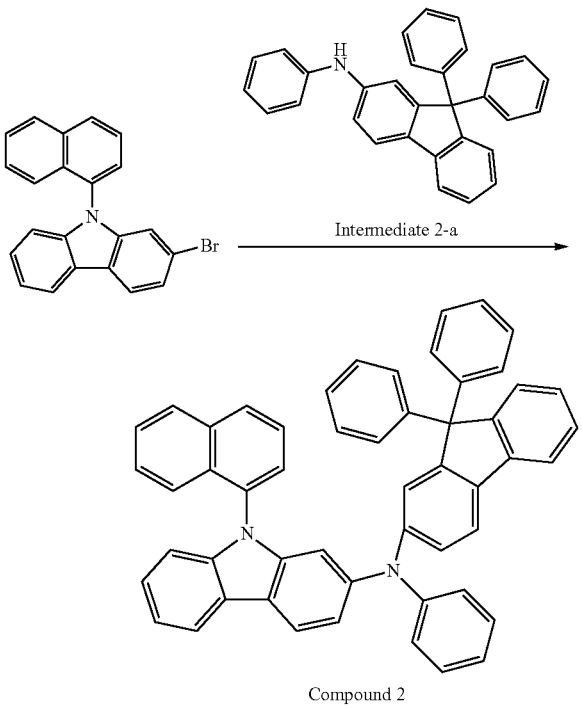

Compound 2

Synthesis of Intermediate 2-a

Intermediate 2-a was prepared in the same manner as in the method of synthesizing Intermediate 1-a of Synthesis Example 1, except that phenylamine, instead of biphenyl-4-ylamine, was used. This compound was identified using LC-MS.

$C_{31}H_{23}N$: M+ 409.18

Synthesis of Compound 2

4.0 g of 2-bromo-9-naphthalen-1-yl-9H-carbazole, 4.62 g (1.05 eq) of Intermediate 2-a, 0.49 g (0.05 eq) of $Pd_2(dba)_3$, 0.15 g (0.07 eq) of $P(t-Bu)_3$, and 2.07 g (2.0 eq) of sodium tert-butoxide were put in a reaction vessel, which was then supplied with $N_2$ in a vacuum, followed by an addition of 40 ml of toluene to obtain a mixture, which was then stirred at 120° C. for about 2 hours. The solvent was removed from the mixture using a rotary evaporator. The reaction product was extracted twice with 150 ml of dichloromethane ($CH_2Cl_2$) and then 150 ml of water. The organic layer was collected and was dried using magnesium sulfate to evaporate the solvent. The residue was separated and purified by silica gel column chromatography to obtain 6.0 g of Compound 2 (Yield: 80%). This compound was identified using LC-MS and nuclear magnetic resonance (NMR).

$C_{53}H_{36}N_2$: M+ 700.29

1H NMR (CDCl$_3$, 400 MHz) δ (ppm) 7.84 (d, 1H), 7.7 (d, 3H), 7.59 (d, 1H), 7.55 (d, 2H), 7.4 (d, 1H), 7.38 (d, 1H), 7.3-7.2 (m, 6H), 7.14 (m, 4H), 7.1-7.0 (m, 10H) 6.75 (s, 1H), 6.62 (m, 1H), 6.6 (s, 1H), 6.58 (d, 1H), 6.46 (d, 2H), 6.2 (d, 1H)

Synthesis Example 3

Synthesis of Compound 3

Compound 3 was synthesized according to Reaction Scheme 3 below:

Synthesis of Intermediate 3-a

Intermediate 3-a was synthesized in the same manner as in the method of synthesizing Intermediate 1-a in Synthesis Example 1, except that biphenyl-3-ylamine, instead of biphenyl-4-ylamine, was used. This compound was identified using LC-MS.

$C_{37}H_{27}N$: M+ 485.21

Synthesis of Compound 3

Compound 3 was synthesized in the same manner as in the method of synthesizing Compound 1 in Synthesis Example 1, except that Intermediate 3-a, instead of Intermediate 1-a, was used. This compound was identified using LC-MS and nuclear magnetic resonance (NMR).

$C_{53}H_{36}N_2$: M+ 726.30

1H NMR (CDCl$_3$, 400 MHz) δ (ppm) 7.84 (d, 1H), 7.59 (d, 1H), 7.55 (d, 2H), 7.48 (d, 2H), 7.4 (d, 1H), 7.38 (m, 1H), 7.32 (m, 2H), 7.3-7.2 (m, 8H) 7.14 (m, 4H), 7.1-7.0 (m, 9H) 6.84 (d, 1H), 6.75 (s, 1H), 6.68 (s, 1H), 6.6 (s, 1H), 6.58 (d, 1H), 6.42 (d, 1H), 6.2 (d, 1H)

Synthesis Example 4

Synthesis of Compound 4

Compound 4 was synthesized according to Reaction Scheme 4 below:

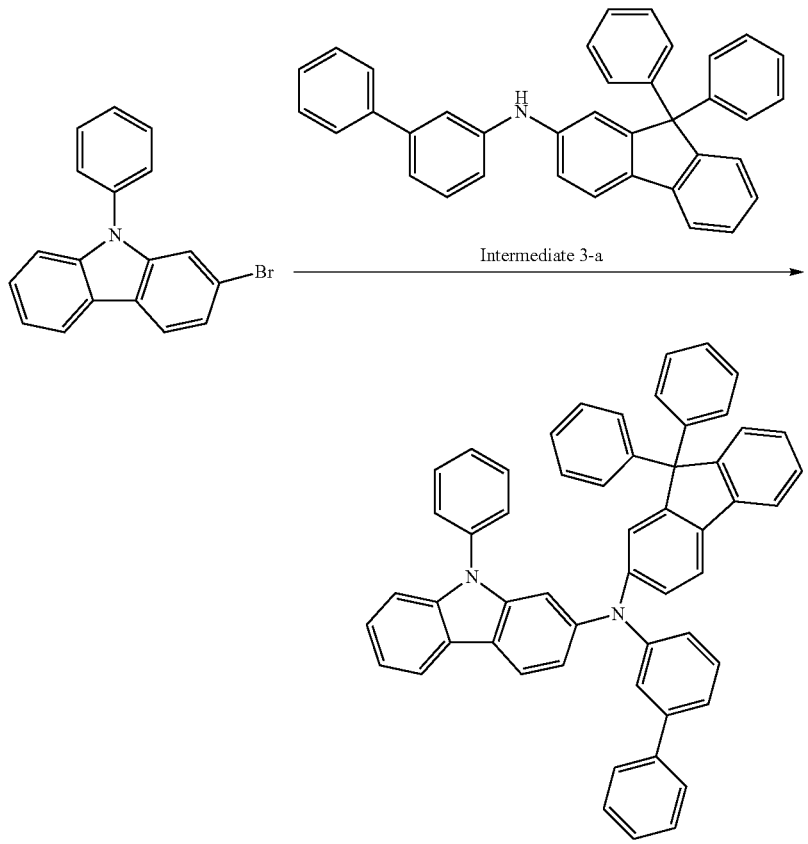

Compound 3

<Reaction Scheme 4>

<Reaction Scheme 5>

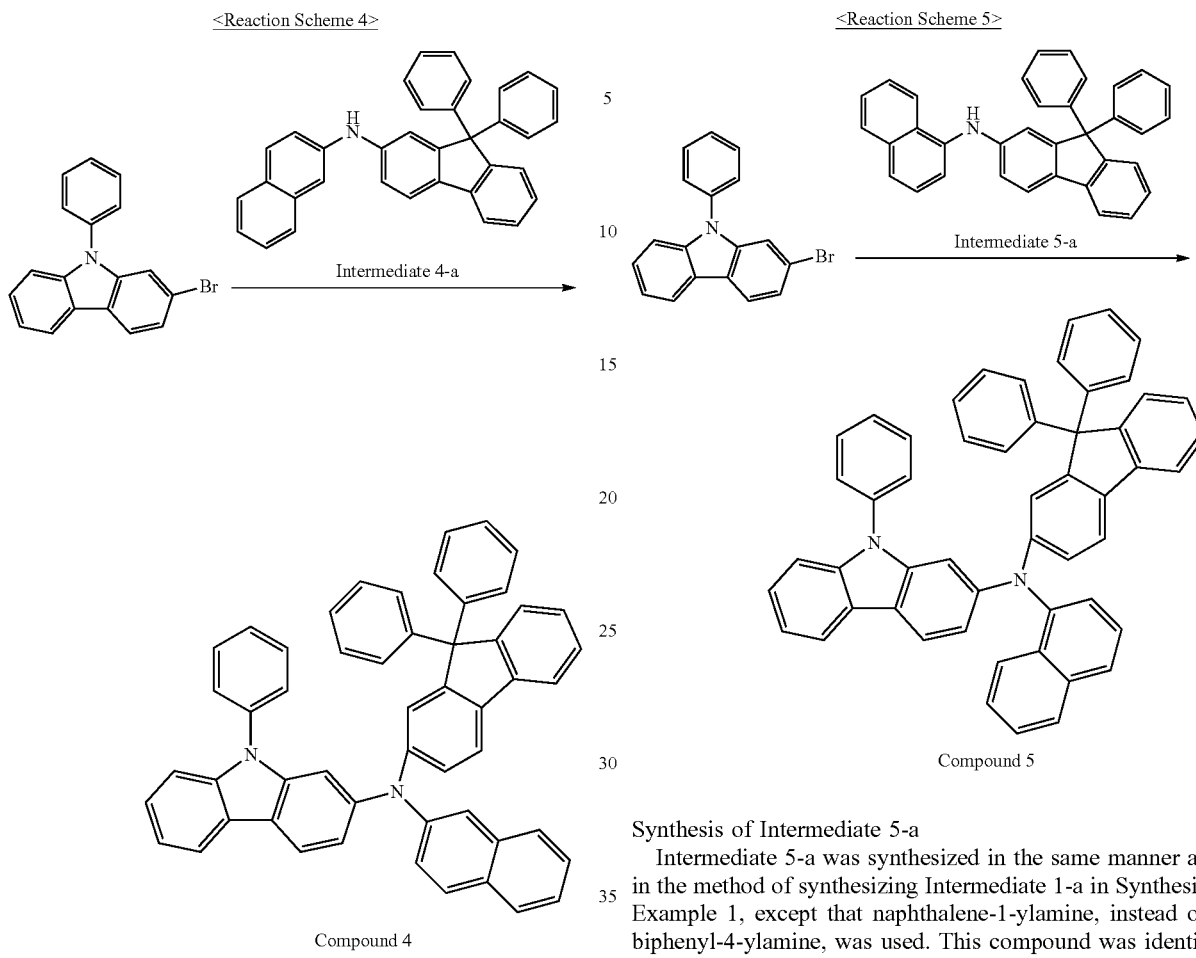

Compound 4

Compound 5

Synthesis of Intermediate 4-a

Intermediate 4-a was synthesized in the same manner as in the method of synthesizing Intermediate 1-a in Synthesis Example 1, except that naphthalene-2-ylamine, instead of biphenyl-4-ylamine, was used. This compound was identified using LC-MS.

$C_{35}H_{25}N$: M+ 459.20

Synthesis of Compound 4

Compound 4 was synthesized in the same manner as in the method of synthesizing Compound 1 in Synthesis Example 1, except that Intermediate 4-a, instead of Intermediate 1-a, was used. This compound was identified using LC-MS and nuclear magnetic resonance (NMR).

$C_{53}H_{36}N_2$: M+ 700.29

1H NMR (CDCl$_3$, 400 MHz) δ (ppm) 7.84 (d, 1H), 7.59 (d, 1H), 7.55 (d, 3H), 7.51 (d, 1H), 7.44 (d, 1H), 7.40 (d, 1H), 7.38 (d, 1H), 7.3-7.2 (m, 8H), 7.14 (m, 4H), 7.1-7.0 (m, 9H) 6.79 (s, 1H), 6.76 (d, 1H), 6.75 (s, 1H), 6.6 (s, 1H), 6.58 (d, 1H), 6.2 (d, 1H)

Synthesis Example 5

Synthesis of Compound 5

Compound 5 was synthesized according to Reaction Scheme 5 below:

Synthesis of Intermediate 5-a

Intermediate 5-a was synthesized in the same manner as in the method of synthesizing Intermediate 1-a in Synthesis Example 1, except that naphthalene-1-ylamine, instead of biphenyl-4-ylamine, was used. This compound was identified using LC-MS.

$C_{35}H_{25}N$: M+ 459.20

Synthesis of Compound 5

Compound 5 was synthesized in the same manner as in the method of synthesizing Compound 1 in Synthesis Example 1, except that Intermediate 5-a, instead of Intermediate 1-a, was used. This compound was identified using LC-MS and nuclear magnetic resonance (NMR).

$C_{53}H_{36}N_2$: M+ 700.29

1H NMR (CDCl$_3$, 400 MHz) δ (ppm) 7.84 (d, 1H), 7.66 (d, 1H), 7.61 (d, 1H), 7.59 (d, 1H), 7.55 (d, 2H), 7.40 (d, 1H), 7.38 (d, 1H), 7.31 (m, 1H), 7.3-7.2 (m, 8H), 7.16 (d, 1H), 7.15 (m, 1H), 7.14 (m, 4H), 7.1-7.0 (m, 8H) 6.75 (s, 1H), 6.6 (s, 1H), 6.58 (d, 1H), 6.55 (d, 1H), 6.2 (d, 1H)

Synthesis Example 6

Synthesis of Compound 6

Compound 6 was synthesized in the same manner as in the method of synthesizing Compound 1 in Synthesis Example 1, except that Intermediate 2-a, instead of Intermediate 1-a, was used. This compound was identified using LC-MS and nuclear magnetic resonance (NMR).

$C_{49}H_{34}N_2$: M+ 650.27

1H NMR (CDCl$_3$, 400 MHz) δ (ppm) 7.84 (d, 1H), 7.59 (d, 1H), 7.55 (d, 2H), 7.40 (d, 1H), 7.38 (m, 1H), 7.3-7.2 (m, 7H), 7.14 (m, 4H), 7.1-7.0 (m, 10H) 6.75 (s, 1H), 6.62 (m, 1H), 6.6 (s, 1H), 6.58 (d, 1H), 6.46 (d, 2H), 6.2 (d, 1H)

Synthesis Example 7

Synthesis of Compound 7

Compound 7 was synthesized in the same manner as in the method of synthesizing Compound 1 in Synthesis Example 1, except that 9-biphenyl-4-yl-2-bromo-9H-carbazole, instead of 2-bromo-9-phenyl-9H-carbazole, was used. This compound was identified using LC-MS and nuclear magnetic resonance (NMR).

$C_{61}H_{42}N_2$: M+ 802.33

1H NMR (CDCl$_3$, 400 MHz) δ (ppm) 7.84 (d, 1H), 7.59 (d, 1H), 7.55 (d, 2H), 7.5 (d, 2H), 7.48 (d, 4H), 7.40 (d, 1H), 7.38 (m, 1H), 7.32 (d, 4H), 7.3-7.2 (m, 8H), 7.14 (m, 4H), 7.1-7.0 (m, 8H), 6.75 (s, 1H), 6.6 (s, 1H), 6.58 (d, 1H), 6.52 (d, 2H), 6.2 (d, 1H)

Synthesis Example 8

Synthesis of Compound 8

Compound 8 was synthesized in the same manner as in the method of synthesizing Compound 2 in Synthesis Example 2, except that 2-bromo-9-phenyl-9H-carbazole, instead of 2-bromo-9-naphthalen-1-yl-9H-carbazole, was used. This compound was identified using LC-MS and nuclear magnetic resonance (NMR).

$C_{53}H_{36}N_2$: M+ 700.29

1H NMR (CDCl$_3$, 400 MHz) δ (ppm) 7.84 (d, 1H), 7.7 (d, 4H), 7.59 (d, 1H), 7.55 (d, 2H), 7.40 (d, 1H), 7.38 (m, 1H), 7.3-7.2 (m, 5H), 7.14 (m, 4H), 7.1-7.0 (m, 10H), 6.75 (s, 1H), 6.62 (m, 1H), 6.6 (s, 1H), 6.58 (d, 1H), 6.46 (d, 2H), 6.2 (d, 1H)

Synthesis Example 9

Synthesis of Compound 9

Compound 9 was synthesized in the same manner as in the method of synthesizing Compound 2 in Synthesis Example 2, except that 2-bromo-9-naphthalen-1-yl-9H-carbazole, instead of 2-bromo-9-naphthalen-1-yl-9H-carbazole, was used. This compound was identified using LC-MS and nuclear magnetic resonance (NMR).

$C_{55}H_{38}N_2$: M+ 726.30

1H NMR (CDCl$_3$, 400 MHz) δ (ppm) 7.84 (d, 1H), 7.59 (d, 1H), 7.55 (d, 2H), 7.50 (d, 2H), 7.48 (d, 2H), 7.40 (d, 1H), 7.38 (m, 1H), 7.32 (m, 2H) 7.3-7.2 (m, 5H), 7.14 (m, 4H), 7.1-7.0 (m, 10H), 6.75 (s, 1H), 6.62 (m, 1H), 6.6 (s, 1H), 6.58 (d, 1H), 6.46 (d, 2H), 6.2 (d, 1H)

Synthesis Example 10

Synthesis of Compound 10

Synthesis of Intermediate 10-a

Intermediate 10-a was synthesized in the same manner as in the method of synthesizing Intermediate 1-a in Synthesis Example 1, except that 4-bromo-benzonitrile, instead of biphenyl-4-ylamine, was used. This compound was identified using LC-MS.

$C_{32}H_{22}N_2$: M+ 434.18

Synthesis of Compound 10

Compound 10 was synthesized in the same manner as in the method of synthesizing Compound 1 in Synthesis Example 1, except that Intermediate 10-a, instead of Intermediate 1-a, was used. This compound was identified using LC-MS and nuclear magnetic resonance (NMR).

$C_{50}H_{33}N_3$: M+ 675.27

1H NMR (CDCl$_3$, 400 MHz) δ (ppm) 7.84 (d, 1H), 7.59 (d, 1H), 7.55 (d, 2H), 7.40 (d, 1H), 7.38 (d, 1H), 7.3-7.2 (m, 9H), 7.14 (m, 4H), 7.1-7.0 (m, 8H), 6.75 (s, 1H), 6.64 (d, 2H), 6.6 (s, 1H), 6.58 (d, 1H), 6.2 (d, 1H)

Synthesis Example 11

Synthesis of Compound 11

Synthesis of Intermediate 11-a

Intermediate 11-a was synthesized in the same manner as in the method of synthesizing Intermediate 1-a in Synthesis Example 1, except that 2-(4-Bromo-phenyl)-pyridine, instead of biphenyl-4-ylamine, was used. This compound was identified using LC-MS.

$C_{36}H_{26}N_2$: M+ 486.21

Synthesis of Compound 11

Compound 11 was synthesized in the same manner as in the method of synthesizing Compound 1 in Synthesis Example 1, except that Intermediate 11-a, instead of Intermediate 1-a, was used. This compound was identified using LC-MS and nuclear magnetic resonance (NMR).

$C_{54}H_{37}N_3$: M+ 727.30

1H NMR (CDCl$_3$, 400 MHz) δ (ppm) 8.56 (d, 1H), 7.84 (d, 1H), 7.74 (d, 2H), 7.59 (d, 1H), 7.55 (d, 2H), 7.54 (d, 1H), 7.47 (m, 1H), 7.4 (d, 1H), 7.38 (m, 1H), 7.3-7.2 (m, 7H), 7.14 (m, 4H), 7.1-7.0 (m, 8H), 6.98 (m, 1H), 6.75 (s, 1H), 6.6 (s, 1H), 6.58 (d, 1H), 6.55 (d, 2H), 6.2 (d, 1H)

Synthesis Example 12

Synthesis of Compound 12

Synthesis of Intermediate 12-a

Intermediate 12-a was synthesized in the same manner as in the method of synthesizing Intermediate 1-a in Synthesis Example 1, except that 3-(4-Bromo-phenyl)-pyridine, instead of biphenyl-4-ylamine, was used. This compound was identified using LC-MS.

$C_{36}H_{26}N_2$: M+ 486.21

Synthesis of Compound 12

Compound 12 was synthesized in the same manner as in the method of synthesizing Compound 1 in Synthesis Example 1, except that Intermediate 12-a, instead of Intermediate 1-a, was used. This compound was identified using LC-MS and nuclear magnetic resonance (NMR).

$C_{54}H_{37}N_3$: M+ 727.30

1H NMR (CDCl$_3$, 400 MHz) δ (ppm) 8.81 (s, 1H), 8.55 (d, 1H), 7.97 (d, 1H), 7.84 (d, 1H), 7.59 (d, 1H), 7.55 (d, 2H), 7.44 (m, 1H), 7.4 (d, 1H), 7.38 (m, 1H), 7.3-7.2 (m, 9H), 7.14 (m, 4H), 7.1-7.0 (m, 8H), 6.75 (s, 1H), 6.6 (s, 1H), 6.58 (d, 1H), 6.55 (d, 2H), 6.2 (d, 1H)

Synthesis Example 13

Synthesis of Compound 13

Synthesis of Intermediate 13-a

Intermediate 13-a was synthesized in the same manner as in the method of synthesizing Intermediate 1-a in Synthesis Example 1, except that 5-Bromo-[2,2']bithiophenyl, instead of biphenyl-4-ylamine, was used. This compound was identified using LC-MS.

$C_{33}H_{23}NS_2$: M+ 497.13

Synthesis of Compound 13

Compound 13 was synthesized in the same manner as in the method of synthesizing Compound 1 in Synthesis Example 1, except that Intermediate 13-a, instead of Intermediate 1-a, was used. This compound was identified using LC-MS and nuclear magnetic resonance (NMR).

$C_{51}H_{34}N_2S_2$: M+ 738.22

1H NMR (CDCl$_3$, 400 MHz) δ (ppm) 7.84 (d, 1H), 7.59 (d, 1H), 7.55 (d, 2H), 7.4 (d, 1H), 7.38 (m, 1H), 7.3-7.2 (m, 8H), 7.14 (m, 4H), 7.1-7.0 (m, 10H), 6.75 (s, 1H), 6.6 (s, 1H), 6.58 (d, 1H), 6.5 (d, 1H), 6.2 (d, 1H), 6.0 (d, 1H)

Synthesis Example 14

Synthesis of Compound 14

Synthesis of Intermediate 14-a

Intermediate 14-a was synthesized in the same manner as in the method of synthesizing Intermediate 1-a in Synthesis Example 1, except that 4-(4-bromo-phenyl)-pyridine, instead of biphenyl-4-ylamine, was used. This compound was identified using LC-MS.

$C_{36}H_{26}N_2$: M+ 486.21

Synthesis of Compound 14

Compound 14 was synthesized in the same manner as in the method of synthesizing Compound 1 in Synthesis Example 1, except that Intermediate 14-a, instead of Intermediate 1-a, was used. This compound was identified using LC-MS and nuclear magnetic resonance (NMR).

$C_{54}H_{37}N_3$: M+ 727.30

1H NMR (CDCl$_3$, 400 MHz) δ (ppm) 8.65 (d, 2H), 7.84 (d, 1H), 7.6 (d, 2H), 7.59 (d, 1H), 7.55 (d, 2H), 7.4 (d, 1H), 7.38 (m, 1H), 7.3-7.2 (m, 9H), 7.14 (m, 4H), 7.1-7.0 (m, 8H), 6.75 (s, 1H), 6.6 (s, 1H), 6.58 (d, 1H), 6.52 (d, 2H), 6.2 (d, 1H)

Synthesis Example 15

Synthesis of Compound 15

Synthesis of Intermediate 15-a

Intermediate 15-a was synthesized in the same manner as in the method of synthesizing Intermediate 1-a in Synthesis Example 1, except that 5'-bromo-[1,1',3',1'']terphenyl instead of biphenyl-4-ylamine, was used. This compound was identified using LC-MS.

$C_{43}H_{21}N$: M+ 561.25

Synthesis of Compound 15

Compound 15 was synthesized in the same manner as in the method of synthesizing Compound 1 in Synthesis Example 1, except that Intermediate 15-a, instead of Intermediate 1-a, was used. This compound was identified using LC-MS and nuclear magnetic resonance (NMR).

$C_{61}H_{42}N_2$: M+ 802.33

1H NMR (CDCl$_3$, 400 MHz) δ (ppm) 7.84 (d, 1H), 7.59 (d, 1H), 7.55 (d, 2H), 7.48 (d, 4H), 7.4 (d, 1H), 7.38 (m, 1H), 7.32 (m, 4H), 7.3-7.2 (m, 9H), 7.14 (m, 4H), 7.1-7.0 (m, 9H), 6.75 (s, 1H), 6.64 (s, 2H), 6.6 (s, 1H), 6.58 (d, 1H), 6.2 (d, 1H)

Synthesis Example 16

Synthesis of Compound 16

Compound 16 was synthesized according to Reaction Scheme 6 below:

<Reaction Scheme 6>

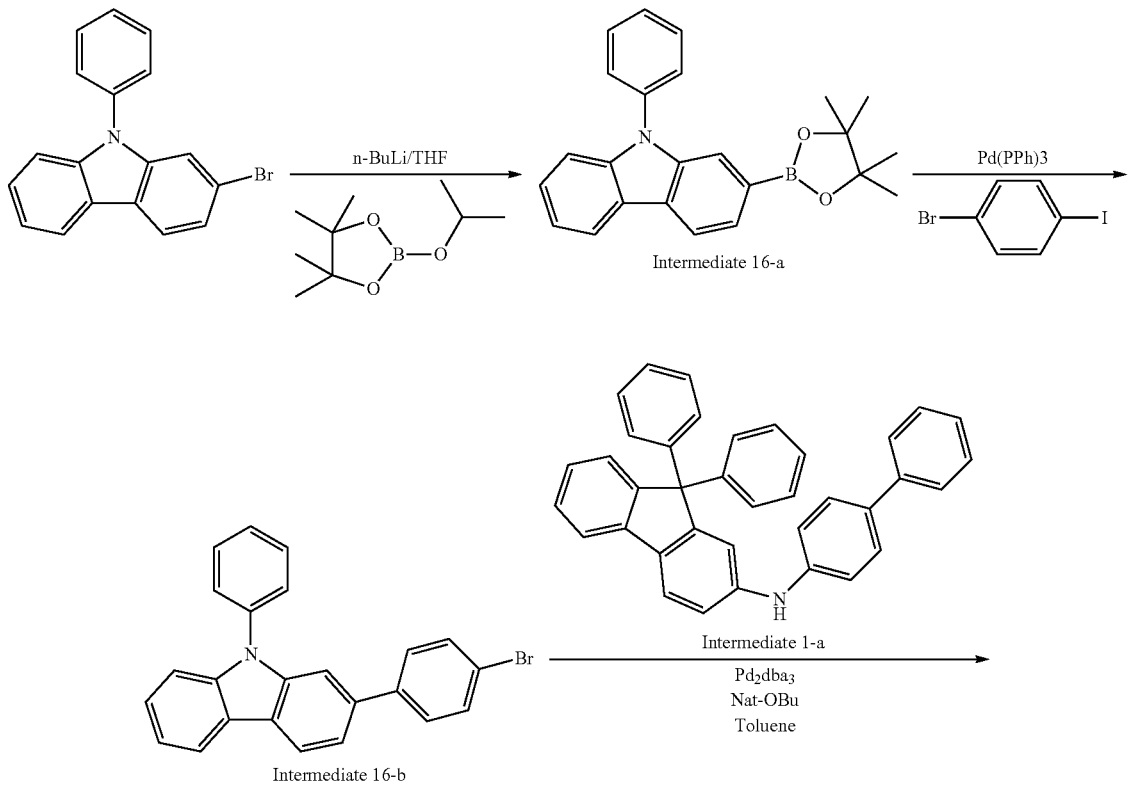

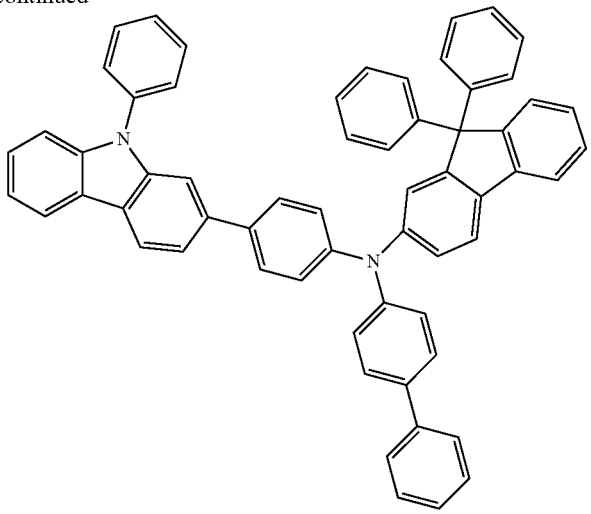

Compound 16

Synthesis of Intermediate 16-a 10 g of 2-bromo-9-phenyl-9H-carbazole was put in a reaction vessel, which was then supplied with $N_2$ in a vacuum, followed by an addition of 69 ml of anhydrous THF to obtain a mixture. While the temperature of the mixture was maintained at about −78° C., 13.04 ml (1.05 eq) of n-BuLi was slowly dropwise added thereto. The resulting mixture was stirred for about 2 hours while being kept at the same temperature, followed by an addition of 7.6 ml (1.2 eq) of 2-isopropoxy-4,4,5,5-tetramethyl-1,3,2-dioxaborolane and stirring for about 2 hours. The solvent was removed from the mixture using a rotary evaporator. The reaction product was extracted twice with 200 ml of dichloromethane ($CH_2Cl_2$) and then 150 ml of water 200 ml. The organic layer was collected and was dried using magnesium sulfate to evaporate the solvent. The residue was separated and purified by silica gel column chromatography to obtain 9 g of Intermediate 16-2 (Yield: 78%). This compound was identified using LC-MS.

$C_{24}H_{24}BNO_2$: M+ 369.19

Synthesis of Intermediates 16-b 9 g of Intermediate 16-b, 7.58 g (1.1 eq) of 1-bromo-4-iodo-benzene, 1.97 g (0.07 eq) of tetrakis(triphenylphosphine)palladium(0)), and 5.05 g (1.5 eq) of potassium carbonate were put in a reaction vessel, which was then supplied with $N_2$ in a vacuum, followed by an addition of 40 ml of THF and 20 ml of distilled water to obtain a mixture, which was then stirred at about 75° C. for about 24 hours. The solvent was removed from the mixture using a rotary evaporator. The reaction product was extracted twice with 200 ml of dichloromethane ($CH_2Cl_2$) and then 150 ml of water 200 ml. The organic layer was collected and was dried using magnesium sulfate to evaporate the solvent. The residue was separated and purified by silica gel column chromatography to obtain 7.35 g of Intermediate 16-6 (Yield: 76%). This compound was identified using LC-MS.

$C_{24}H_{16}BrN$: M+ 397.05

Synthesis of Compound 16

5.0 g of Intermediate 16-b, 6.4 g (1.05 eq) of Intermediate 1-a, 0.58 g (0.05 eq) of tris(dibenzylideneacetone)dipalladium(0) ($Pd_2(dba)_3$), 0.36 g (0.07 eq) of tri-tert-butylphosphine) ($P(t-Bu)_3$), and 2.53 g (2.0 eq) of sodium tert-butoxide were put in a reaction vessel, which was then supplied with $N_2$ in a vacuum, followed by an addition of 60 ml of toluene to obtain a mixture, which was then stirred at about 120° C. for about 2 hours. The solvent was removed from the mixture using a rotary evaporator. The reaction product was extracted twice with 200 ml of dichloromethane ($CH_2Cl_2$) and then 150 ml of water. The organic layer was collected and was dried using magnesium sulfate to evaporate the solvent. The residue was separated and purified by silica gel column chromatography to obtain 7.26 g of Compound 16 (Yield 72%). This compound was identified using LC-MS and nuclear magnetic resonance (NMR).

$C_{61}H_{42}N_2$: M+ 802.33

1H NMR (CDCl$_3$, 400 MHz) δ (ppm) 7.84 (d, 1H), 7.62 (s, 1H), 7.61 (d, 1H), 7.59 (d, 1H), 7.55 (d, 2H), 7.48 (d, 2H), 7.40 (d, 1H), 7.38 (m, 1H), 7.32 (m, 2H), 7.3-7.2 (m, 12H), 7.14 (m, 4H), 7.1-7.0 (m, 8H), 6.75 (s, 1H), 6.58 (d, 1H), 6.52 (d, 4H)

Synthesis Example 17

Synthesis of Compound 17

Compound 17 was synthesized according to Reaction Scheme 7 below:

<Reaction Scheme 7>
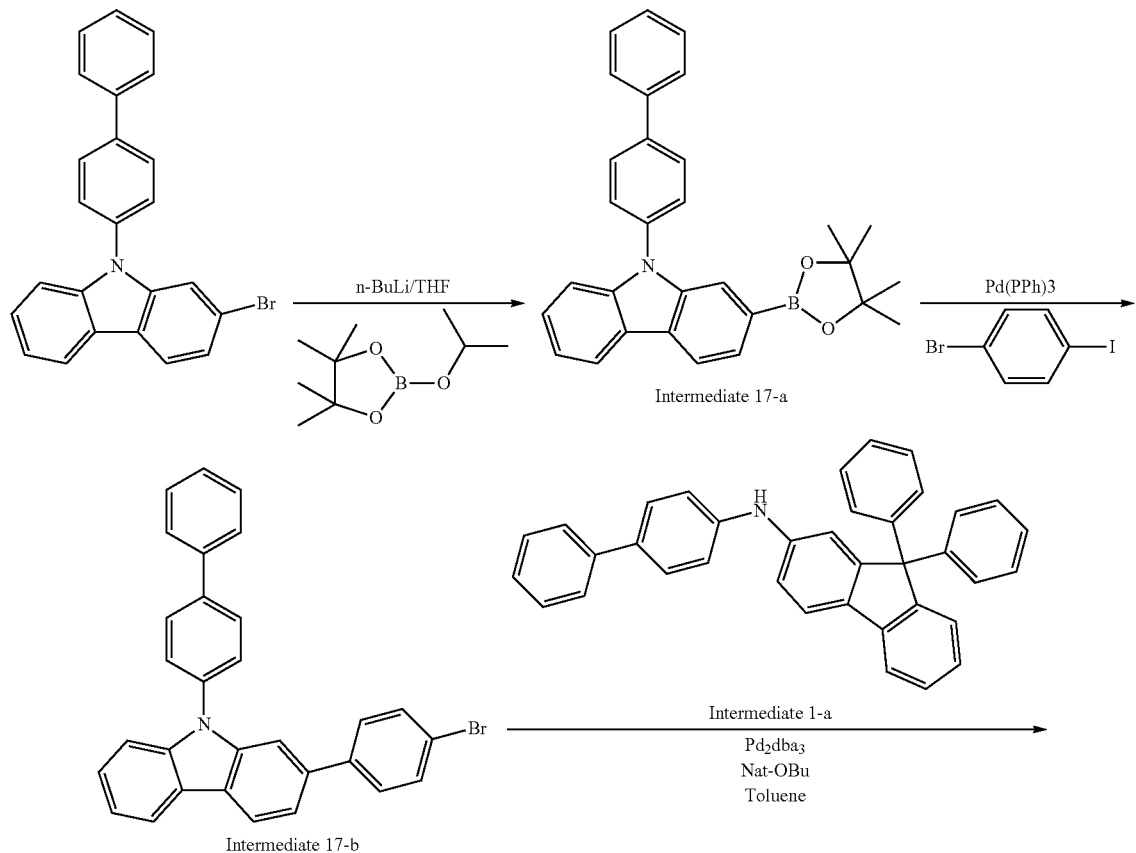
Intermediate 17-a
Intermediate 17-b
Intermediate 1-a
Pd₂dba₃
Nat-OBu
Toluene
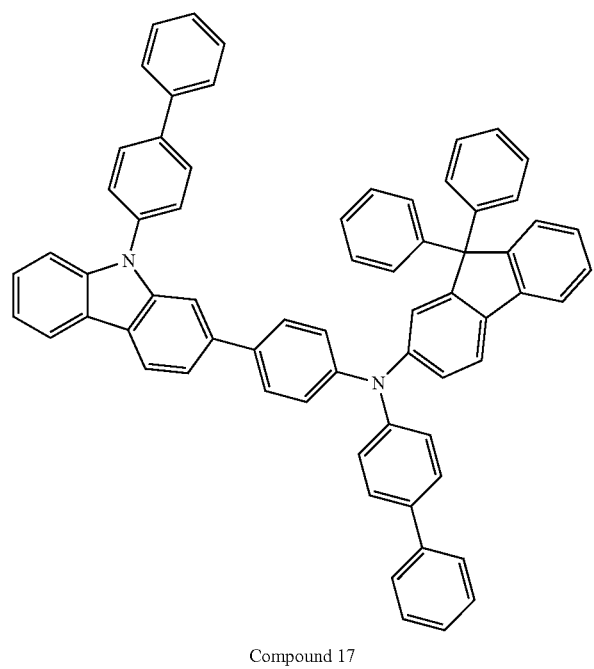
Compound 17

Synthesis of Intermediate 17-a

Intermediate 17-a was synthesized in the same manner as in the method of synthesizing Intermediate 16-a in Synthesis Example 16, except that 9-Biphenyl-4-yl-2-bromo-9H-carbazole, instead of 2-bromo-9-phenyl-9H-carbazole, was used. This compound was identified using LC-MS.

$C_{30}H_{28}BNO_2$: M+ 445.22

Synthesis of Intermediate 17-b

Intermediate 17-b was synthesized in the same manner as in the method of synthesizing Intermediate 16-b in Synthesis Example 16, except that Intermediate 17-a, instead of Intermediate 16-a, was used. This compound was identified using LC-MS.

$C_{30}H_{20}BrN$: M+ 473.08

Synthesis of Compound 17

Compound 17 was synthesized in the same manner as in the method of synthesizing Compound 16 in Synthesis Example 16, except that Intermediate 17-b, instead of Intermediate 16-b, was used. This compound was identified using LC-MS and nuclear magnetic resonance (NMR).

$C_{67}H_{46}N_2$: M+ 878.37

1H NMR (CDCl$_3$, 400 MHz) δ (ppm) 7.84 (d, 1H), 7.62 (s, 1H), 7.61 (d, 1H), 7.59 (d, 1H), 7.55 (d, 2H), 7.5 (d, 2H), 7.48 (d, 4H), 7.40 (d, 1H), 7.38 (m, 1H), 7.32 (m, 4H), 7.3-7.2 (m, 10H), 7.14 (m, 4H), 7.1-7.0 (m, 8H), 6.75 (s, 1H), 6.58 (d, 1H), 6.52 (d, 4H)

Synthesis Example 18

Synthesis of Compound 18

Synthesis of Compound 18

Compound 18 was synthesized in the same manner as in the method of synthesizing Compound 16 in Synthesis Example 16, except that Intermediate 3-a, instead of Intermediate 1-a, was used. This compound was identified using LC-MS and nuclear magnetic resonance (NMR).

$C_{61}H_{42}N_2$: M+ 802.33

1H NMR (CDCl$_3$, 400 MHz) δ (ppm) 7.84 (d, 1H), 7.62 (s, 1H), 7.61 (d, 1H), 7.59 (d, 1H), 7.55 (d, 2H), 7.48 (d, 2H), 7.40 (d, 1H), 7.38 (m, 1H), 7.32 (m, 2H), 7.3-7.2 (m, 10H), 7.14 (m, 4H), 7.1-7.0 (m, 9H), 6.84 (d, 1H), 6.75 (s, 1H), 6.68 (s, 1H), 6.58 (d, 1H), 6.52 (d, 2H) 6.42 (d, 1H)

Synthesis Example 19

Synthesis of Compound 19

Synthesis of Compound 19

Compound 19 was synthesized in the same manner as in the method of synthesizing Compound 16 in Synthesis Example 16, except that Intermediate 4-a, instead of Intermediate 1-a, was used. This compound was identified using LC-MS and nuclear magnetic resonance (NMR).

$C_{59}H_{40}N_2$: M+ 776.32

1H NMR (CDCl$_3$, 400 MHz) δ (ppm) 7.84 (d, 1H), 7.62 (s, 1H), 7.61 (d, 1H), 7.59 (d, 1H), 7.55 (d, 3H), 7.51 (d, 1H), 7.44 (d, 1H), 7.4 (d, 1H), 7.38 (m, 1H), 7.3-7.2 (m, 10H), 7.14 (m, 4H), 7.1-7.0 (m, 9H), 6.79 (s, 1H), 6.76 (d, 1H), 6.75 (s, 1H), 6.58 (d, 1H), 6.52 (d, 2H)

Synthesis Example 20

Synthesis of Compound 20

Synthesis of Compound 20

Compound 20 was synthesized in the same manner as in the method of synthesizing Compound 16 in Synthesis Example 16, except that Intermediate 7-a, instead of Intermediate 1-a, was used. This compound was identified using LC-MS and nuclear magnetic resonance (NMR).

$C_{60}H_{41}N_3$: M+ 803.33

1H NMR (CDCl$_3$, 400 MHz) δ (ppm) 8.56 (d, 1H), 7.84 (d, 1H), 7.74 (d, 2H), 7.62 (s, 1H), 7.61 (d, 1H), 7.59 (d, 1H), 7.55 (d, 2H), 7.54 (d, 1H), 7.47 (m, 1H), 7.40 (d, 1H), 7.38 (m, 1H), 7.3-7.2 (m, 9H), 7.14 (m, 4H), 7.1-7.0 (m, 8H), 6.98 (m, 1H), 6.75 (s, 1H), 6.58 (d, 1H), 6.55 (d, 2H) 6.52 (d, 2H)

Synthesis Example 21

Synthesis of Compound 21

Synthesis of Intermediate 21-a

Intermediate 21-a was synthesized in the same manner as in the method of synthesizing Intermediate 1-a in Synthesis Example 1, except that 4'-amino-biphenyl-4-carbonitrile, instead of biphenyl-4-ylamine, was used. This compound was identified using LC-MS.

$C_{38}H_{26}N_2$: M+ 510.63

Synthesis of Compound 21

Compound 21 was synthesized in the same manner as in the method of synthesizing Compound 16 in Synthesis Example 16, except that Intermediate 21-a, instead of Intermediate 1-a, was used. This compound was identified using LC-MS and nuclear magnetic resonance (NMR).

$C_{62}H_{41}N_3$: M+ 827.33

1H NMR (CDCl$_3$, 400 MHz) δ (ppm) 7.84 (d, 1H), 7.66 (d, 2H), 7.62 (s, 1H), 7.61 (d, 1H), 7.59 (d, 1H), 7.57 (d, 2H), 7.55 (d, 2H), 7.40 (d, 1H), 7.38 (m, 1H), 7.3-7.2 (m, 11H), 7.14 (m, 4H), 7.1-7.0 (m, 8H), 6.75 (s, 1H), 6.58 (d, 1H), 6.52 (d, 4H)

Synthesis Example 22

Synthesis of Compound 22

Synthesis of Compound 22

Compound 22 was synthesized in the same manner as in the method of synthesizing Compound 16 in Synthesis Example 16, except that Intermediate 12-a, instead of Intermediate 1-a, was used. This compound was identified using LC-MS and nuclear magnetic resonance (NMR).

$C_{60}H_{41}N_3$: M+ 803.3

1H NMR (CDCl$_3$, 400 MHz) δ (ppm) 8.81 (s, 1H), 8.55 (d, 1H), 7.97 (d, 1H), 7.84 (d, 1H), 7.62 (s, 1H), 7.61 (d, 1H), 7.59 (d, 1H), 7.55 (d, 2H), 7.44 (m, 1H), 7.40 (d, 1H), 7.38 (m, 1H), 7.3-7.2 (m, 11H), 7.14 (m, 4H), 7.1-7.0 (m, 8H), 6.75 (s, 1H), 6.58 (d, 1H), 6.52 (d, 4H)

Synthesis Example 23

Synthesis of Compound 23

Synthesis of Compound 22

Compound 23 was synthesized in the same manner as in the method of synthesizing Compound 16 in Synthesis Example 16, except that Intermediate 2-a, instead of Intermediate 1-a, was used. This compound was identified using LC-MS and nuclear magnetic resonance (NMR).

$C_{55}H_{38}N_2$: M+ 726.30

1H NMR (CDCl$_3$, 400 MHz) δ (ppm) 7.84 (d, 1H), 7.62 (s, 1H), 7.61 (d, 1H), 7.59 (d, 1H), 7.55 (d, 2H), 7.40 (d, 1H), 7.38 (m, 1H), 7.3-7.2 (m, 9H), 7.14 (m, 4H), 7.1-7.0 (m, 10H), 6.75 (s, 1H), 6.62 (m, 1H), 6.58 (d, 1H), 6.52 (d, 2H) 6.46 (d, 2H)

Synthesis Example 24

Synthesis of Compound 24

Synthesis of Intermediate 24-a

Intermediate 24-a was synthesized in the same manner as in the method of synthesizing Intermediate 16-a in Synthesis Example 16, except that 2-bromo-9-naphthalen-2-yl-9H-carbazole, instead of 2-bromo-9-phenyl-9H-carbazole, was used. This compound was identified using LC-MS.

$C_{28}H_{26}BNO_2$: M+ 419.21

Synthesis of Intermediates 24-b

Intermediate 24-b was synthesized in the same manner as in the method of synthesizing Intermediate 16-b in Synthesis Example 16, except that Intermediate 24-a, instead of Intermediate 16-a, was used. This compound was identified using LC-MS.

$C_{28}H_{18}BrN$: M+ 447.06

Synthesis of Compound 24

Compound 24 was synthesized in the same manner as in the method of synthesizing Compound 16 in Synthesis Example 16, except that Intermediate 24-b, instead of Intermediate 16-b, was used. This compound was identified using LC-MS and nuclear magnetic resonance (NMR).

$C_{65}H_{44}N_2$: M+ 852.35

1H NMR (CDCl$_3$, 400 MHz) δ (ppm) 7.84 (d, 1H), 7.7 (d, 4H), 7.62 (s, 1H), 7.61 (d, 1H), 7.59 (d, 1H), 7.55 (d, 2H), 7.48 (d, 2H), 7.40 (d, 1H), 7.38 (m, 1H), 7.32 (d, 2H), 7.3-7.2 (m, 10H), 7.14 (m, 4H), 7.1-7.0 (m, 8H), 6.75 (s, 1H), 6.58 (d, 1H), 6.52 (d, 4H)

Synthesis Example 25

Synthesis of Compound 25

Compound 25 was synthesized according to Reaction Scheme 8 below:

<Reaction Scheme 8>

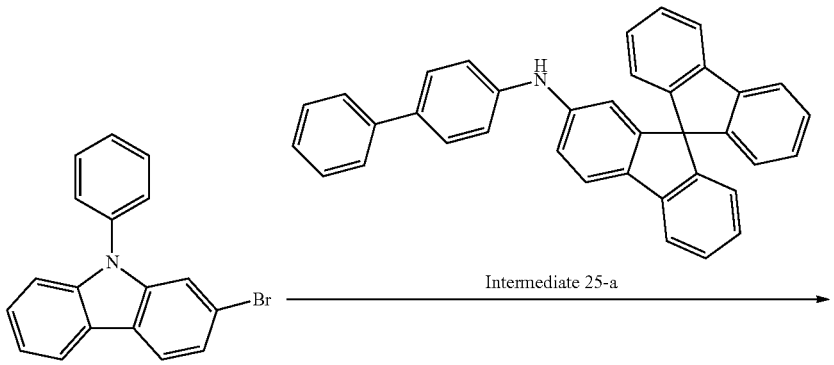

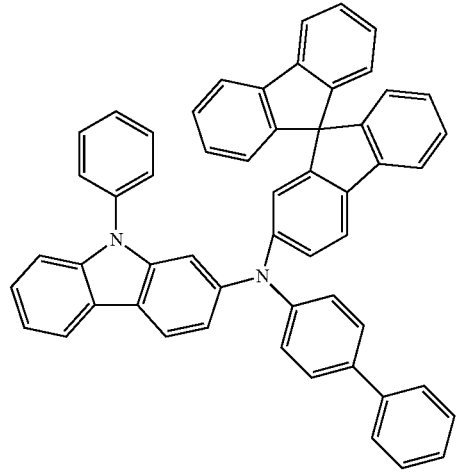

Compound 25

Synthesis of Intermediate 25-a

Intermediate 25-a was synthesized in the same manner as in the method of synthesizing Intermediate 1-a in Synthesis Example 1, except that 2-bromo-spirofluorene, instead of 2-bromo-9,9-diphenyl-9H-fluorene, was used. This compound was identified using LC-MS. This compound was identified using LC-MS.

$C_{37}H_{25}N$: M+ 483.20

Synthesis of Compound 25

Compound 25 was synthesized in the same manner as in the method of synthesizing Compound 1 in Synthesis Example 1, except that Intermediate 25-a, instead of Intermediate 1-a, was used. This compound was identified using LC-MS and nuclear magnetic resonance (NMR).

$C_{55}H_{36}N_2$: M+ 724.29

1H NMR (CDCl$_3$, 400 MHz) δ (ppm) 7.84 (d, 1H), 7.72 (d, 2H), 7.59 (d, 1H), 7.55 (d, 2H), 7.48 (d, 2H), 7.4 (d, 1H), 7.38 (m, 1H), 7.35 (d, 2H), 7.32 (m, 2H), 7.3-7.2 (m, 10H), 7.19 (m, 2H), 7.16 (m, 2H), 7.08 (m, 1H), 7.0 (m, 1H), 6.75 (s, 1H), 6.6 (s, 1H), 6.58 (d, 1H), 6.52 (d, 2H), 6.2 (d, 1H)

Synthesis Example 26

Synthesis of Compound 26

Synthesis of Intermediate 26-a

Intermediate 26-a was synthesized in the same manner as in the method of synthesizing Intermediate 2-a in Synthesis Example 2, except that 2-bromo-spirofluorene, instead of 2-bromo-9,9-diphenyl-9H-fluorene, was used. This compound was identified using LC-MS.

$C_{31}H_{21}N$: M+ 407.17

Synthesis of Compound 26

Compound 26 was synthesized in the same manner as in the method of synthesizing Compound 2 in Synthesis Example 2, except that Intermediate 26-a, instead of Intermediate 2-a, was used. This compound was identified using LC-MS and nuclear magnetic resonance (NMR).

$C_{53}H_{34}N_2$: M+ 698.27

1H NMR (CDCl$_3$, 400 MHz) δ (ppm) 7.84 (d, 1H), 7.72 (d, 2H), 7.7 (d, 3H), 7.59 (d, 1H), 7.55 (d, 2H), 7.4 (d, 1H), 7.38 (m, 1H), 7.35 (d, 2H), 7.3-7.2 (m, 6H), 7.19 (m, 2H), 7.16 (m, 2H), 7.08 (m, 1H), 7.01 (m, 2H), 7.0 (m, 1H), 6.75 (s, 1H), 6.62 (m, 1H), 6.6 (s, 1H), 6.58 (d, 1H), 6.46 (d, 2H), 6.2 (d, 1H)

Synthesis Example 27

Synthesis of Compound 27

Synthesis of Intermediate 27-a

Intermediate 27-a was synthesized in the same manner as in the method of synthesizing Intermediate 3-a in Synthesis Example 3, except that 2-bromo-spirofluorene, instead of 2-bromo-9,9-diphenyl-9H-fluorene, was used. This compound was identified using LC-MS.

$C_{37}H_{25}N$: M+ 483.20

Synthesis of Compound 27

Compound 27 was synthesized in the same manner as in the method of synthesizing Compound 1 in Synthesis Example 1, except that Intermediate 27-a, instead of Intermediate 1-a, was used. This compound was identified using LC-MS and nuclear magnetic resonance (NMR).

$C_{55}H_{36}N_2$: M+ 724.29

1H NMR (CDCl$_3$, 400 MHz) δ (ppm) 7.84 (d, 1H), 7.72 (d, 2H), 7.59 (d, 1H), 7.55 (d, 2H), 7.48 (d, 2H), 7.4 (d, 1H), 7.38 (m, 1H), 7.35 (d, 2H), 7.32 (d, 2H), 7.3-7.2 (m, 8H), 7.19 (m, 2H), 7.16 (m, 2H), 7.08 (m, 1H), 7.07 (m, 1H), 7.0 (m, 1H), 6.84 (d, 1H), 6.75 (s, 1H), 6.68 (s, 1H), 6.6 (s, 1H), 6.58 (d, 1H), 6.46 (d, 1H), 6.2 (d, 1H)

Synthesis Example 28

Synthesis of Compound 28

Synthesis of Intermediate 28-a

Intermediate 28-a was synthesized in the same manner as in the method of synthesizing Intermediate 4-a in Synthesis Example 4, except that 2-bromo-spirofluorene, instead of 2-bromo-9,9-diphenyl-9H-fluorene, was used. This compound was identified using LC-MS.

$C_{35}H_{23}N$: M+ 457.18

Synthesis of Compound 28

Compound 28 was synthesized in the same manner as in the method of synthesizing Compound 1 in Synthesis Example 1, except that Intermediate 28-a, instead of Intermediate 1-a, was used. This compound was identified using LC-MS and nuclear magnetic resonance (NMR).

$C_{53}H_{34}N_2$: M+ 698.27

1H NMR (CDCl$_3$, 400 MHz) δ (ppm) 7.84 (d, 1H), 7.72 (d, 2H), 7.59 (d, 1H), 7.55 (d, 3H), 7.51 (d, 1H), 7.44 (d, 1H), 7.4 (d, 1H), 7.38 (m, 1H), 7.35 (d, 2H), 7.3-7.2 (m, 8H), 7.19 (m, 2H), 7.16 (m, 2H), 7.09 (m, 1H), 7.07 (m, 1H), 7.0 (m, 1H), 6.79 (s, 1H), 6.76 (d, 1H), 6.75 (s, 1H), 6.6 (s, 1H), 6.58 (d, 1H), 6.2 (d, 1H)

Synthesis Example 29

Synthesis of Compound 29

Synthesis of Intermediate 29-a

Intermediate 29-a was synthesized in the same manner as in the method of synthesizing Intermediate 5-a in Synthesis Example 5, except that 2-bromo-spirofluorene, instead of 2-bromo-9,9-diphenyl-9H-fluorene, was used. This compound was identified using LC-MS.

$C_{35}H_{23}N$: M+ 457.18

Synthesis of Compound 29

Compound 29 was synthesized in the same manner as in the method of synthesizing Compound 1 in Synthesis Example 1, except that Intermediate 29-a, instead of Intermediate 1-a, was used. This compound was identified using LC-MS and nuclear magnetic resonance (NMR).

$C_{53}H_{34}N_2$: M+ 698.27

1H NMR (CDCl$_3$, 400 MHz) δ (ppm) 7.84 (d, 1H), 7.72 (d, 2H), 7.66 (d, 1H), 7.61 (d, 1H), 7.59 (d, 1H), 7.55 (d, 2H), 7.4 (d, 1H), 7.38 (m, 1H), 7.35 (d, 2H), 7.31 (m, 1H), 7.3-7.2 (m, 8H), 7.19 (m, 2H), 7.16 (m, 3H), 7.15 (m, 1H), 7.08 (m, 1H), 7.0 (m, 1H), 6.75 (s, 1H), 6.6 (s, 1H), 6.58 (d, 1H), 6.55 (d, 1H), 6.2 (d, 1H)

Synthesis Example 30

Synthesis of Compound 30

Synthesis of Compound 30

Compound 30 was synthesized in the same manner as in the method of synthesizing Compound 2 in Synthesis Example 2, except that 2-bromo-9-phenyl-9H-carbazole, instead of 2-bromo-9-naphthalen-1-yl-9H-carbazole, was used. This compound was identified using LC-MS and nuclear magnetic resonance (NMR).

$C_{49}H_{32}N_2$: M+ 648.26

1H NMR (CDCl$_3$, 400 MHz) δ (ppm) 7.84 (d, 1H), 7.72 (d, 2H), 7.59 (d, 1H), 7.55 (d, 2H), 7.4 (d, 1H), 7.38 (m, 1H), 7.35 (d, 2H), 7.3-7.2 (m, 7H), 7.19 (m, 2H), 7.16 (m, 2H), 7.08 (m, 1H), 7.01 (d, 2H), 7.0 (m, 1H), 6.75 (s, 1H), 6.62 (m, 1H), 6.6 (s, 1H), 6.58 (d, 1H), 6.46 (d, 2H), 6.2 (d, 1H)

Synthesis Example 31

Synthesis of Compound 31

Synthesis of Compound 31

Compound 31 was synthesized in the same manner as in the method of synthesizing Compound 7 in Synthesis Example 7, except that Intermediate 25-a, instead of Intermediate 1-a, was used. This compound was identified using LC-MS and nuclear magnetic resonance (NMR).

$C_{61}H_{40}N_2$: M+ 800.32

1H NMR (CDCl$_3$, 400 MHz) δ (ppm) 7.84 (d, 1H), 7.72 (d, 2H), 7.59 (d, 1H), 7.55 (d, 2H), 7.5 (d, 2H), 7.48 (d, 4H), 7.4 (d, 1H), 7.38 (m, 1H), 7.35 (d, 2H), 7.32 (d, 4H), 7.3-7.2 (m, 8H), 7.19 (m, 2H), 7.16 (m, 2H), 7.08 (m, 1H), 7.0 (m, 1H), 6.75 (s, 1H), 6.6 (s, 1H), 6.58 (d, 1H), 6.52 (d, 2H), 6.2 (d, 1H)

Synthesis Example 32

Synthesis of Compound 32

Synthesis of Compound 32

Compound 32 was synthesized in the same manner as in the method of synthesizing Compound 8 in Synthesis Example 8, except that Intermediate 26-a, instead of Intermediate 2-a, was used. This compound was identified using LC-MS and nuclear magnetic resonance (NMR).

$C_{53}H_{34}N_2$: M+ 698.27

1H NMR (CDCl$_3$, 400 MHz) δ (ppm) 7.84 (d, 1H), 7.72 (d, 2H), 7.7 (d, 4H), 7.59 (d, 1H), 7.55 (d, 2H), 7.4 (d, 1H), 7.38 (m, 1H), 7.35 (d, 2H), 7.3-7.2 (m, 5H), 7.19 (m, 2H), 7.16 (m, 2H), 7.08 (m, 1H), 7.01 (d, 2H), 7.0 (m, 1H), 6.75 (s, 1H), 6.62 (m, 1H), 6.6 (s, 1H), 6.58 (d, 1H), 6.46 (d, 2H), 6.2 (d, 1H)

Synthesis Example 33

Synthesis of Compound 33

Synthesis of Compound 33

Compound 33 was synthesized in the same manner as in the method of synthesizing Compound 7 in Synthesis Example 7, except that Intermediate 26-a, instead of Intermediate 1-a, was used. This compound was identified using LC-MS and nuclear magnetic resonance (NMR).

$C_{55}H_{36}N_2$: M+ 724.29

1H NMR (CDCl$_3$, 400 MHz) δ (ppm) 7.84 (d, 1H), 7.72 (d, 2H), 7.59 (d, 1H), 7.55 (d, 2H), 7.5 (d, 2H), 7.48 (d, 2H), 7.4 (d, 1H), 7.38 (m, 1H), 7.35 (d, 2H), 7.32 (d, 2H), 7.3-7.2 (m, 5H), 7.19 (m, 2H), 7.16 (m, 2H), 7.08 (m, 1H), 7.01 (d, 2H), 7.0 (m, 1H), 6.75 (s, 1H), 6.62 (m, 1H), 6.6 (s, 1H), 6.58 (d, 1H), 6.46 (d, 2H), 6.2 (d, 1H)

Synthesis Example 34

Synthesis of Compound 34

Synthesis of Intermediate 34-a

Intermediate 34-a was synthesized in the same manner as in the method of synthesizing Intermediate 6-a in Synthesis Example 6, except that 2-bromo-spirofluorene, instead of 2-bromo-9,9-diphenyl-9H-fluorene, was used. This compound was identified using LC-MS.

$C_{32}H_{20}N_2$: M+ 432.16

Synthesis of Compound 34

Compound 34 was synthesized in the same manner as in the method of synthesizing Compound 1 in Synthesis Example 1, except that Intermediate 34-a, instead of Intermediate 1-a, was used. This compound was identified using LC-MS and nuclear magnetic resonance (NMR).

$C_{50}H_{31}N_3$: M+ 673.25

1H NMR (CDCl$_3$, 400 MHz) δ (ppm) 7.84 (d, 1H), 7.72 (d, 2H), 7.59 (d, 1H), 7.55 (d, 2H), 7.4 (d, 1H), 7.38 (m, 1H), 7.35 (d, 2H), 7.3-7.2 (m, 9H) 7.19 (m, 2H), 7.16 (m, 2H), 7.08 (m, 1H), 7.0 (m, 1H), 6.75 (s, 1H), 6.64 (d, 2H), 6.6 (s, 1H), 6.58 (d, 1H), 6.2 (d, 1H)

Synthesis Example 35

Synthesis of Compound 35

Synthesis of Intermediate 35-a

Intermediate 35-a was synthesized in the same manner as in the method of synthesizing Intermediate 7-a in Synthesis Example 7, except that 2-bromo-spirofluorene, instead of 2-bromo-9,9-diphenyl-9H-fluorene, was used. This compound was identified using LC-MS.

$C_{36}H_{24}N_2$: M+ 484.19

Synthesis of Compound 35

Compound 35 was synthesized in the same manner as in the method of synthesizing Compound 1 in Synthesis Example 1, except that Intermediate 35-a, instead of Intermediate 1-a, was used. This compound was identified using LC-MS and nuclear magnetic resonance (NMR).

$C_{54}H_{35}N_3$: M+ 725.28

1H NMR (CDCl$_3$, 400 MHz) δ (ppm) 8.56 (d, 1H), 7.84 (d, 1H), 7.74 (d, 2H), 7.72 (d, 2H), 7.59 (d, 1H), 7.55 (d, 2H), 7.54 (d, 2H), 7.47 (m, 1H), 7.4 (d, 1H), 7.38 (m, 1H), 7.35 (d, 2H), 7.3-7.2 (m, 7H), 7.19 (m, 2H), 7.16 (m, 2H), 7.08 (m, 1H), 7.0 (m, 1H), 6.98 (m, 1H), 6.75 (s, 1H), 6.6 (s, 1H), 6.58 (d, 1H), 6.55 (d, 2H), 6.2 (d, 1H)

Synthesis Example 36

Synthesis of Compound 36

Synthesis of Intermediate 36-a

Intermediate 36-a was synthesized in the same manner as in the method of synthesizing Intermediate 8-a in Synthesis Example 8, except that 2-bromo-spirofluorene, instead of 2-bromo-9,9-diphenyl-9H-fluorene, was used. This compound was identified using LC-MS.

$C_{36}H_{24}N_2$: M+ 484.19

Synthesis of Compound 36

Compound 36 was synthesized in the same manner as in the method of synthesizing Compound 1 in Synthesis Example 1, except that Intermediate 36-a, instead of Intermediate 1-a, was used. This compound was identified using LC-MS and nuclear magnetic resonance (NMR).

$C_{54}H_{35}N_3$: M+ 725.28

1H NMR (CDCl$_3$, 400 MHz) δ (ppm) 8.81 (s, 1H), 8.55 (d, 1H), 7.97 (d, 1H), 7.84 (d, 1H), 7.72 (d, 2H), 7.59 (d, 1H), 7.55 (d, 2H), 7.44 (m, 2H), 7.4 (d, 1H), 7.38 (m, 1H), 7.35 (d, 2H), 7.3-7.2 (m, 9H), 7.19 (m, 2H), 7.16 (m, 2H), 7.08 (m, 1H), 7.0 (m, 1H), 6.75 (s, 1H), 6.6 (s, 1H), 6.58 (d, 1H), 6.52 (d, 2H), 6.2 (d, 1H)

Synthesis Example 37

Synthesis of Compound 37

Synthesis of Intermediate 37-a

Intermediate 37-a was synthesized in the same manner as in the method of synthesizing Intermediate 9-a in Synthesis Example 9, except that 2-bromo-spirofluorene, instead of 2-bromo-9,9-diphenyl-9H-fluorene, was used. This compound was identified using LC-MS.

$C_{33}H_{21}NS_2$: M+ 495.11

Synthesis of Compound 37

Compound 37 was synthesized in the same manner as in the method of synthesizing Compound 1 in Synthesis Example 1, except that Intermediate 37-a, instead of Intermediate 1-a, was used. This compound was identified using LC-MS and nuclear magnetic resonance (NMR).

$C_{51}H_{32}N_2S_2$; M+ 736.20

1H NMR (CDCl$_3$, 400 MHz) δ (ppm) 7.84 (d, 1H), 7.72 (d, 2H), 7.59 (d, 1H), 7.55 (d, 2H), 7.4 (d, 1H), 7.38 (m, 1H), 7.35 (d, 2H), 7.3-7.2 (m, 8H), 7.19 (m, 2H), 7.16 (m, 2H), 7.08 (m, 1H), 7.0 (m, 3H), 6.75 (s, 1H), 6.6 (s, 1H), 6.58 (d, 1H), 6.5 (d, 1H), 6.2 (d, 1H), 6.0 (d, 1H)

Synthesis Example 38

Synthesis of Compound 38

Synthesis of Intermediate 38-a

Intermediate 38-a was synthesized in the same manner as in the method of synthesizing Intermediate 10-a in Synthesis Example 10, except that 2-bromo-spirofluorene, instead of 2-bromo-9,9-diphenyl-9H-fluorene, was used. This compound was identified using LC-MS.

$C_{36}H_{24}N_2$: M+ 484.19

Synthesis of Compound 38

Compound 38 was synthesized in the same manner as in the method of synthesizing Compound 1 in Synthesis Example 1, except that Intermediate 38-a, instead of Intermediate 1-a, was used. This compound was identified using LC-MS and nuclear magnetic resonance (NMR).

$C_{54}H_{35}N_3$: M+ 725.28

1H NMR (CDCl$_3$, 400 MHz) δ (ppm) 8.65 (d, 2H), 7.84 (d, 1H), 7.72 (d, 2H), 7.6 (d, 2H), 7.59 (d, 1H), 7.55 (d, 2H), 7.4 (d, 1H), 7.38 (m, 1H), 7.35 (d, 2H), 7.3-7.2 (m, 9H), 7.19 (m, 2H), 7.16 (m, 2H), 7.08 (m, 1H), 7.0 (m, 1H), 6.75 (s, 1H), 6.6 (s, 1H), 6.58 (d, 1H), 6.52 (d, 2H), 6.2 (d, 1H)

Synthesis Example 39

Synthesis of Compound 39

Synthesis of Intermediate 39-a

Intermediate 39-a was synthesized in the same manner as in the method of synthesizing Intermediate 11-a in Synthesis Example 11, except that 2-bromo-spirofluorene, instead of 2-bromo-9,9-diphenyl-9H-fluorene, was used. This compound was identified using LC-MS.

$C_{43}H_{29}N$: M+ 559.23

Synthesis of Compound 39

Compound 39 was synthesized in the same manner as in the method of synthesizing Compound 1 in Synthesis Example 1, except that Intermediate 39-a, instead of Intermediate 1-a, was used. This compound was identified using LC-MS and nuclear magnetic resonance (NMR).

$C_{61}H_{40}N_2$: M+ 800.32

1H NMR (CDCl$_3$, 400 MHz) δ (ppm) 7.84 (d, 1H), 7.72 (d, 2H), 7.59 (d, 1H), 7.55 (d, 2H), 7.48 (d, 4H), 7.4 (d, 1H), 7.38 (m, 1H), 7.35 (d, 2H), 7.32 (d, 4H), 7.3-7.2 (m, 9H), 7.19 (m, 2H), 7.16 (m, 2H), 7.08 (m, 1H), 7.06 (s, 1H), 7.0 (m, 1H), 6.75 (s, 1H), 6.64 (s, 2H), 6.6 (s, 1H), 6.58 (d, 1H), 6.2 (d, 1H)

Synthesis Example 40

Synthesis of Compound 40

Compound 40 was synthesized according to Reaction Scheme 9 below:

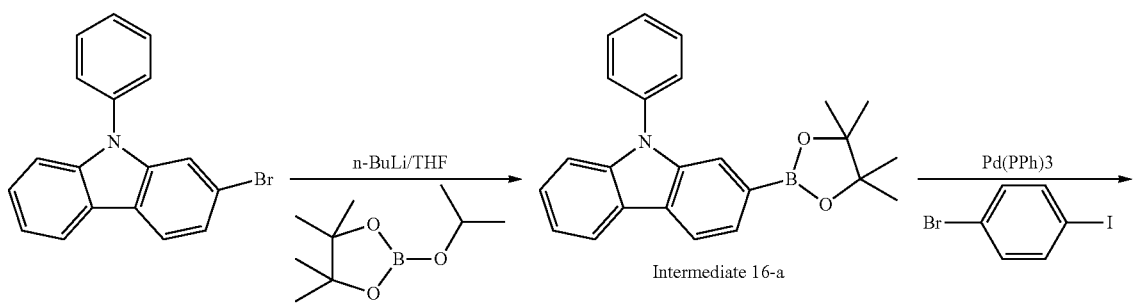

<Reaction Scheme 9>

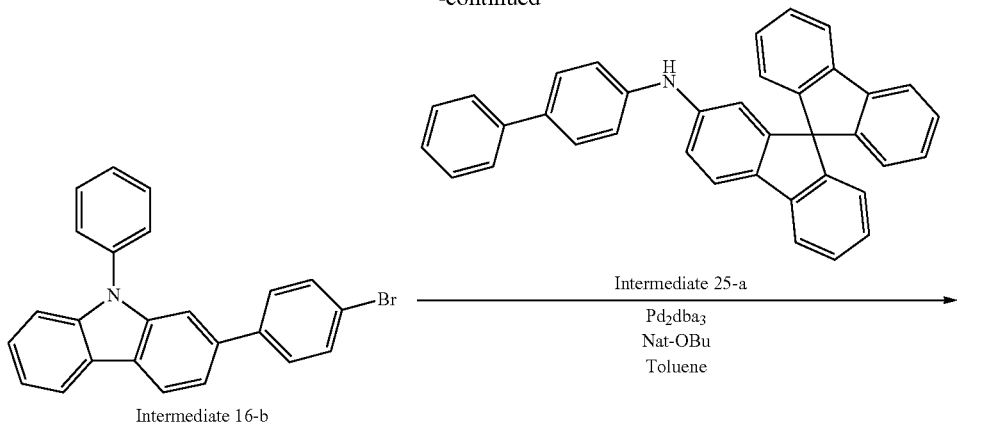

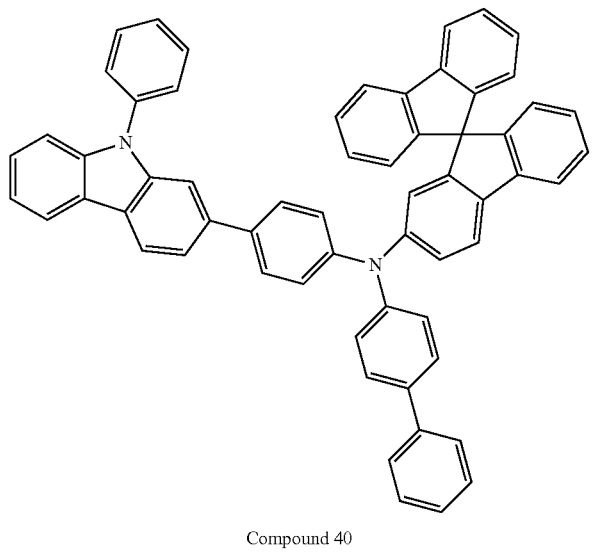

Compound 40

Synthesis of Compound 40

Compound 40 was synthesized in the same manner as in the method of synthesizing Compound 16 in Synthesis Example 16, except that Intermediate 25-a, instead of Intermediate 1-a, was used. This compound was identified using LC-MS and nuclear magnetic resonance (NMR).

$C_{61}H_{40}N_2$: M+ 800.32

1H NMR (CDCl$_3$, 400 MHz) δ (ppm) 7.84 (d, 1H), 7.72 (d, 2H), 7.62 (s, 1H), 7.61 (d, 1H), 7.59 (d, 1H), 7.55 (d, 2H), 7.48 (d, 2H), 7.40 (d, 1H), 7.38 (m, 1H), 7.35 (d, 2H), 7.32 (m, 2H), 7.3-7.2 (m, 12H), 7.19 (m, 2H), 7.16 (m, 2H), 7.08 (m, 1H), 7.0 (m, 1H), 6.75 (s, 1H), 6.58 (d, 1H), 6.52 (d, 4H)

Synthesis Example 41

Synthesis of Compound 41

Synthesis of Compound 41

Compound 41 was synthesized in the same manner as in the method of synthesizing Compound 17 in Synthesis Example 17, except that Intermediate 25-a, instead of Intermediate 1-a, was used. This compound was identified using LC-MS and nuclear magnetic resonance (NMR).

$C_{67}H_{44}N_2$: M+ 876.35

1H NMR (CDCl$_3$, 400 MHz) δ (ppm) 7.84 (d, 1H), 7.72 (d, 2H), 7.62 (s, 1H), 7.61 (d, 1H), 7.59 (d, 1H), 7.55 (d, 2H), 7.5 (d, 2H), 7.48 (d, 4H), 7.40 (d, 1H), 7.38 (m, 1H), 7.35 (d, 2H), 7.32 (m, 4H), 7.3-7.2 (m, 10H), 7.19 (m, 2H), 7.16 (m, 2H), 7.08 (m, 1H), 7.0 (m, 1H), 6.75 (s, 1H), 6.58 (d, 1H), 6.52 (d, 4H)

Synthesis Example 42

Synthesis of Compound 42

Synthesis of Compound 42

Compound 42 was synthesized in the same manner as in the method of synthesizing Compound 16 in Synthesis Example 16, except that Intermediate 27-a, instead of Intermediate 1-a, was used. This compound was identified using LC-MS and nuclear magnetic resonance (NMR).

$C_{61}H_{40}N_2$: M+ 800.32

1H NMR (CDCl$_3$, 400 MHz) δ (ppm) 7.84 (d, 1H), 7.72 (d, 2H), 7.62 (s, 1H), 7.61 (d, 1H), 7.59 (d, 1H), 7.55 (d, 2H), 7.48 (d, 2H), 7.40 (d, 1H), 7.38 (m, 1H), 7.35 (d, 2H), 7.32 (m, 2H), 7.3-7.2 (m, 10H), 7.19 (m, 2H), 7.16 (m, 2H), 7.08

(m, 1H), 7.07 (m, 1H), 7.0 (m, 1H), 6.84 (d, 1H), 6.75 (s, 1H), 6.68 (s, 1H), 6.58 (d, 1H), 6.52 (d, 2H), 6.42 (d, 1H)

Synthesis Example 43

Synthesis of Compound 43

Synthesis of Compound 43

Compound 43 was synthesized in the same manner as in the method of synthesizing Compound 16 in Synthesis Example 16, except that Intermediate 28-a, instead of Intermediate 1-a, was used. This compound was identified using LC-MS and nuclear magnetic resonance (NMR).

$C_{59}H_{38}N_2$: M+ 774.30

1H NMR (CDCl$_3$, 400 MHz) δ (ppm) 7.84 (d, 1H), 7.72 (d, 2H), 7.62 (s, 1H), 7.61 (d, 1H), 7.59 (d, 1H), 7.55 (d, 3H), 7.51 (d, 1H), 7.44 (d, 1H), 7.40 (d, 1H), 7.38 (m, 1H), 7.35 (d, 2H), 7.3-7.2 (m, 10H), 7.19 (m, 2H), 7.16 (m, 2H), 7.09 (m, 1H), 7.08 (m, 1H), 7.0 (m, 1H), 6.79 (s, 1H), 6.76 (d, 1H), 6.75 (s, 1H), 6.58 (d, 1H), 6.52 (d, 2H)

Synthesis Example 44

Synthesis of Compound 44

Synthesis of Compound 44

Compound 44 was synthesized in the same manner as in the method of synthesizing Compound 16 in Synthesis Example 16, except that Intermediate 35-a, instead of Intermediate 1-a, was used. This compound was identified using LC-MS and nuclear magnetic resonance (NMR).

$C_{60}H_{39}N_3$: M+ 801.31

1H NMR (CDCl$_3$, 400 MHz) δ (ppm) 8.56 (d, 1H), 7.84 (d, 1H), 7.74 (d, 2H), 7.72 (d, 2H), 7.62 (s, 1H), 7.61 (d, 1H), 7.59 (d, 1H), 7.55 (d, 2H), 7.54 (d, 1H), 7.47 (m, 1H), 7.40 (d, 1H), 7.38 (m, 1H), 7.35 (d, 2H), 7.3-7.2 (m, 9H), 7.19 (m, 2H), 7.16 (m, 2H), 7.08 (m, 1H), 7.0 (m, 1H), 6.98 (m, 1H), 6.75 (s, 1H), 6.58 (d, 1H), 6.55 (d, 2H), 6.52 (d, 2H)

Synthesis Example 45

Synthesis of Compound 45

Synthesis of Intermediate 45-a

Intermediate 45-a was synthesized in the same manner as in the method of synthesizing Intermediate 1-a in Synthesis Example 1-a, except that 4'-amino-biphenyl-4-carbonitrile, instead of biphenyl-4-ylamine, and 2-bromo-spirofluorene, instead of 2-bromo-9,9-diphenyl-9H-fluorene, was used. This compound was identified using LC-MS.

$C_{38}H_{24}N_2$: M+ 508.19

Synthesis of Compound 45

Compound 45 was synthesized in the same manner as in the method of synthesizing Compound 16 in Synthesis Example 16, except that Intermediate 45-a, instead of Intermediate 1-a, was used. This compound was identified using LC-MS and nuclear magnetic resonance (NMR).

$C_{60}H_{39}N_3$: M+ 825.31

1H NMR (CDCl$_3$, 400 MHz) δ (ppm) 7.84 (d, 1H), 7.72 (d, 2H), 7.66 (d, 2H), 7.62 (s, 1H), 7.61 (d, 1H), 7.59 (d, 1H), 7.57 (d, 2H), 7.55 (d, 2H), 7.40 (d, 1H), 7.38 (m, 1H), 7.35 (d, 2H), 7.3-7.2 (m, 11H), 7.19 (m, 2H), 7.16 (m, 2H), 7.08 (m, 1H), 7.0 (m, 1H), 6.75 (s, 1H), 6.58 (d, 1H), 6.52 (d, 4H)

Synthesis Example 46

Synthesis of Compound 46

Synthesis of Compound 46

Compound 46 was synthesized in the same manner as in the method of synthesizing Compound 16 in Synthesis Example 16, except that Intermediate 36-a, instead of Intermediate 1-a, was used. This compound was identified using LC-MS and nuclear magnetic resonance (NMR).

$C_{60}H_{39}N_3$: M+ 801.31

1H NMR (CDCl$_3$, 400 MHz) δ (ppm) 8.81 (s, 1H), 8.55 (d, 1H), 7.97 (d, 1H), 7.84 (d, 1H), 7.72 (d, 2H), 7.62 (s, 1H), 7.61 (d, 1H), 7.59 (d, 1H), 7.55 (d, 2H), 7.44 (m, 1H), 7.40 (d, 1H), 7.38 (m, 1H), 7.35 (d, 2H), 7.3-7.2 (m, 11H), 7.19 (m, 2H), 7.16 (m, 2H), 7.08 (m, 1H), 7.0 (m, 1H), 6.75 (s, 1H), 6.58 (d, 1H), 6.52 (d, 4H)

Synthesis Example 47

Synthesis of Compound 47

Synthesis of Compound 47

Compound 47 was synthesized in the same manner as in the method of synthesizing Compound 16 in Synthesis Example 16, except that Intermediate 26-a, instead of Intermediate 1-a, was used. This compound was identified using LC-MS and nuclear magnetic resonance (NMR).

$C_{55}H_{36}N_2$: M+ 724.29

1H NMR (CDCl$_3$, 400 MHz) δ (ppm) 7.84 (d, 1H), 7.72 (d, 2H), 7.62 (s, 1H), 7.61 (d, 1H), 7.59 (d, 1H), 7.55 (d, 2H), 7.40 (d, 1H), 7.38 (m, 1H), 7.35 (d, 2H), 7.3-7.2 (m, 9H), 7.19 (m, 2H), 7.16 (m, 2H), 7.08 (m, 1H), 7.01 (d, 2H), 7.0 (m, 1H), 6.75 (s, 1H), 6.62 (m, 1H), 6.58 (d, 1H), 6.52 (d, 2H). 6.46 (d, 2H)

Synthesis Example 48

Synthesis of Compound 48

Synthesis of Compound 48

Compound 48 was synthesized in the same manner as in the method of synthesizing Compound 24 in Synthesis Example 24, except that Intermediate 25-a, instead of Intermediate 1-a, was used. This compound was identified using LC-MS and nuclear magnetic resonance (NMR).

$C_{65}H_{42}N_2$: M+ 850.33

1H NMR (CDCl$_3$, 400 MHz) δ (ppm) 7.84 (d, 1H), 7.72 (d, 2H), 7.7 (d, 4H), 7.62 (s, 1H), 7.61 (d, 1H), 7.59 (d, 1H), 7.55 (d, 2H), 7.48 (d, 2H), 7.40 (d, 1H), 7.38 (m, 1H), 7.35 (d, 2H), 7.32 (d, 2H), 7.3-7.2 (m, 10H), 7.19 (m, 2H), 7.16 (m, 2H), 7.08 (m, 1H), 7.0 (m, 1H), 6.75 (s, 1H), 6.58 (d, 1H), 6.52 (d, 4H)

Example 1

To manufacture an anode, a substrate with deposited ITO/Ag/ITO layers (70/1000/70 Å) was cut to a size of 50 mm×50 mm×0.5 mm and then ultrasonicated in isopropyl alcohol and pure water each for five minutes, and then cleaned by irradiation of ultraviolet rays for 30 minutes and exposure to ozone. The resulting glass substrate was loaded into a vacuum deposition device.

2-TNATA was vacuum-deposited on the anode to form an HIL having a thickness of 600 Å, and then Compound 1 was vacuum-deposited on the HIL to form a HTL having a thickness of 1000 Å.

Then, CBP (host) and Ir(ppy)₃ (green phosphorescent dopant) were co-deposited in a weight ratio of 91:9 on the HTL, to form an EML with a thickness of about 250 Å.

Then, BCP was deposited on the EML to form a HBL having a thickness of about 50 Å, and then Alq₃ was deposited on the HBL to form an ETL having a thickness of about 350 Å. Then, LiF was deposited on the ETL to form an EIL having a thickness of about. Mg and Ag were deposited in a weight ratio of about 90:10 on the EIL to form a cathode having a thickness of about 120 Å, thereby completing the manufacture of an organic light-emitting device.

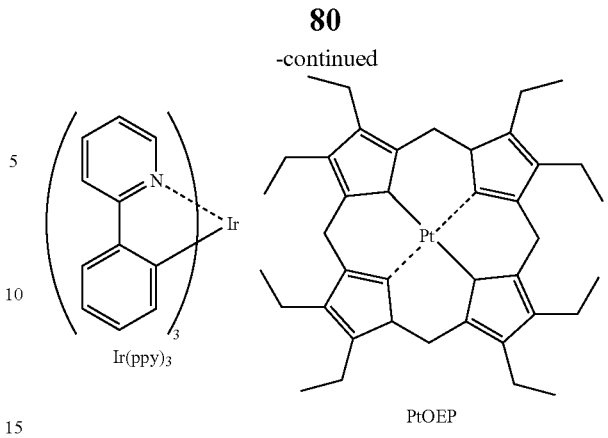

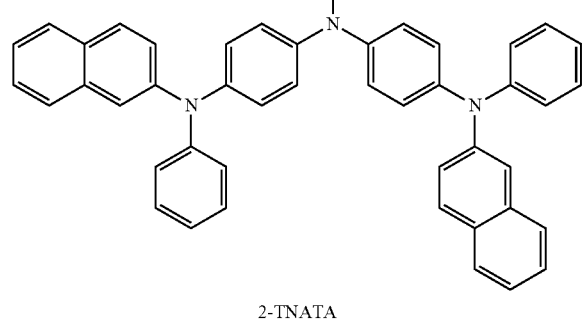

2-TNATA

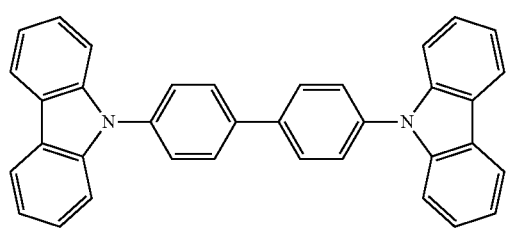

CBP

Example 2

To manufacture an anode, a substrate with deposited ITO/Ag/ITO layers (70/1000/70 Å) was cut to a size of 50 mm×50 mm×0.5 mm and then ultrasonicated in isopropyl alcohol and pure water each for five minutes, and then cleaned by irradiation of ultraviolet rays for 30 minutes and exposure to ozone. The resulting glass substrate was loaded into a vacuum deposition device.

2-TNATA was vacuum-deposited on the anode to form an HIL having a thickness of 600 Å, and then Compound 1 was deposited on the HIL to form a HTL having a thickness of 1350 Å.

CBP (host) and PtOEP (red phosphorescent dopant) were co-deposited in a weight ratio of about 91:9 on the HTL to form an EML having a thickness of about 250 Å.

Then, BCP was deposited on the EML to form a HBL having a thickness of about 50 Å, and then Alq₃ was deposited on the HBL to form an ETL having a thickness of about 350 Å. Then, LiF was deposited on the ETL to form an EIL having a thickness of about. Mg and Ag were deposited in a weight ratio of about 90:10 on the EIL to form a cathode having a thickness of about 120 Å, thereby completing the manufacture of an organic light-emitting device.

Example 3

An organic light-emitting device was manufactured in the same manner as in Example 1, except that Compound 3, instead of Compound 1, was used to form the HTL.

Example 4

An organic light-emitting device was manufactured in the same manner as in Example 2, except that Compound 3, instead of Compound 1, was used to form the HTL.

Example 5

An organic light-emitting device was manufactured in the same manner as in Example 1, except that Compound 15, instead of Compound 1, was used to form the HTL.

Example 6

An organic light-emitting device was manufactured in the same manner as in Example 2, except that Compound 15, instead of Compound 1, was used to form the HTL.

Example 7

An organic light-emitting device was manufactured in the same manner as in Example 1, except that Compound 16, instead of Compound 1, was used to form the HTL.

Example 8

An organic light-emitting device was manufactured in the same manner as in Example 2, except that Compound 16, instead of Compound 1, was used to form the HTL.

Example 9

An organic light-emitting device was manufactured in the same manner as in Example 1, except that Compound 39, instead of Compound 1, was used to form the HTL.

Example 10

An organic light-emitting device was manufactured in the same manner as in Example 2, except that Compound 39, instead of Compound 1, was used to form the HTL.

Comparative Example 1

An organic light-emitting device was manufactured in the same manner as in Example 2, except that Compound A, instead of Compound 1, was used to form the ETL.

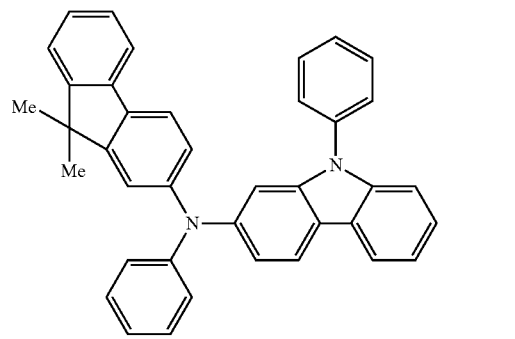

<Compound A>

Comparative Example 2

An organic light-emitting device was manufactured in the same manner as in Example 1, except that Compound A, instead of Compound 1, was used to form the HTL.

Comparative Example 3

An organic light-emitting device was manufactured in the same manner as in Example 2, except that Compound B, instead of Compound 1, was used to form the HTL.

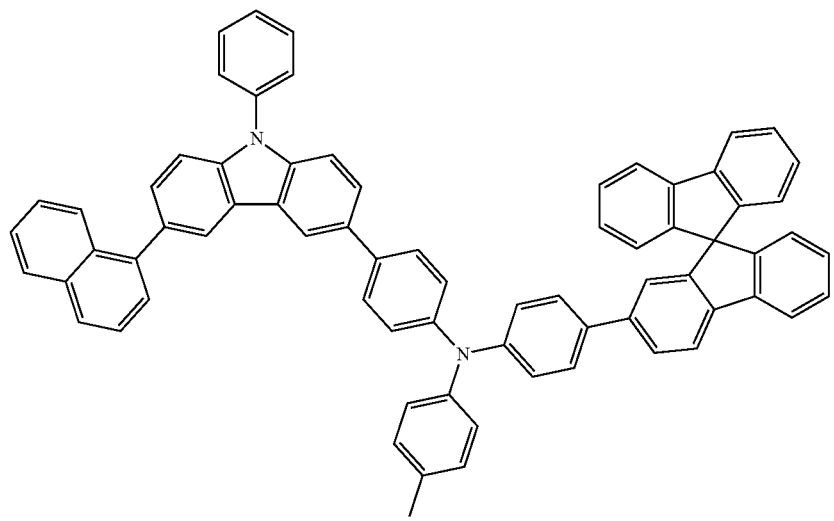

<Compound B>

Comparative Example 4

An organic light-emitting device was manufactured in the same manner as in Example 2, except that Compound B, instead of Compound 1, was used to form the HTL.

Evaluation Example 1

Driving voltages, efficiencies, and color purities of the organic light-emitting devices of Examples 1 to 10 and Comparative Examples 1 to 4 were measured using the following methods. The results are shown in Table 1 below.

Color coordinates were measured using a PR650 (Spectroscan) Source Measurement Unit. (available from Photo Research, Inc.) with a supply of power using a Kethley Source-Measure Unit (SMU 236).

Luminances were measured using a PR650 (Spectroscan) Source Measurement Unit. (available from Photo Research, Inc.) with a supply of power using a Kethley Source-Measure Unit (SMU 236).

Efficiencies were measured using a PR650 (Spectroscan) Source Measurement Unit. (available from Photo Research, Inc.) with a supply of power using a Kethley Source-Measure Unit (SMU 236).

In Table 1, T95 lifetime indicates the time taken until an initial luminance (assumed as 100%) measured at a current density of about 10 mA/cm$^2$ is reduced to 95%.

TABLE 1

|  | HIL material | Driving voltage (V) | Current density (mA/cm$^2$) | Luminance (cd/m$^2$) | Efficiency (cd/A) | Emission color | Half-lifespan (hr @ 100 mA/cm$^2$) |
| --- | --- | --- | --- | --- | --- | --- | --- |
| Example 1 | Compound 1 | 5.6 | 10 | 6,032 | 60.3 | Green | 78 |
| Example 2 | Compound 1 | 5.49 | 10 | 2,883 | 28.8 | Red | 134 |
| Example 3 | Compound 3 | 5.4 | 10 | 5,923 | 59.2 | Green | 75 |
| Example 4 | Compound 3 | 5.2 | 10 | 2,997 | 30.0 | Red | 136 |
| Example 5 | Compound 15 | 5.5 | 10 | 5,992 | 59.9 | Green | 78 |
| Example 6 | Compound 15 | 5.4 | 10 | 2,807 | 28.1 | Red | 131 |
| Example 7 | Compound 16 | 5.3 | 10 | 5,892 | 58.9 | Green | 76 |
| Example 8 | Compound 16 | 5.6 | 10 | 3,009 | 30.1 | Red | 127 |
| Example 9 | Compound 39 | 5.3 | 10 | 6,102 | 61.0 | Green | 79 |
| Example 10 | Compound 39 | 5.4 | 10 | 2,798 | 28.0 | Red | 128 |
| Comparative Example 1 | Compound A | 6.8 | 10 | 4,766 | 47.7 | Green | 65 |
| Comparative Example 2 | Compound A | 7.12 | 10 | 2,257 | 25.7 | Red | 101 |
| Comparative Example 3 | Compound B | 6.5 | 10 | 4,233 | 42.3 | Green | 70 |
| Comparative Example 4 | Compound B | 7.01 | 10 | 2,232 | 22.3 | Red | 92 |

Referring to Table 1, the organic light-emitting devices of Examples 1 to 10 were found to have lower driving voltages, higher efficiencies, and higher color purities, than the organic light-emitting devices of Comparative Examples 1 to 4.

As described above, according to the one or more embodiments, an organic light-emitting device including the amine-based compound of Formula 1 Above may have a low driving voltage, a high efficiency, and high color purity.

While the present embodiments have been particularly shown and described with reference to example embodiments thereof, it will be understood by those of ordinary skill in the art that various changes in form and details may be made therein without departing from the spirit and scope of the present embodiments as defined by the following claims.

What is claimed is:

1. A compound represented by Formula 1 below:

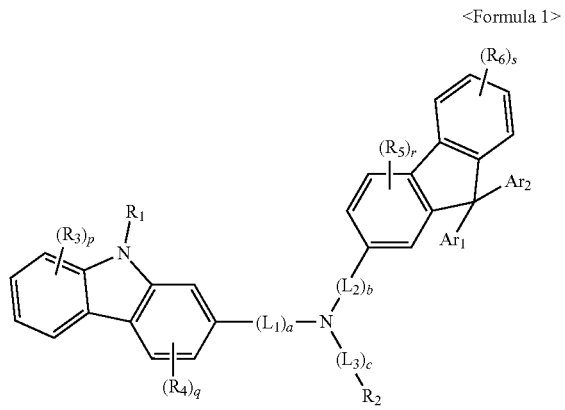

<Formula 1> wherein, in Formula 1, $Ar_1$ and $Ar_2$ are each independently a substituted or unsubstituted $C_6$-$C_{30}$ aryl group, and $Ar_1$ and $Ar_2$ are optionally linked to each other via a single bond;

$L_1$ to $L_3$ are each independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{30}$ arylene group, or a substituted or unsubstituted $C_2$-$C_{60}$ hetero arylene group;

a, b, and c are each independently an integer from 0 to 5;

$R_1$ to $R_6$ are each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_3$-$C_{60}$ heterocycloalkyl group, a substituted or unsubstituted $C_3$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), or —Si($Q_3$)($Q_4$)($Q_5$), wherein $Q_1$ to $Q_5$ are each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_3$-$C_{60}$ heterocycloalkyl group, a substituted or unsubstituted $C_3$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

p and s are each independently an integer from 1 to 4; and q and r are each independently an integer from 1 to 3.

2. The compound of claim 1, wherein $Ar_1$ and $Ar_2$ are each independently, a substituted or unsubstituted phenyl group, a substituted or unsubstituted naphthyl group, or a substituted or unsubstituted anthryl group.

3. The compound of claim 1, wherein $Ar_1$ and $Ar_2$ are linked to each other via a single bond.

4. The compound of claim 1, wherein $L_1$ to $L_3$ are each independently one of a phenylene group, a naphthylene group, anthrylene group, a pyridinylene group, a pyrimidinylene group, a triazinylene group, and a thiophenylene group; and a phenylene group, a naphthylene group, an anthrylene group, a pyridinylene group, a pyrimidinylene group, a triazinylene group, and a thiophenylene group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group.

5. The compound of claim 1, wherein a is an integer from 1 to 5.

6. The compound of claim 1, wherein a, b, and c are each independently 0, 1, or 2.

7. The compound of claim 1, wherein a is 1 or 2, and b is 0.

8. The compound of claim 1, wherein $R_1$ and $R_2$ are each independently one of a phenyl group, a naphthyl group, an anthryl group, a pyridinyl group, a pyrimidinyl group, a triazinyl group, and a thiophenyl group; and a phenyl group, a naphthyl group, an anthryl group, a pyridinyl group, a pyrimidinyl group, a triazinyl group, and a thiophenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group.

9. The compound of claim 1, wherein the compound is represented by Formula 1A or 1B below:

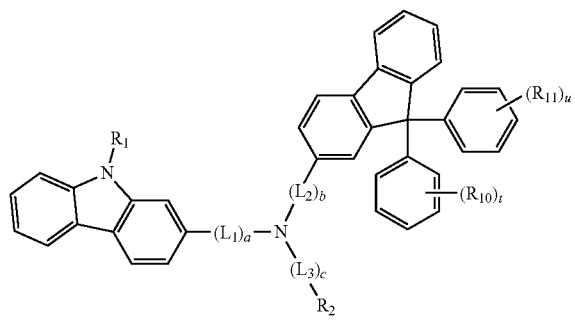

<Formula 1A>

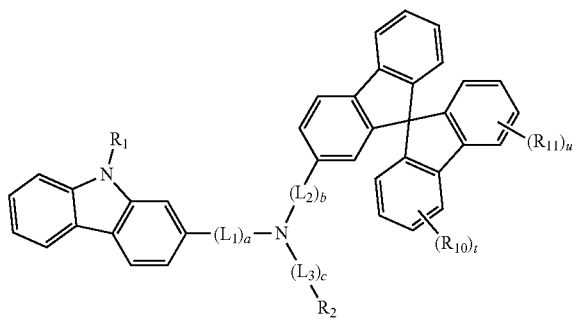

<Formula 1B>

Wherein, in Formulae 1A and 1B, $L_1$ to $L_3$, a, b, c, $R_1$, and $R_2$ are as defined in claim 1; $R_{10}$ and $R_{11}$ are as defined in conjunction with $R_1$ in claim 1; and t and u are each independently an integer from 1 to 4.

10. The compound of claim 9, wherein $L_1$ to $L_3$ are each independently one of a phenylene group, a naphthylene group, an anthrylene group, a pyridinylene group, a pyrimidinylene group, a triazinylene group, and a thiophenylene group; and a phenylene group, a naphthylene group, an anthrylene group, a pyridinylene group, a pyrimidinylene group, a triazinylene group, and a thiophenylene group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group.

11. The compound of claim 9, wherein a is an integer from 1 to 5.

12. The compound of claim 9, wherein a, b, and c are each independently 0, 1, or 2.

13. The compound of claim 9, wherein $R_1$ and $R_2$ are each independently one of a phenyl group, a naphthyl group, an anthryl group, a pyridinyl group, a pyrimidinyl group, a triazinyl group, and a thiophenyl group; a phenyl group, a naphthyl group, an anthryl group, a pyridinyl group, a pyrimidinyl group, a triazinyl group, and a thiophenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a pyridinyl group, a pyrimidinyl group, a triazinyl group, and a thiophenyl group.

14. The compound of claim 1, wherein compound is represented by one of Formulae 1A(1), 1A(2), 1B(1), and 1B(2) below:

<Formula 1A(1)>

<Formula 1A(2)>

<Formula 1B(1)>

<Formula 1B(2)> wherein, in Formulae 1A(1), 1A(2), 1B(1), and 1B(2), $L_3$, c, $R_1$, and $R_2$ are as defined in claim 1; $R_{10}$ and $R_{11}$ are as defined in conjunction with $R_1$ in claim 1; and t and u are each independently an integer from 1 to 4.

15. The compound of claim 1, wherein the compound is one of Compounds 1 to 48 below:

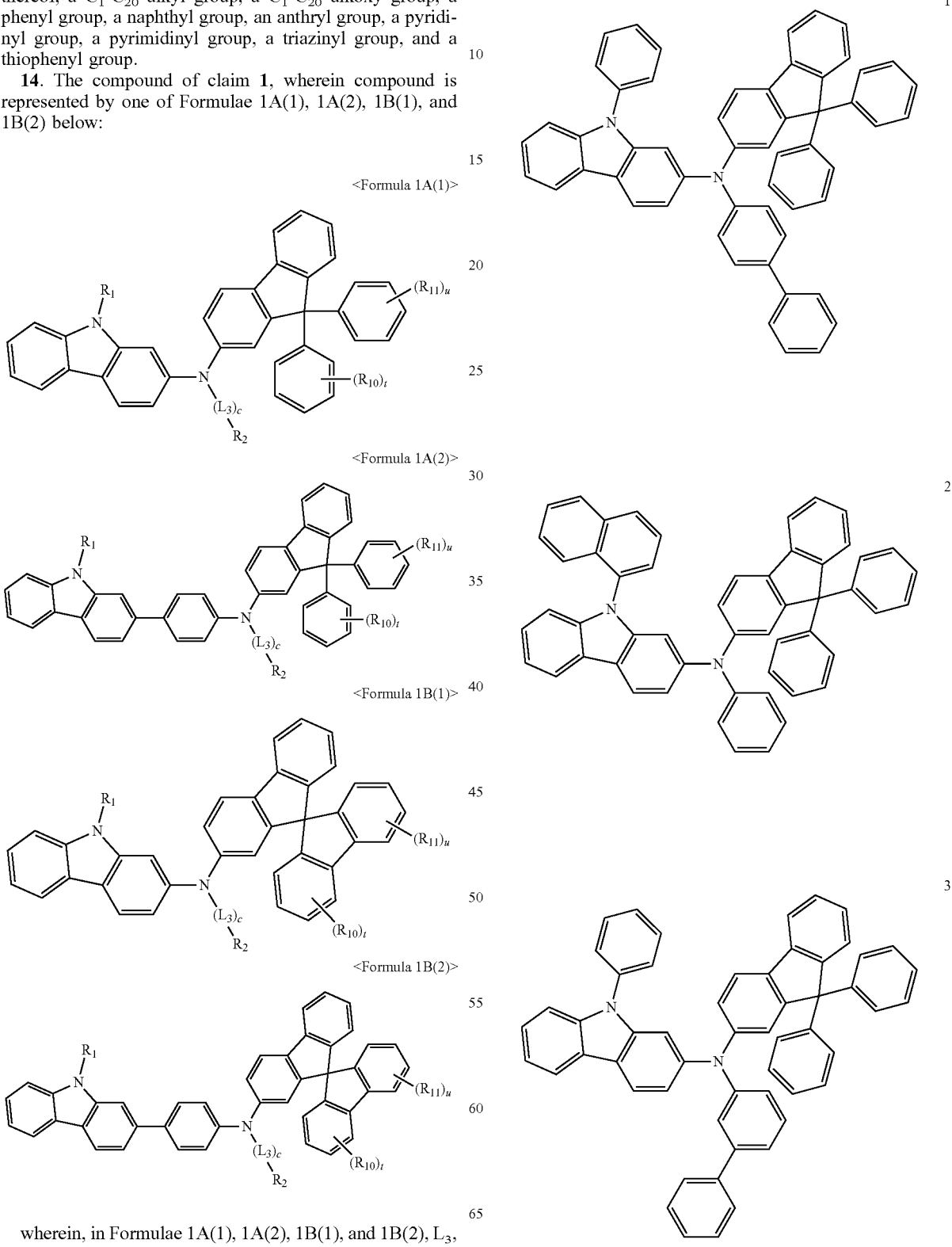

-continued
4
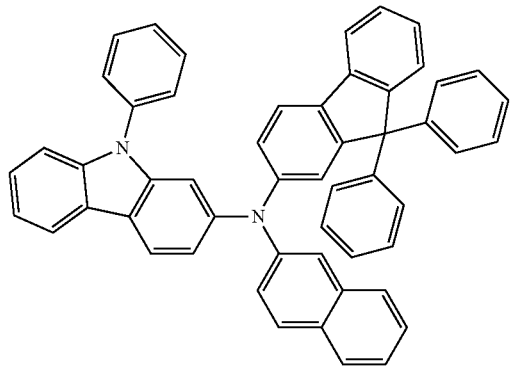
5
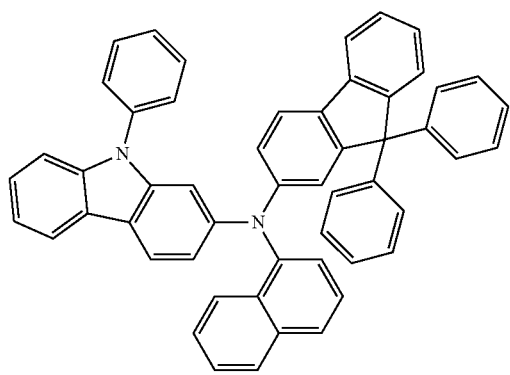
6
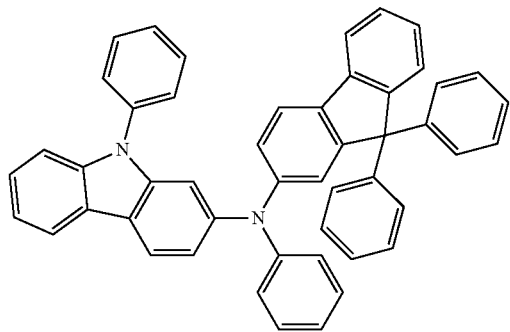
7
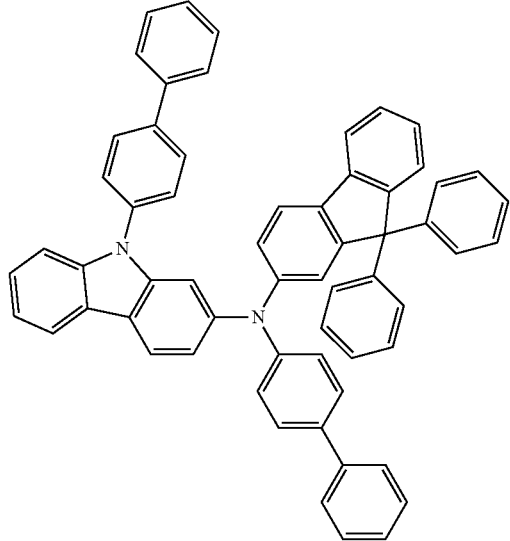
-continued
8
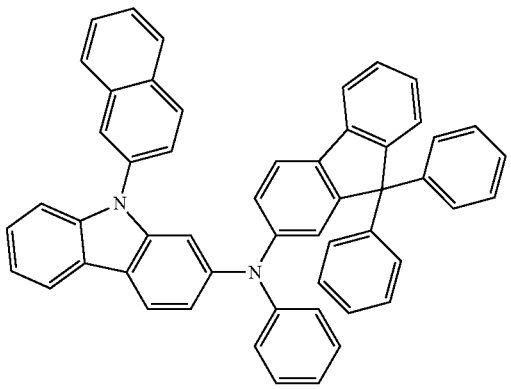
9
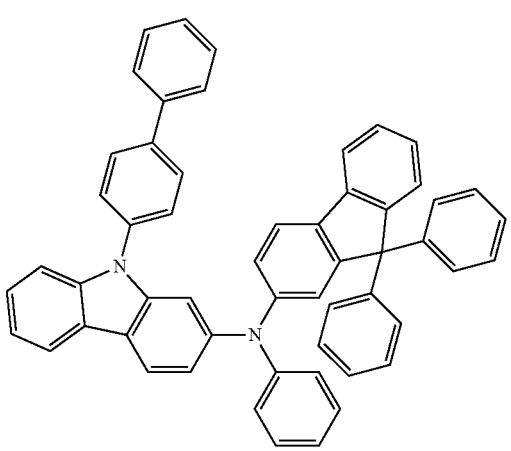
10
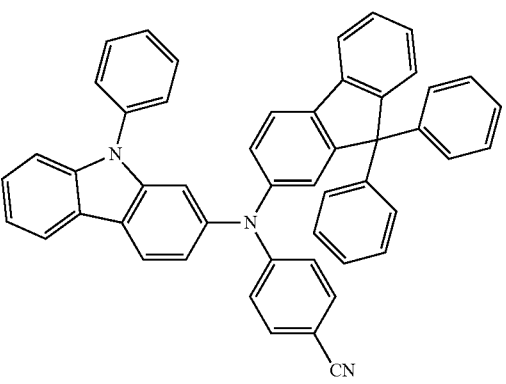
11
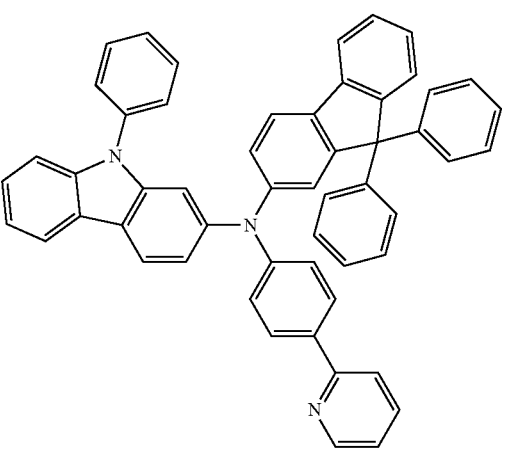

-continued
12
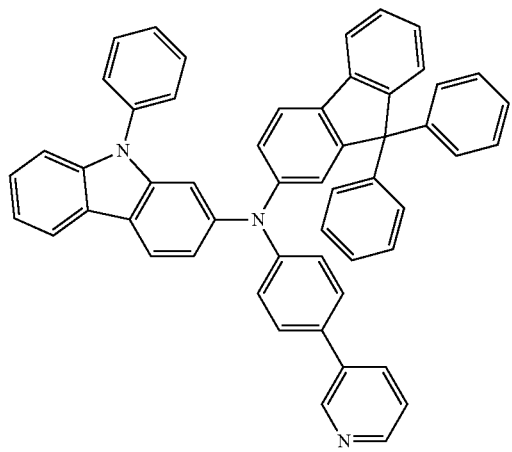
15
-continued
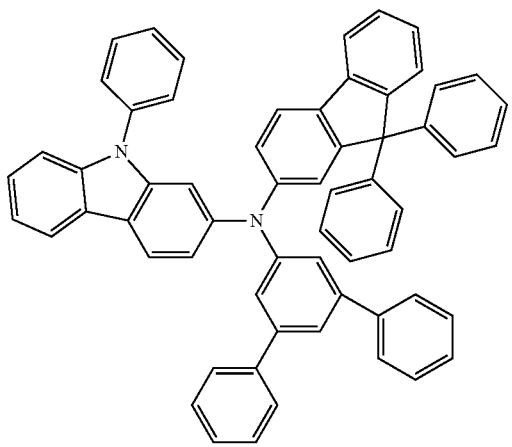
13
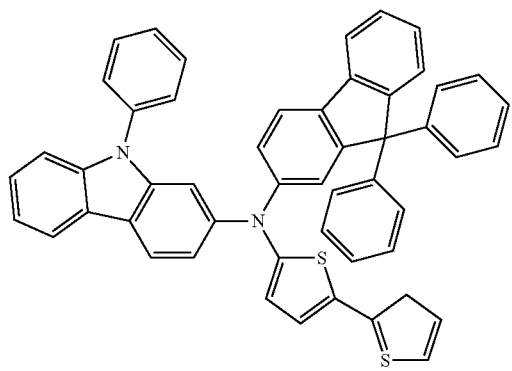
16
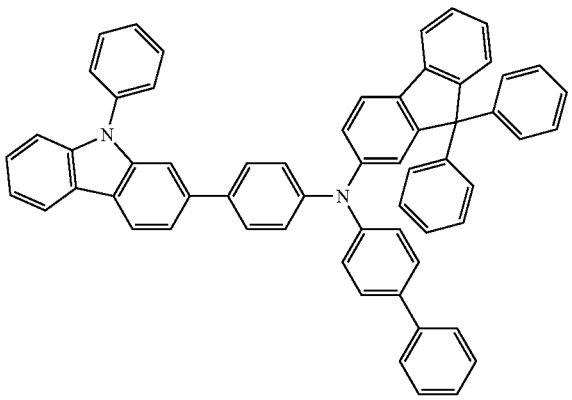
14
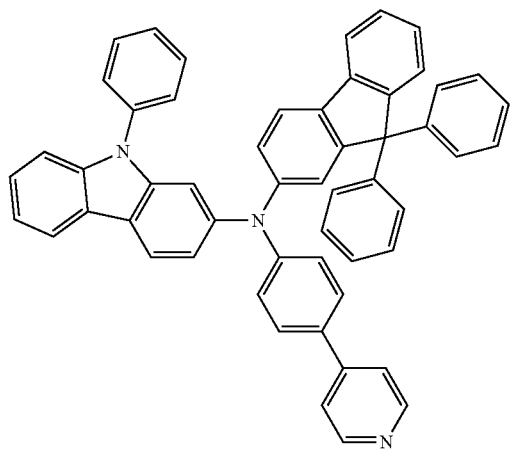
17
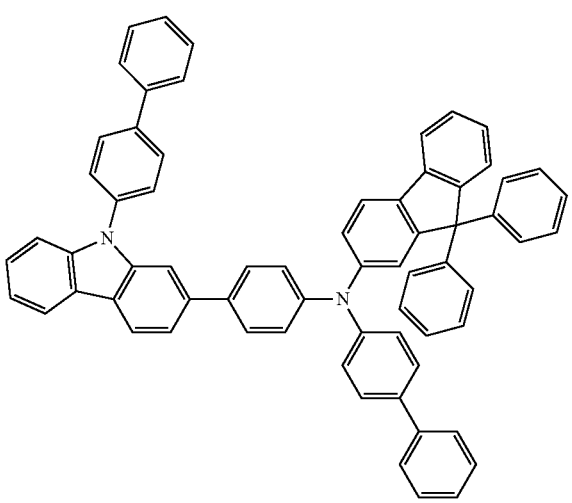

18
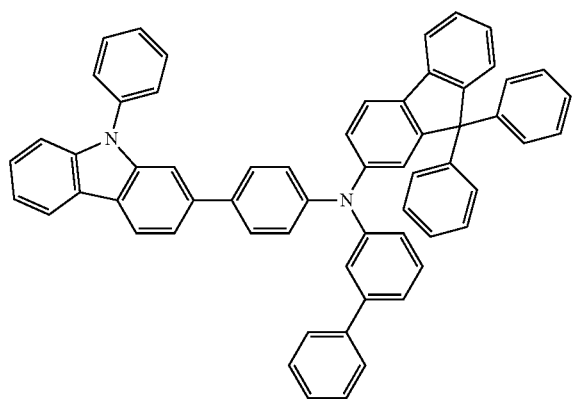
19
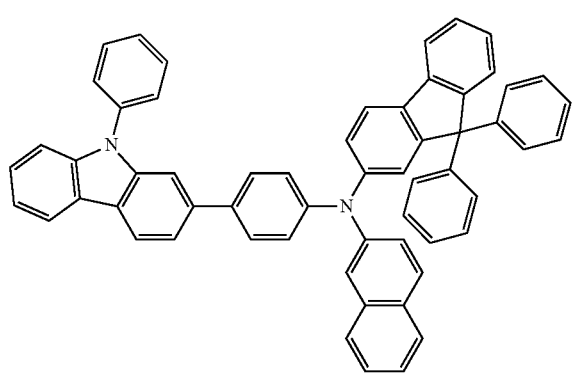
20
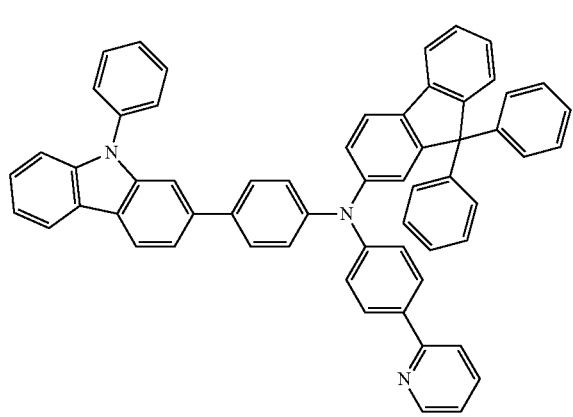
21
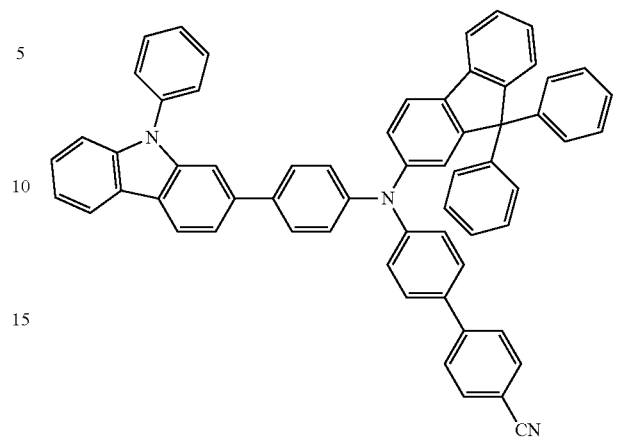
22
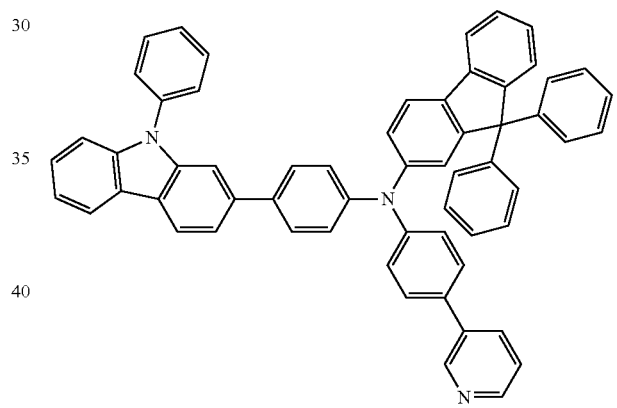
23
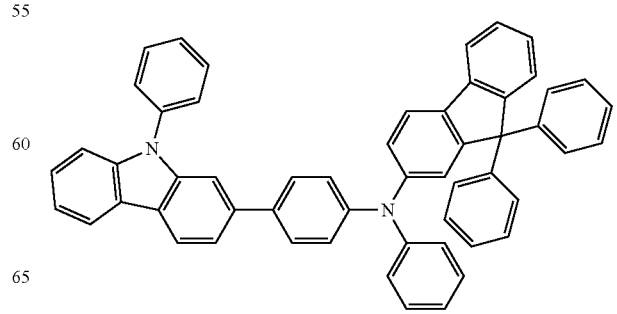

24
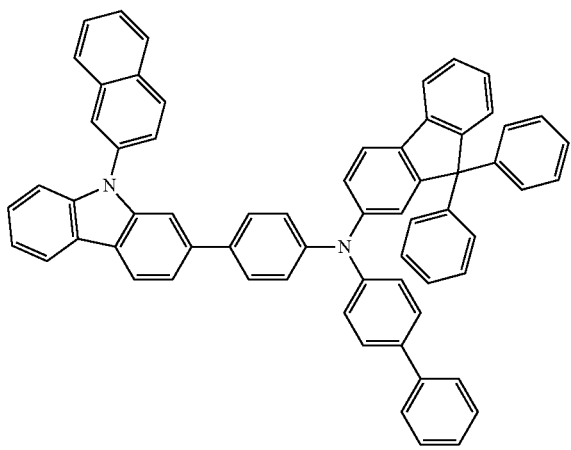
25
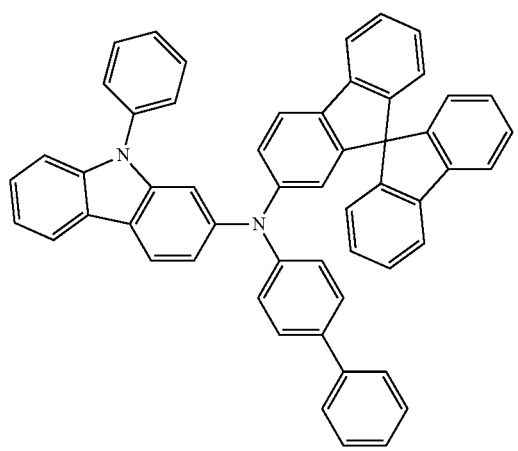
26
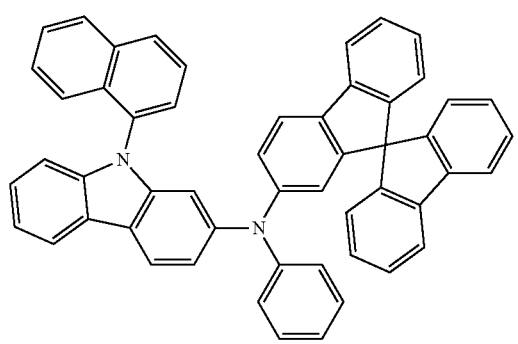
27
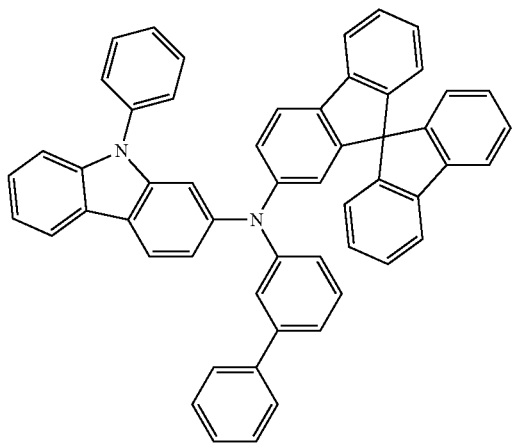
28
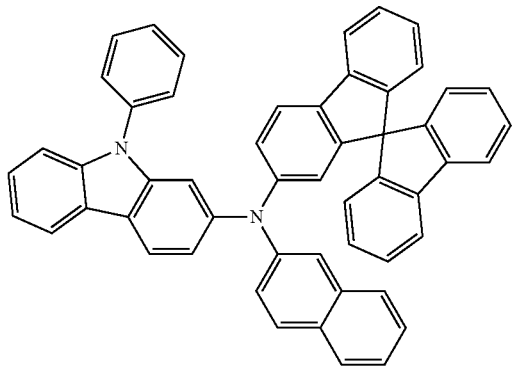
29
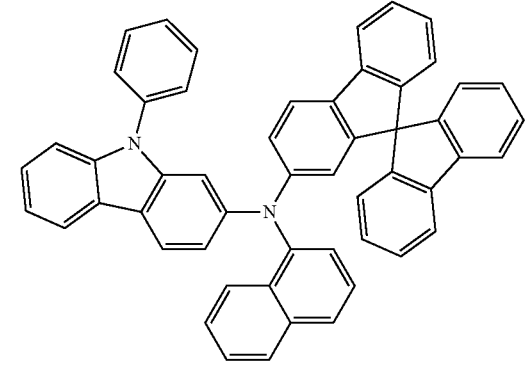
30

31
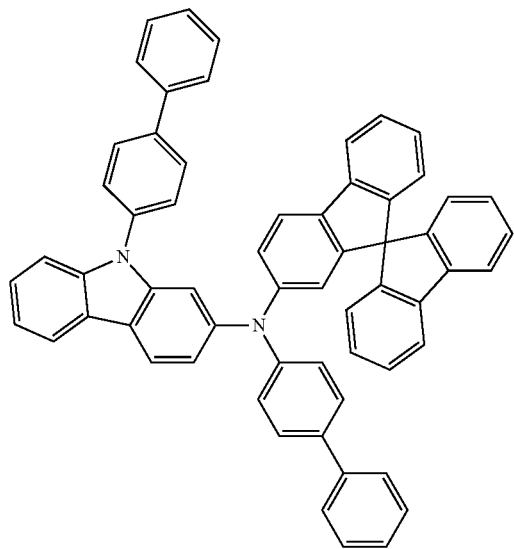
32
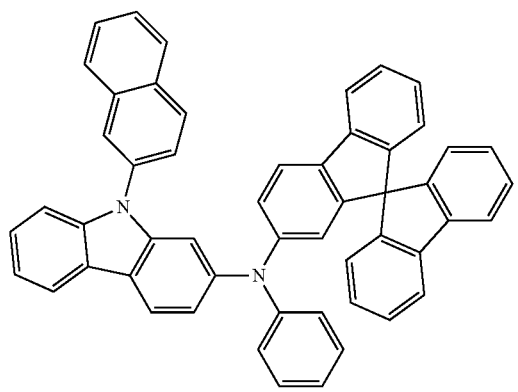
33
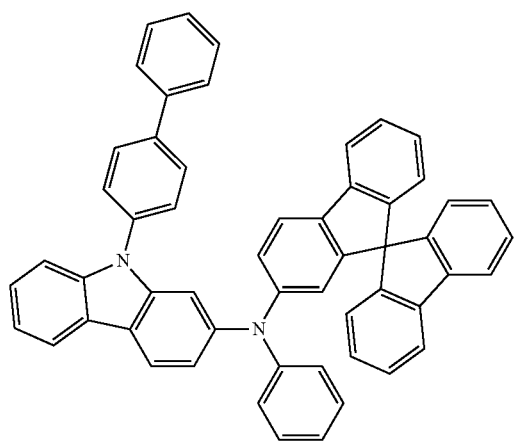
34
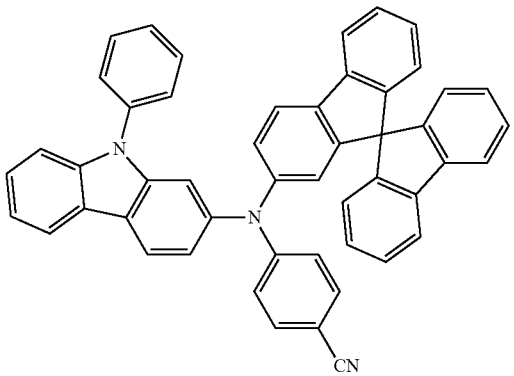
35
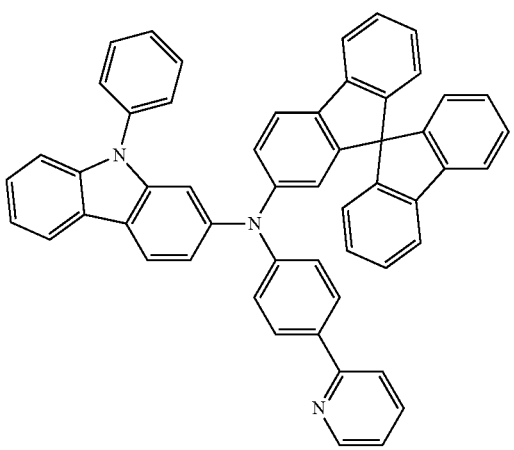
36
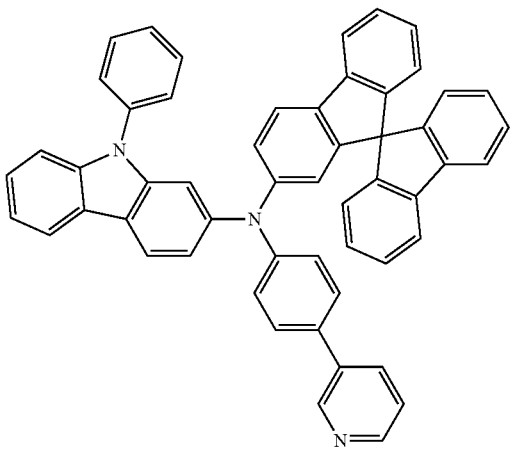
37
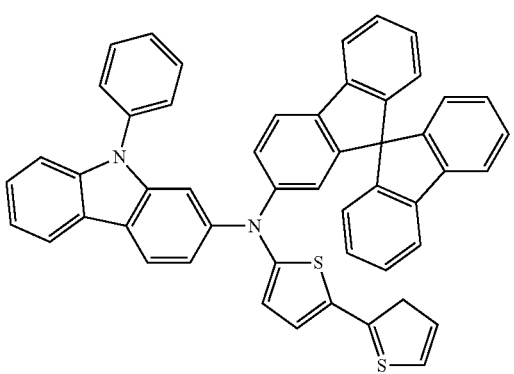

38
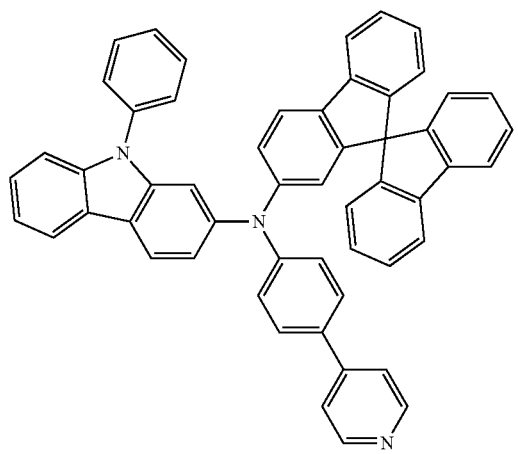
39
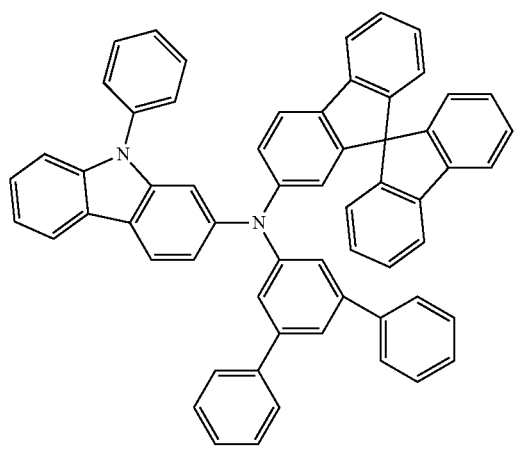
40
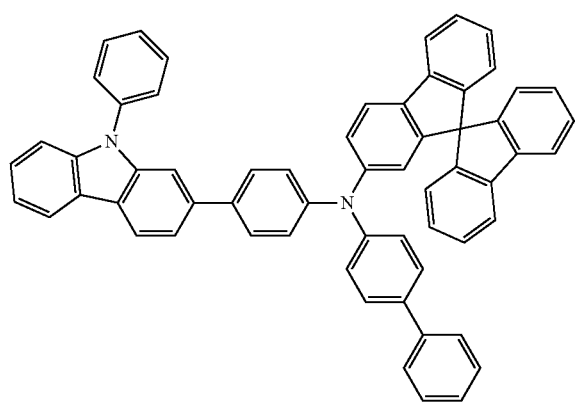
41
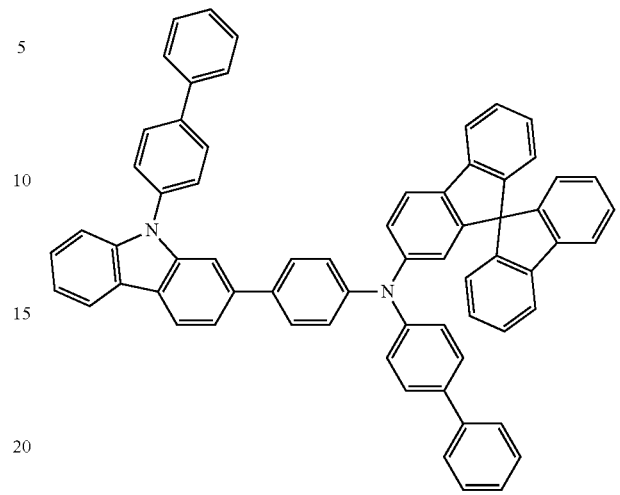
42
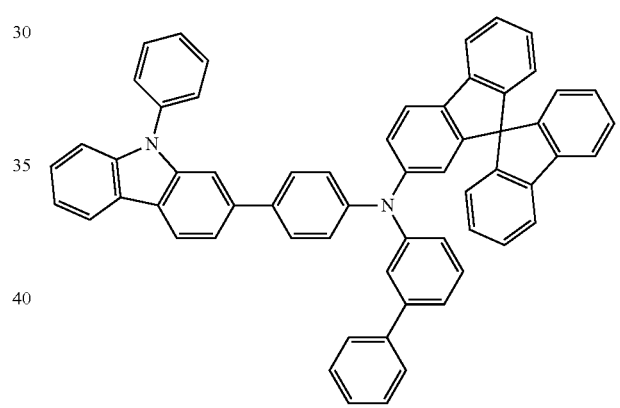
43
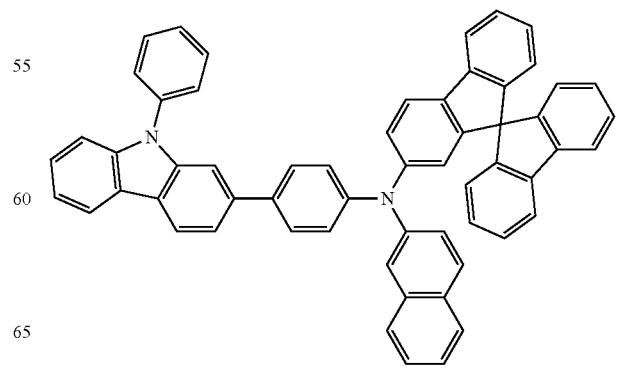

44

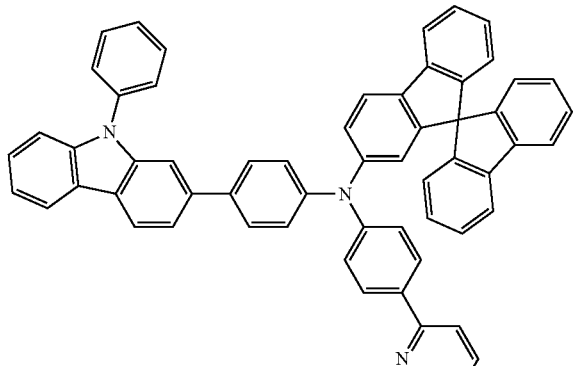

45

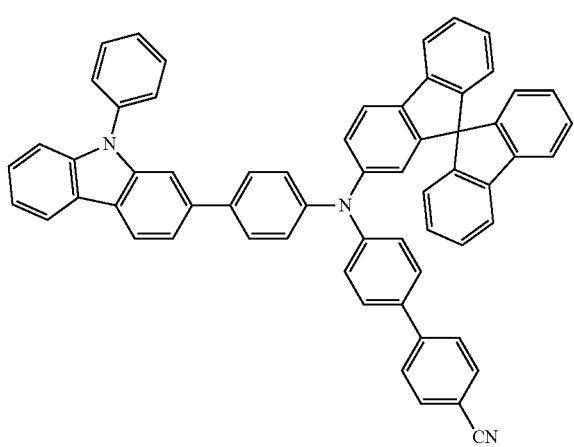

46

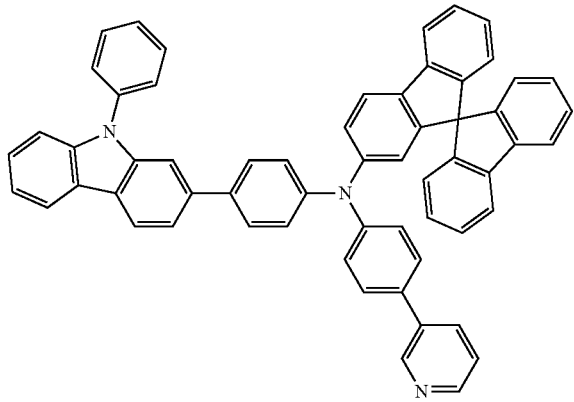

47

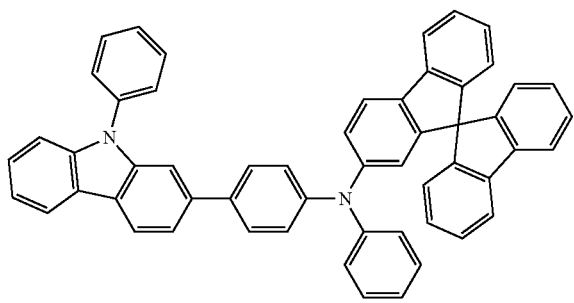

48

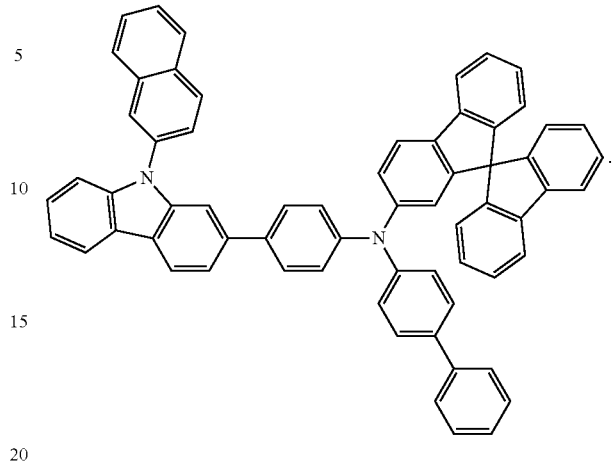

16. An organic light-emitting device comprising: a first electrode; a second electrode disposed opposite to the first electrode; and an organic layer disposed between the first electrode and the second electrode, wherein the organic layer comprises at least one of the compounds represented by Formula 1 below:

<Formula 1>

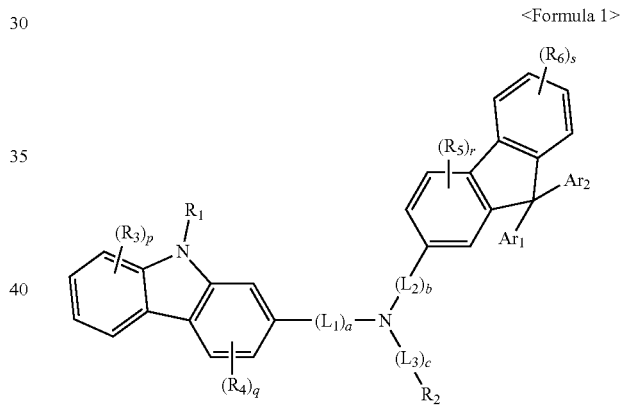

wherein, in Formula 1,
Ar$_1$ and Ar$_2$ are each independently a substituted or unsubstituted C$_6$-C$_{30}$ aryl group, and Ar$_1$ and Ar$_2$ are optionally linked to each other via a single bond;
L$_1$ to L$_3$ are each independently a substituted or unsubstituted C$_3$-C$_{10}$ cycloalkylene group, a substituted or unsubstituted C$_2$-C$_{10}$ heterocycloalkylene group, a substituted or unsubstituted C$_3$-C$_{10}$ cycloalkenylene group, a substituted or unsubstituted C$_2$-C$_{10}$ heterocycloalkenylene group, a substituted or unsubstituted C$_6$-C$_{30}$ arylene group, or a substituted or unsubstituted C$_2$-C$_{60}$ hetero arylene group;
a, b, and c are each independently an integer from 0 to 5;
R$_1$ to R$_6$ are each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_3$-$C_{60}$ heterocycloalkyl group, a substituted or unsubstituted $C_3$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —$N(Q_1)(Q_2)$, or —$Si(Q_3)(Q_4)(Q_5)$, wherein $Q_1$ to $Q_5$ are each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_3$-$C_{60}$ heterocycloalkyl group, a substituted or unsubstituted $C_3$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

p and s are each independently an integer from 1 to 4; and q and r are each independently an integer from 1 to 3.

17. The organic light-emitting device of claim 16, wherein the organic layer comprises at least one of a hole injection layer, a hole transport layer, a functional layer having both hole injection and hole transport capabilities, a buffer layer, an electron blocking layer, an emission layer, a hole blocking layer, an electron transport layer, an electron injection layer, and a functional layer having both electron injection and electron transport capabilities.

18. The organic light-emitting device of claim 17, wherein the organic layer comprises at least one of a hole injection layer, a hole transport layer, and a functional layer having both hole injection and hole transport capabilities, and the amine-based compound is in the at least one of the hole injection layer, the hole transport layer, and the functional layer having both hole injection and hole transport capabilities.

19. The organic light-emitting device of claim 18, wherein at least one of the hole injection layer, the hole transport layer, and the functional layer having both hole injection and hole transport capabilities further comprises a charge-generating material.

20. The organic light-emitting device of claim 17, wherein the organic layer comprises the emission layer; the emission layer comprises a host and a dopant; and the dopant comprises an organic metal compound including at least one of Ir, Pt, Os, Ti, Zr, Hf, Eu, Tb, and Tm.

* * * * *